(12) United States Patent
Tour et al.

(10) Patent No.: US 11,154,623 B2
(45) Date of Patent: Oct. 26, 2021

(54) MECHANICAL OPENING OF LIPID BILAYERS BY MOLECULAR NANOMACHINES

(71) Applicants: William Marsh Rice University, Houston, TX (US); Durham University, Durham (GB)

(72) Inventors: James M. Tour, Bellaire, TX (US); Robert Pal, Durham (GB); Victor García-López, Houston, TX (US); Lizanne Nilewski, Houston, TX (US)

(73) Assignees: WILLIAM MARSH RICE UNIVERSITY, Houston, TX (US); DURHAM UNIVERSITY, Durham (GB)

( * ) Notice: Subject to any disclaimer, the term of this patent is extended or adjusted under 35 U.S.C. 154(b) by 158 days.

(21) Appl. No.: 16/316,716

(22) PCT Filed: Jul. 14, 2017

(86) PCT No.: PCT/US2017/042148
§ 371 (c)(1),
(2) Date: Jan. 10, 2019

(87) PCT Pub. No.: WO2018/013930
PCT Pub. Date: Jan. 18, 2018

(65) Prior Publication Data
US 2019/0290785 A1    Sep. 26, 2019

Related U.S. Application Data

(60) Provisional application No. 62/362,206, filed on Jul. 14, 2016.

(51) Int. Cl.
| | | |
|---|---|---|
| *A61B 5/00* | (2006.01) |
| *A61B 8/00* | (2006.01) |
| *A61B 10/00* | (2006.01) |
| *A61K 49/00* | (2006.01) |
| *A61K 41/00* | (2020.01) |
| *C12N 15/87* | (2006.01) |
| *C09B 57/00* | (2006.01) |
| *C07F 5/02* | (2006.01) |
| *C09B 23/04* | (2006.01) |
| *C07D 335/12* | (2006.01) |

(52) U.S. Cl.
CPC .......... *A61K 49/0032* (2013.01); *A61K 41/00* (2013.01); *A61K 49/0021* (2013.01); *A61K 49/0056* (2013.01); *C07D 335/12* (2013.01); *C07F 5/022* (2013.01); *C09B 23/04* (2013.01); *C09B 57/00* (2013.01); *C12N 15/87* (2013.01)

(58) Field of Classification Search
None
See application file for complete search history.

(56) References Cited

U.S. PATENT DOCUMENTS

| | | |
|---|---|---|
| 2010/0182693 A1 | 7/2010 | Iida et al. |
| 2014/0044791 A1 | 2/2014 | Basilion et al. |
| 2014/0065175 A1 | 3/2014 | Alonso Marti et al. |
| 2015/0297735 A1 | 10/2015 | Vlahov et al. |

FOREIGN PATENT DOCUMENTS

| | | |
|---|---|---|
| WO | WO-13/078091 A1 | 5/2013 |
| WO | WO-18/013930 A1 | 1/2018 |

OTHER PUBLICATIONS

Chiang et al. (AcsNano 2012, 6, 592-597).*
Cnossen, Arjen (2013). Overcrowded alkene-based molecular motors: from single molecule to multimotor systems (ISBN: 978-90-367-6001-0 (print), 978-90-367-6000-3 (digital)) Doctoral Thesis, Stratingh Institute for Chemistry, University of Groningen, The Netherlands.*
Li et al. (Nature Nanotechnol. 2015, 10, 161-165).*
International Search Report and Written Opinion for PCT/US17/42148, dated Sep. 27, 2017.
International Preliminary Report on Patentability for PCT/US17/42148, dated Jan. 24, 2019.
Extended European Search Report for Application No. 17828535.9, dated Mar. 5, 2020.
Abendroth, JM et al., "Controlling Motion at the Nanoscale: Rise of the Molecular Machines," ACS Nano, vol. 9, No. 8, 2015, pp. 7746-7768.
Pollard, MM et al., "Rate Acceleration of Light-Driven Rotary Molecular Motors," Advanced Functional Materials, vol. 17, 2007, pp. 718-729.
Garcia-Lopez, V et al., Unimolecular submersible nanomachines. Synthesis, actuation and monitoring. *Nano Lett.* 15, 8229-8239 (2015).
Garcia-Lopez, V et al., Synthesis and Photostability of Unimolecular Submersible Nanomachines: Toward Single-Molecule Tracking in Solution, Org. Lett. 2016, 18, 2343-2346.
Saywell, A. et al., Light-Induced Translation of Motorized Molecules on a Surface, ACS Nano 2016, 10, 10945-10952.

(Continued)

*Primary Examiner* — Michael G. Hartley
*Assistant Examiner* — Melissa J Perreira
(74) *Attorney, Agent, or Firm* — Winstead PC

(57) ABSTRACT

Embodiments of the present disclosure pertain to methods of opening a lipid bilayer by associating the lipid bilayer with a molecule that includes a moving component capable of moving (e.g., rotating) in response to an external stimulus; and exposing the molecule to an external stimulus before, during or after associating the molecule with the lipid bilayer. The exposing causes the moving component of the molecule to move and thereby open the lipid bilayer (e.g., by pore formation). The external stimuli may include an energy source, such as ultraviolet light. The opened lipid bilayer may be a component of cell membranes in vitro or in vivo. The opening of the lipid bilayer may allow for the passage of various materials (e.g., active agents, such as peptide-based drugs) through the lipid bilayer and into cells. Additional embodiments of the present disclosure pertain to the aforementioned molecules for opening lipid bilayers.

34 Claims, 44 Drawing Sheets

(56) References Cited

OTHER PUBLICATIONS

Figure 1:
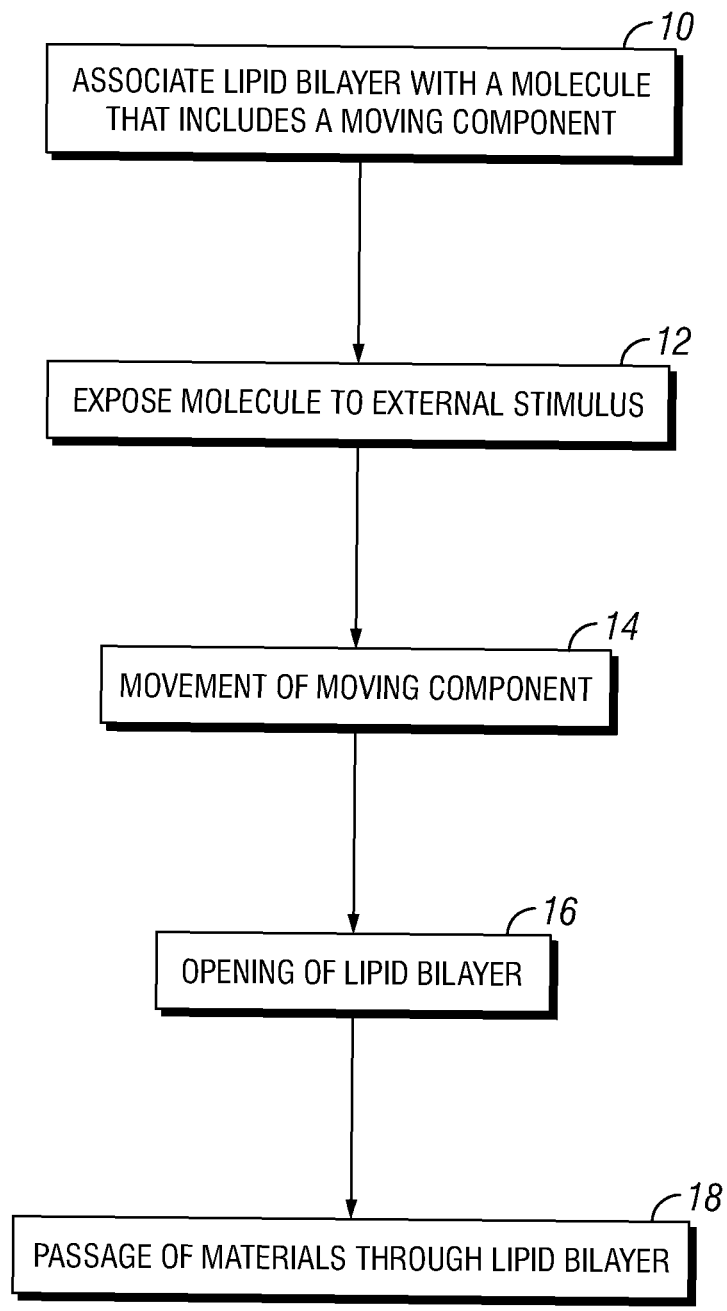

Baswanth, O., et al., On the possibility to accelerate the thermal isomerizations of overcrowded alkene-based rotary molecular motors with electron-donating or electron-withdrawing subsituents, J Mol Model (2016) 22:219.
Pollard, M., et al, LIght-Driven Rotary Molecular Motors on Gold Nanoparticles, Chem Eur. J. 2008, 14, 11610-11622.
Morin, J et al., En Route to a Motorized Nanocar, Org. Lett., vol. 8, No. 8, 2006.
Wiel, M. et al., New Procedure for the Preparation of Highly Sterically Hindered Alkenes Using a Hypervalent Iodine Reagent, Org. Biomol. Chem. 2005, 3, 28-30.
Van Delden, R., et al., A Donor-Acceptor Substituted Molecular Motor: Unidirectional Rotation Driven by Visible Light, Org. Biomol. Chem. 2003, 1, 33-35.
Lakshmanan, S. et al; Physical energy for drug delivery; poration, concentration and activation. Adv. Drug. Deliv. Rev. 71, 98-114 (2014).
Chang, D. C. Cell poration and cell fusion using an oscillating electric field. Biophys. J. 56, 641-652 (1989).
Liu, D., Wang, L., Wang, Z. & Cuschieri, A. Magnetoporation and magnetolysis of cancer cell via carbon nanotubes induced by rotating magnetic fields. Nano Lett. 12, 5117-5121 (2012).
Ivanov, I. T. Spectrofluorometric and microcalorimetric study of the thermal poration relevant to the mechanism of thermohaemolysis. Int. J. Hyperthermia 15, 29-43 (1999).
Tachibana, K., Uchida, T., Ogawa, K., Yamashita, N. & Tamura, K. Introduction of cell-membrane porosity by ultrasound. Lancet 353, 1409 (1999).
Waleed, M., Hwang, S. H. Kim, J. D., Shabbir, I., Shin, S. M. & Lee, Y. G. Single-cell optoporation and transfection using femtosecond laser and optical tweezers. Biomed. Opt. Express 4, 1533-1547 (2013).
Barber, D. M., et al, Optical control of neuronal activity using a light-operated GIRK channel opener (LOGO). Chem. Sci. 7, 2347-2352 (2016).
Broichhagen, J., Podewin, T., Meyer-Berg, H., von Ohlen, Y., Johnston, N. R., Jones, B. J., Bloom, S. R., Rutter, G. A., Hoffman-Röder, A., Hodson, D. J. & Trauner, D. Optical control of insulin secretion using an Incretin switch. Angew. Chem. Int. Ed. 54, 15565-15569 (2015).
Watson, M. A. & Cockroft, S. L. Man-made molecular machines: membrane bound. Chem. Soc. Rev. 45, 6118-6129 (2016).
Xu, T., Gao, W., Xu, L.-P., Zhang, X. & Wang, S. Fuel-free synthetic micro-/nanomachines. Adv. Mater. 29, 1603250 (2017).
Haywood-Reid, P. L., Zipf, D. R. & Springer, W. R. Quantification of integrin subunits on human prostatic cell lines—comparison of nontumorigenic and tumorigenic lines. The Prostate 31, 1-8 (1997).
Collins, A. T., Berry, P. A., Hyde, C., Stower, M. J. & Maitland, N. J. Prospective identification of tumorigenic prostate cancer stem cells. Cancer Research, 65, 10946-10951 (2005).
Huang, C. W., Li, Z. & Conti, P. S. In vivo near-infrared fluorescence imaging of integrin $\alpha 2\beta 1$ in prostate cancer with cell-penetrating-peptide-conjugated DGEA Probe. J. Nucl. Med. 52, 1979-1986 (2011).
Mandelin, J., Cardó-Vila, M., Driessen, W. H., Mathew, P., Navone, N. M., Lin, S. H., Logothetis, C. J., Rietz, A. C., Dobroff, A. S., Proneth, B. & Sidman, R. L. Selection and identification of ligand peptides targeting a model of castrate-resistant osteogenic prostate cancer and their receptors. Proc. Natl Acad. Sci. USA 112, 3776-3781 (2015).
Pal, R. Phase modulation nanoscopy: a simple approach to enhanced optical resolution. Faraday Discuss. 177, 507-515 (2015).
Butler, S. J., Delbianco, M., Lamarque, L., McMahon, B., Neil, E. R., Pal, R., Parker, D., Walton, J. W. & Zwier, J. M. EuroTracker dyes: design, synthesis, structure and photophysical properties of very bright europium complexes and their use in bioassays and cellular optical imaging. Dalton Trans. 44, 4791 (2015).
Kessner, S., Krause, A., Rothe, U. & Bendas, G. Investigation of the cellular uptake of E-Selectin-targeted immunoliposomes by activated human endothelial cells. Biochim. Biophys. Acta 1514, 177-190 (2001).
Dunn, W. A., Hubbard, A. L., Aronson, N. N. Low temperature selectively inhibits fusion between pinocytic vesicles and lysosomes during heterophagy of 125I-Asialofetuin by the perfused rat liver. J. Biol. Chem. 255, 5971-5978 (1980).
Purcell, E. M. Life at low Reynolds Number. Amer. J. Phys. 45, 3-11 (1977).
Lecoeur, H. Nuclear apoptosis detection by flow cytometry: influence of endegenous endonucleases. Exp. Cell. Res. 277, 1-14 (2002).
Elmore, S. Apoptosis: a review of programmed cell death. Toxicol Pathol. 35, 495-516 (2007).
Barros, L. F., Kanaseki, T., Sabirov, R., Morishima, S., Castro, J., Bittner, C. X., Maeno, E., Ando-Akatsuka, Y., & Okada, Y. Apoptotic and necrotic blebs in epithelial cells display similar neck diameters but different kinase dependency. Cell Death Differ. 10, 687-697 (2003).
Chen, J., Kistemaker, C. M., Robertus, J., & Feringa, B. L. Molecular stirrers in action. J. Am. Chem. Soc. 136, 14924 (2014).
Sandre, O., Moreaux, L. & Brochard-Wyart, F. Dynamics of transient pores in stretched vesicles. Proc. Natl. Acad. Sci. U.S.A. 96, 10591-10596 (1999).
Li, F., Chan, C. U. & Ohl, C. D. Yield strength of human erythrocyte membranes to impulsive stretching. Biophys. J. 105, 872-879 (2013).
Evans, E. & Smith, B. A. Kinetics of hole nucleation in biomembrane rupture. New J. Phys. 13, 095010 (2011).
Shigematsu, T., Koshiyama, K. & Wada, S. Effects of stretching speed on mechanical rupture of phospholipid/cholesterol bilayers: molecular dynamics simulation. Sci. Rep. 5, 15369 (2015).
Bennett, W. F. D., Sapay, N. & Tieleman, D. P. Atomistic simulations of pore formation and closure in lipid bilayers. Biophys. J. 106, 210-219 (2014).
Wang, X., Shindel, M.S., Wang, S.-W. & Ragan, R. Elucidating driving forces for liposome rupture: external perturbations and chemical affinity. Langmuir 28, 7417-7427 (2012).
Laprell, L., Hüll, K., Stawski, P., Schön, C., Michalakis, S., Biel, M., Sumser, M. P., Trauner, D. Restoring light sensitivity in blind retinae using a photochromic AMPA receptor agonist. ACS Chem. Neurosci. 7, 15-20 (2016).
Chu, P.L., Wang, L.Y., Khatua, S., Kolomeisky, A. B., Link, S., Tour, J. M. Synthesis and single-molecule imaging of highly mobile adamantane-wheeled nanocars. ACS Nano 7, 35-41 (2013).
Wang, D., Fan, J., Gao, X., Wang, B., Sun, S., Peng, X. Carboxyl BODIPY dyes from bicarboxylic anhydrides: one pot preparation, spectral properties, photostability, and biolabeling. J. Org. Chem. 74, 7675-7683 (2009).
Brouwer, A. M. Standards for photoluminescence quantum yield measurements in solution. Pure Appl. Chem. 83, 2213-2228 (2011).
Lakowicz, J. R. Principles of Fluorescence Spectroscopy, Springer, New York, USA, pp. 54-55 (2006).

\* cited by examiner

R= FUNCTIONAL ADDENDS

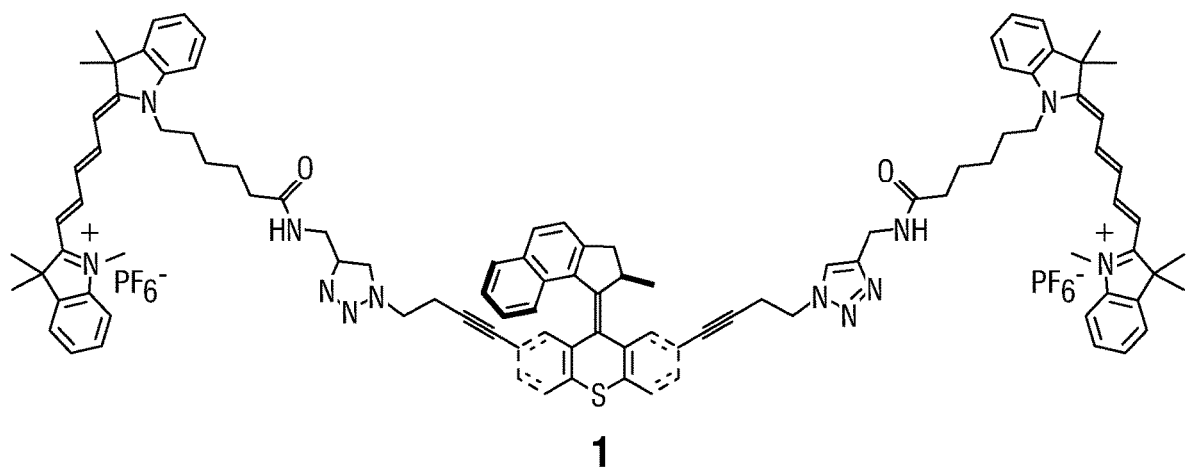
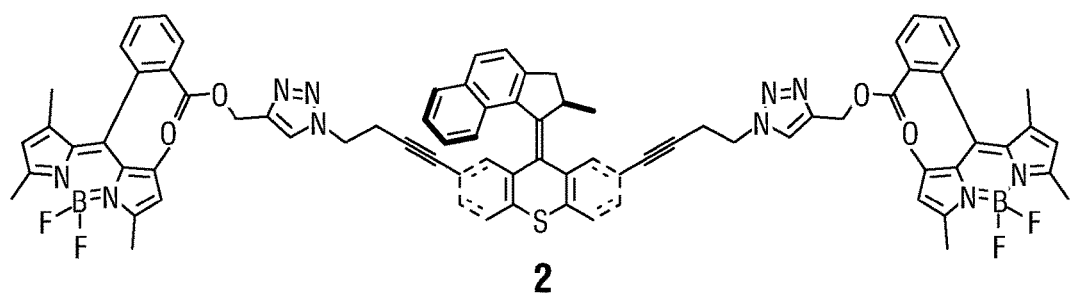
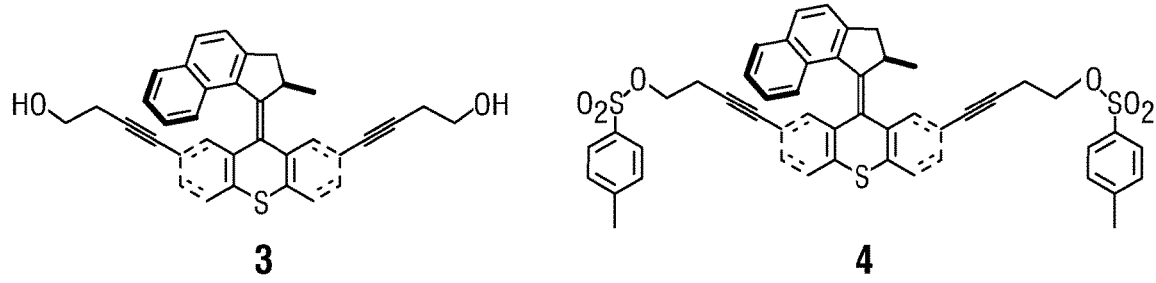
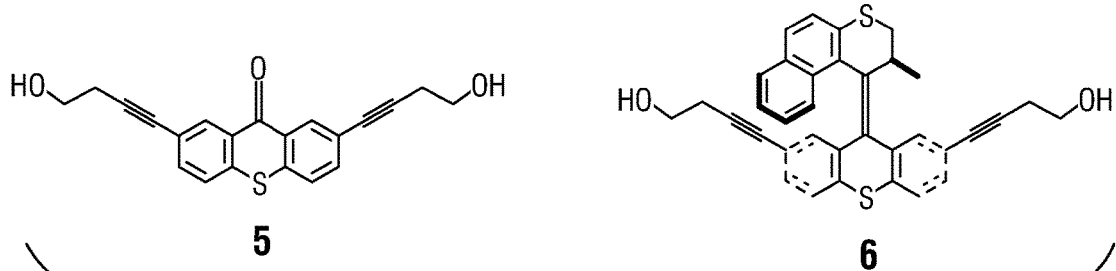
FIG. 2C

CIS AND TRANS ISOMERS

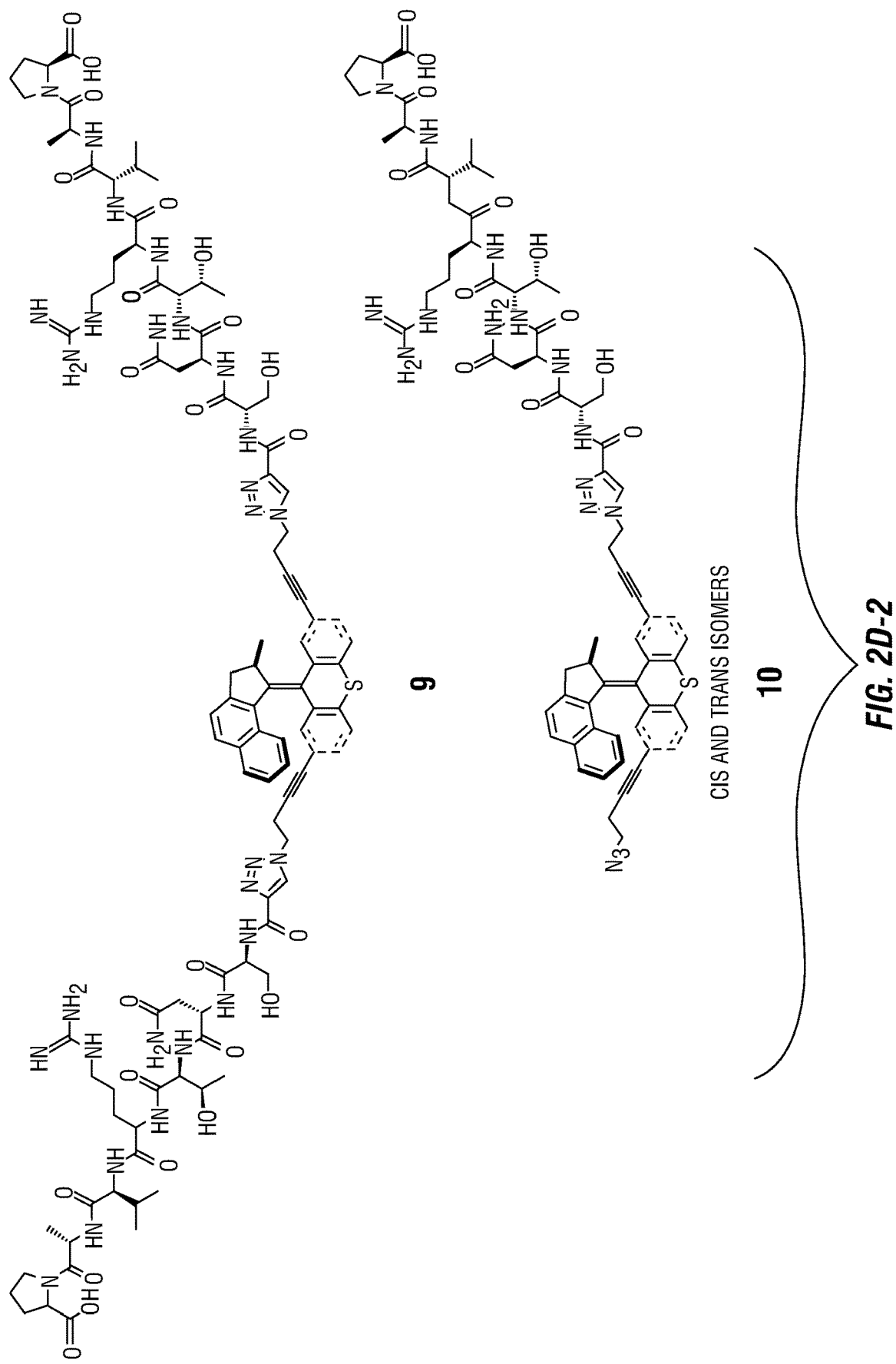

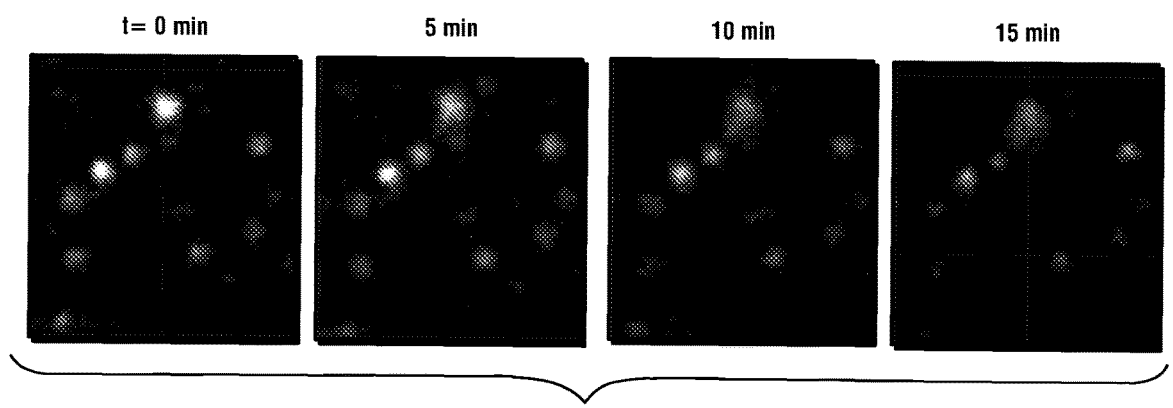
FIG. 4E
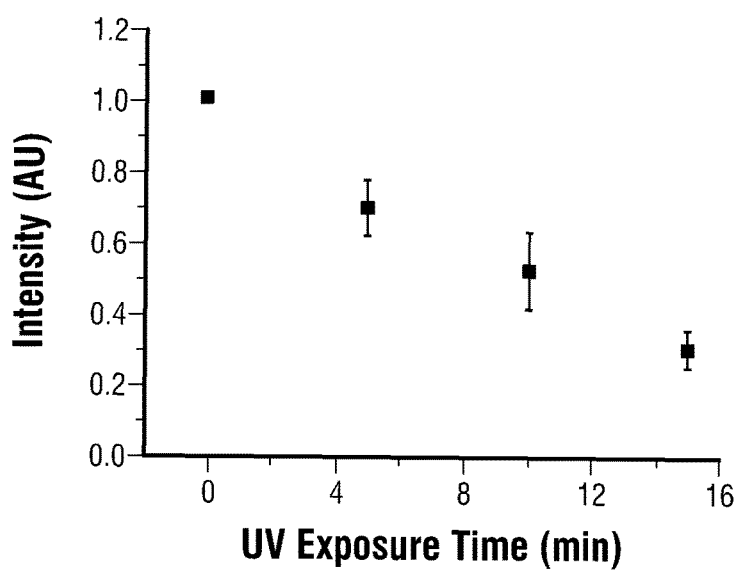
FIG. 4F
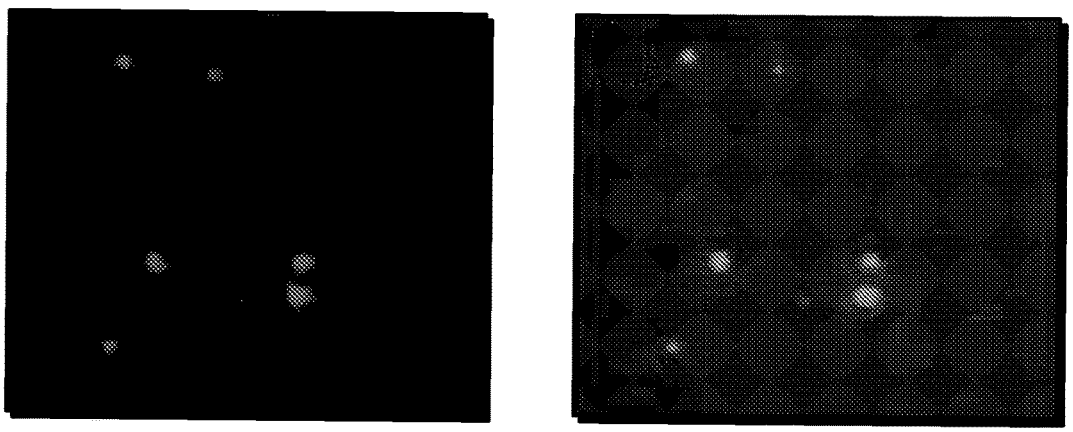
FIG. 4G  FIG. 4H

16

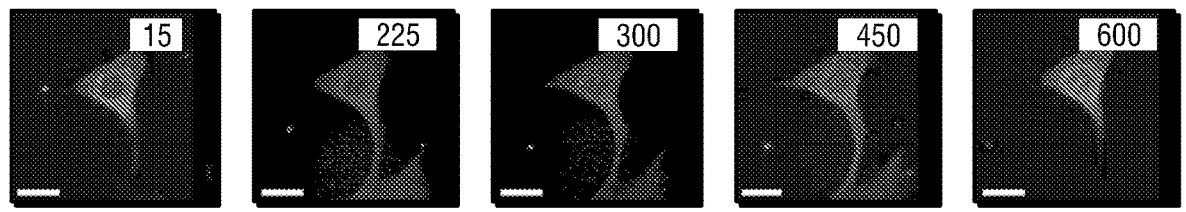
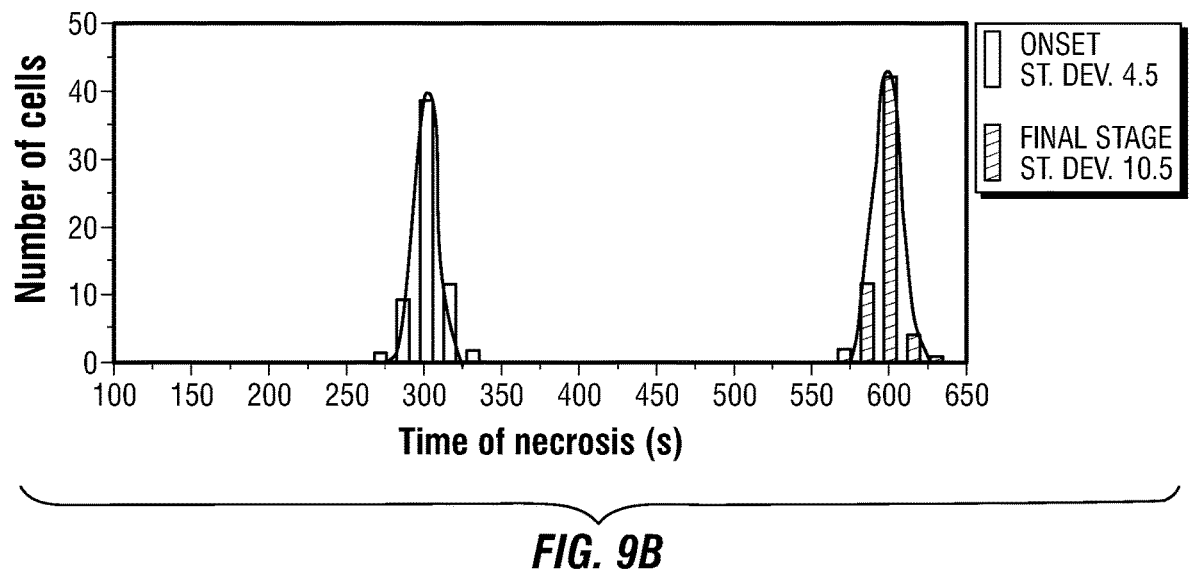
FIG. 9B
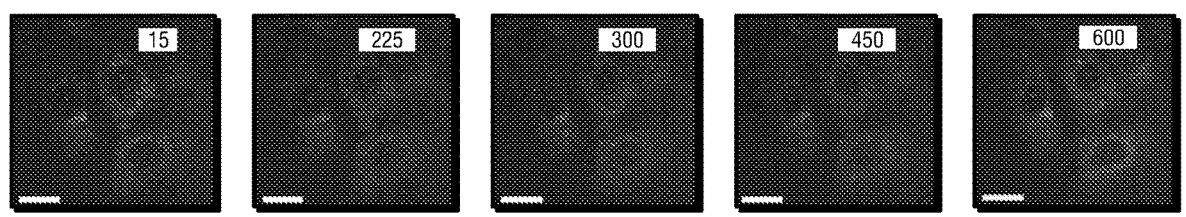
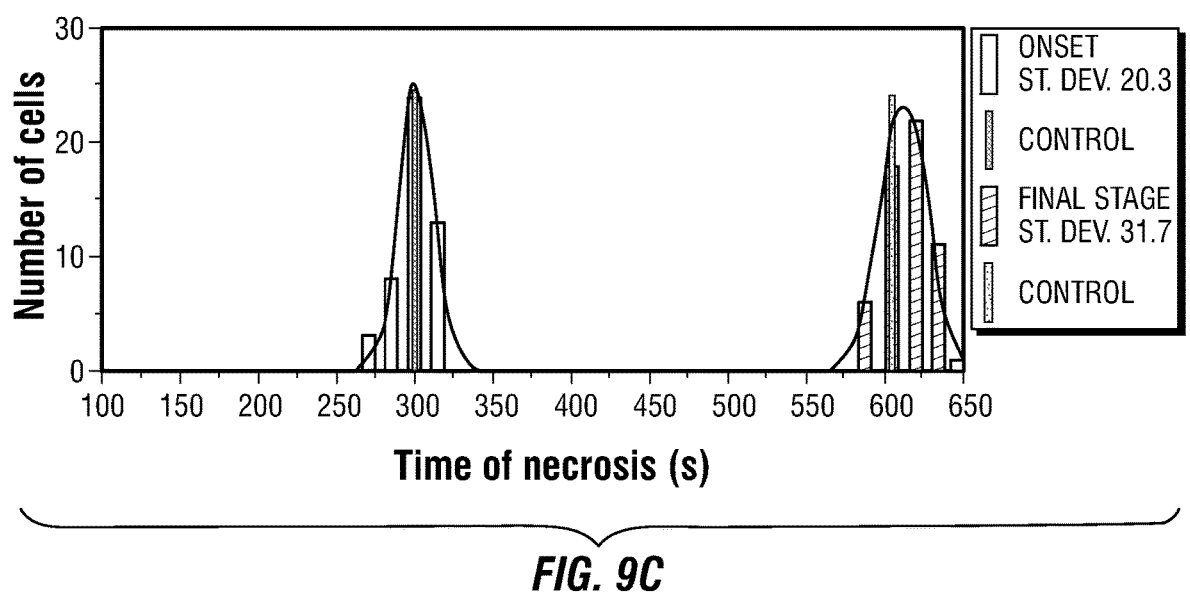
FIG. 9C

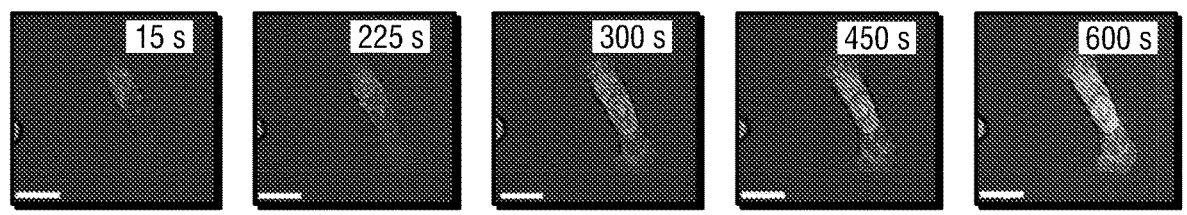
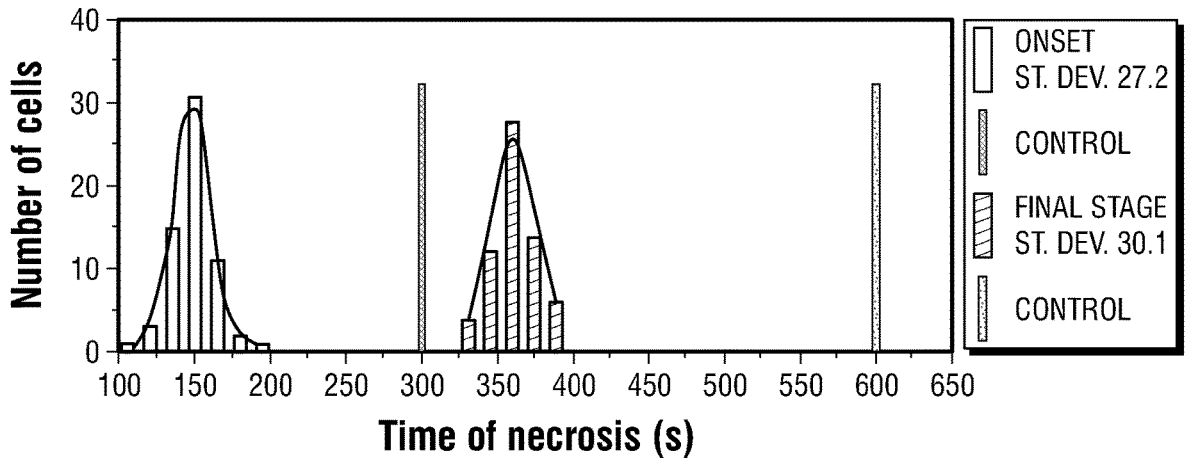
FIG. 10C
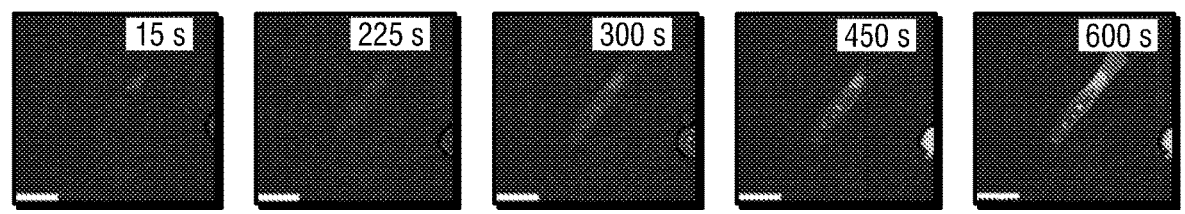
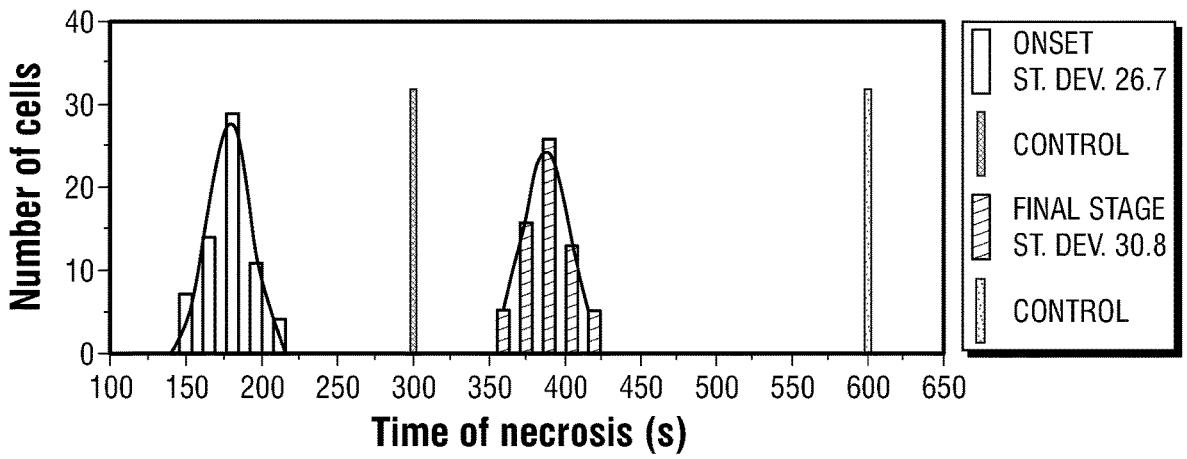
FIG. 10D

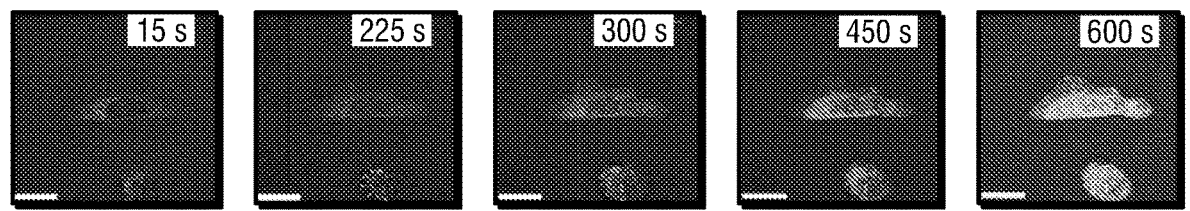
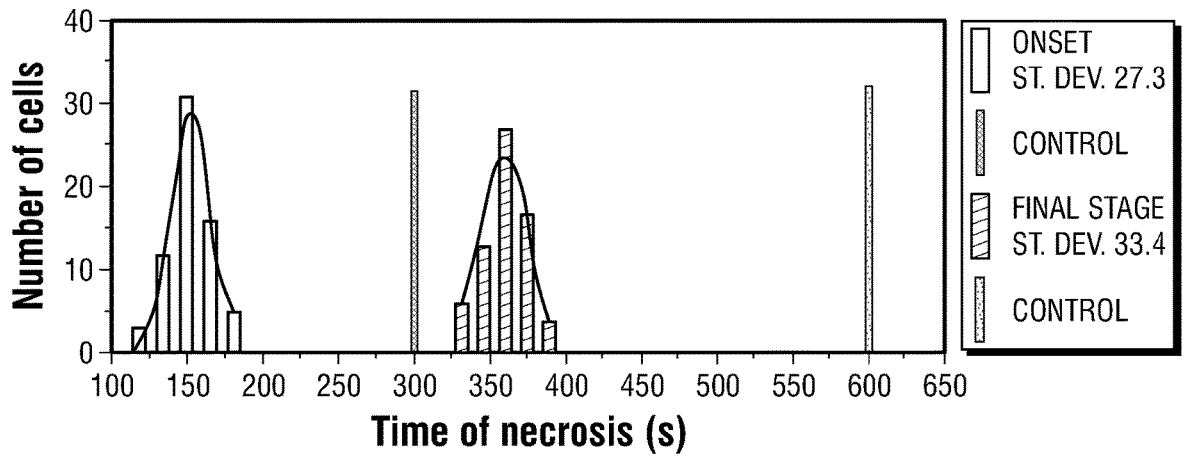
FIG. 10E
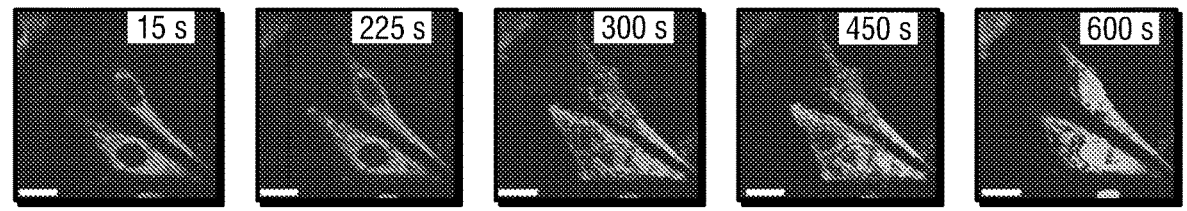
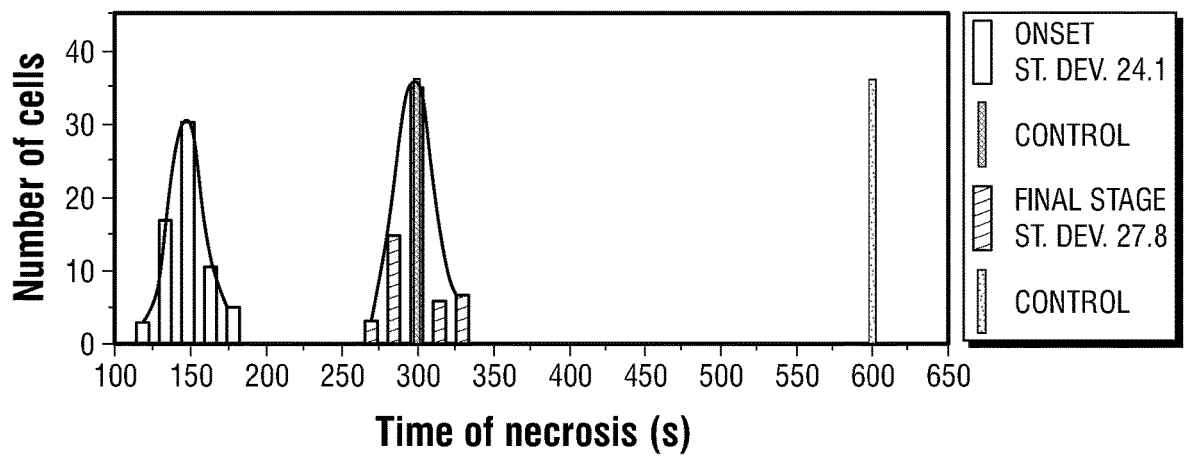
FIG. 11A

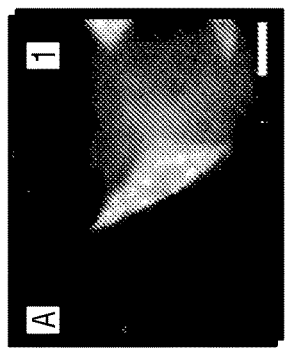 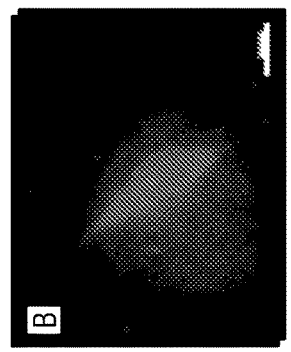 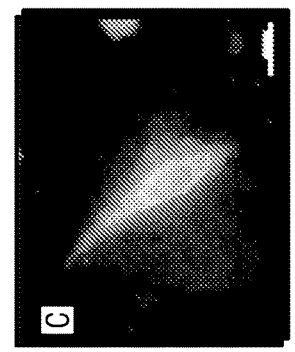
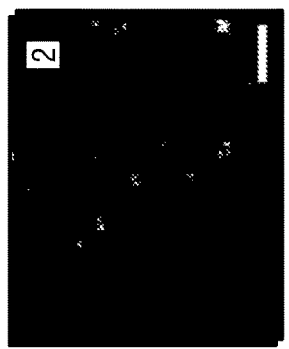 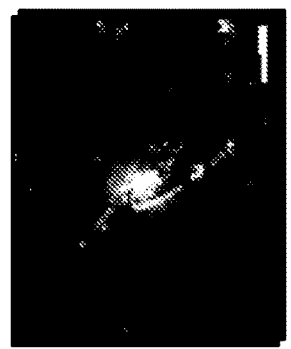 
 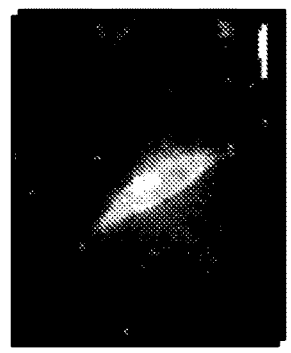 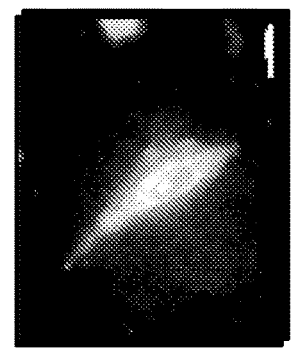
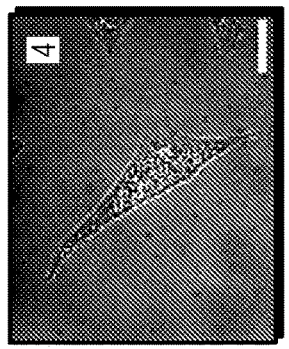 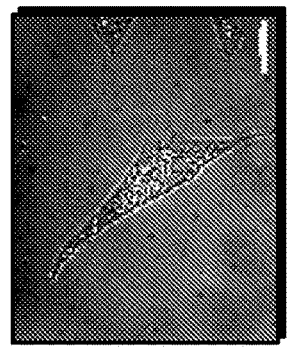 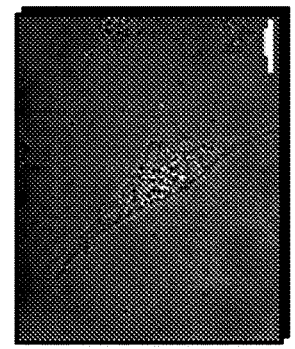
*FIG. 18A*   *FIG. 18B*   *FIG. 18C*

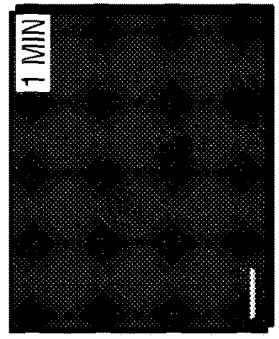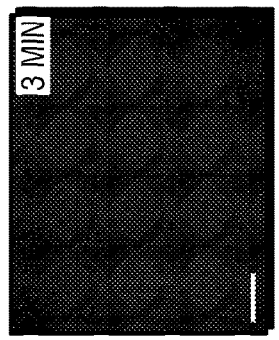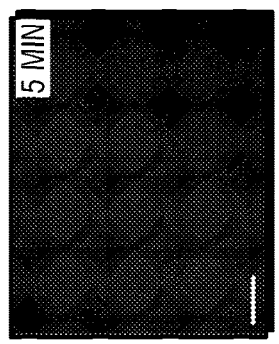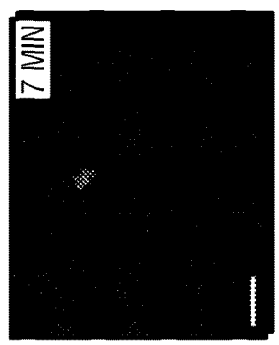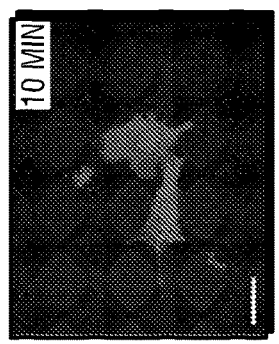
*FIG. 19A*
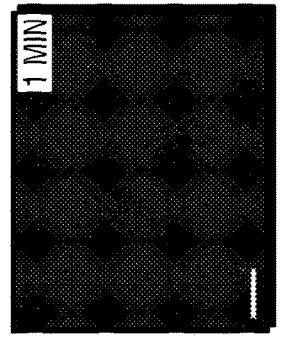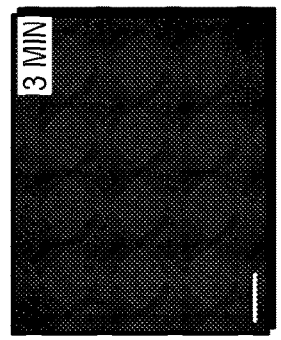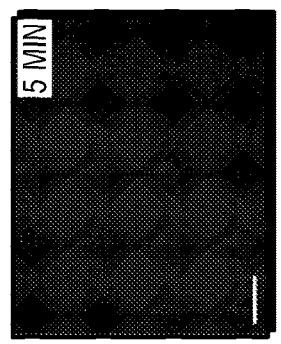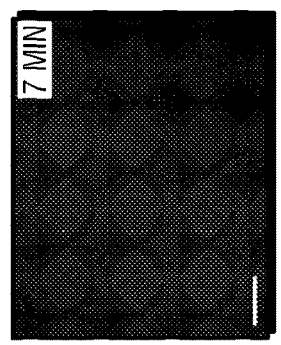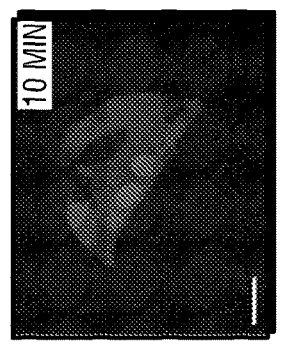
*FIG. 19B*

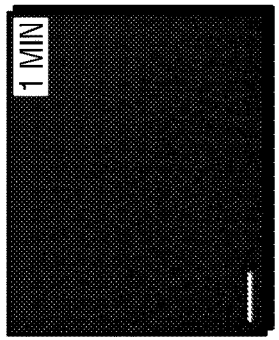
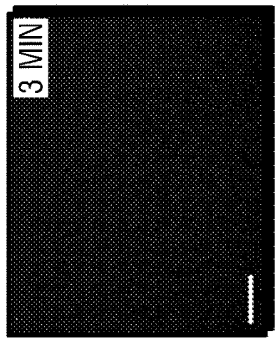
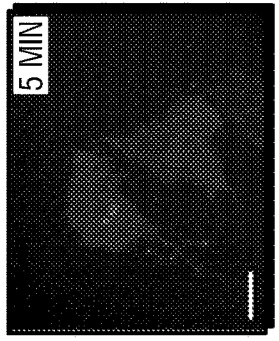
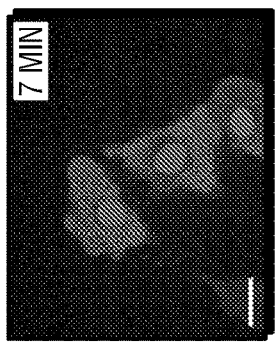
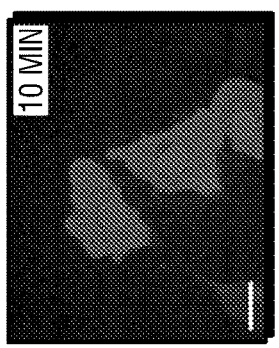
*FIG. 19C*
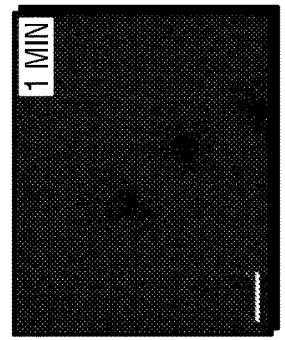
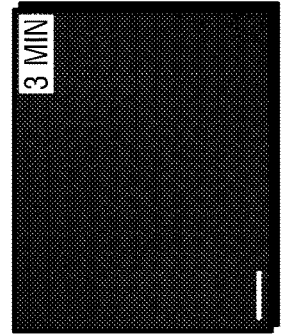
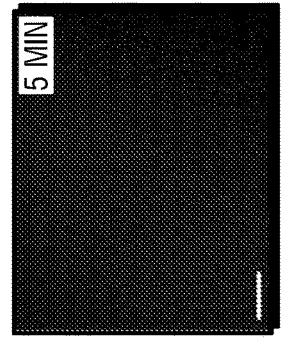
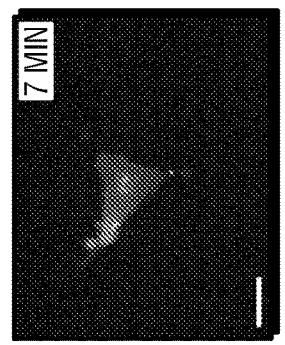
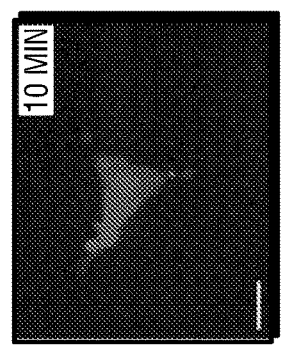
*FIG. 19D*

Figure 4A:
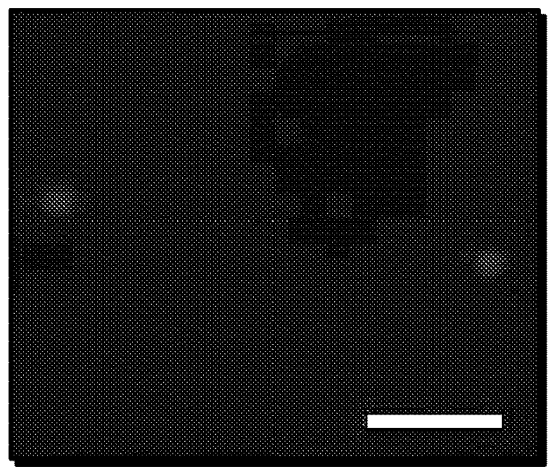
Figure 4B:
Figure 4C:
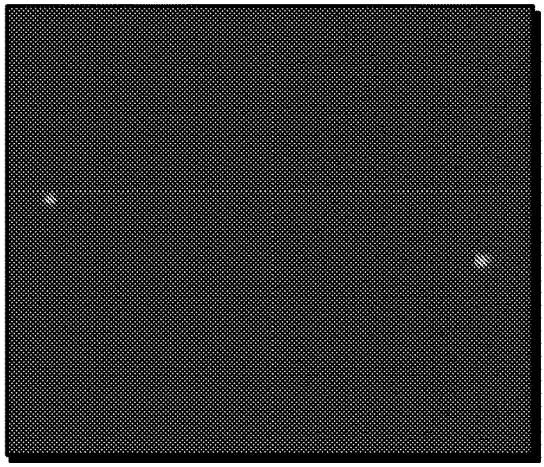
Figure 4D:
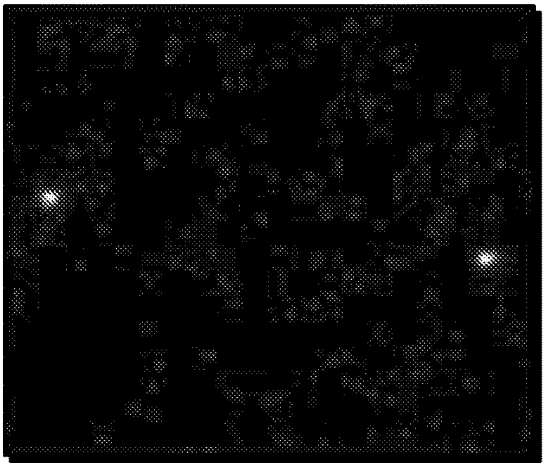
Figure 4I:
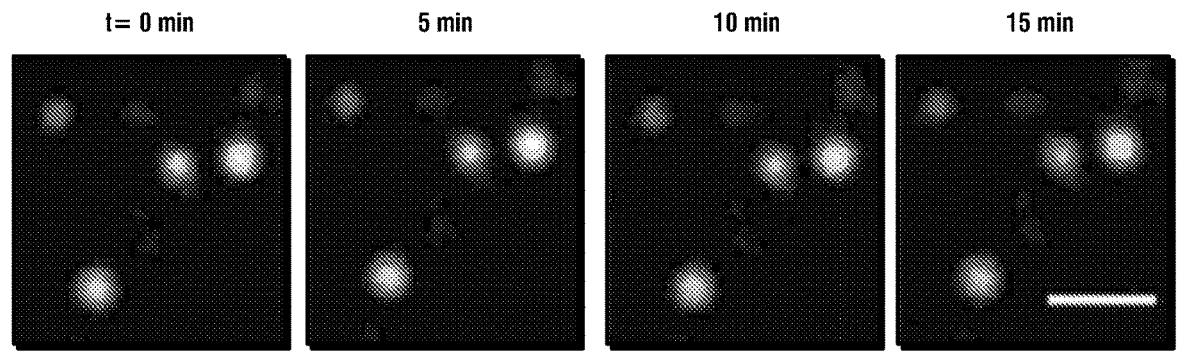
Figure 4J:
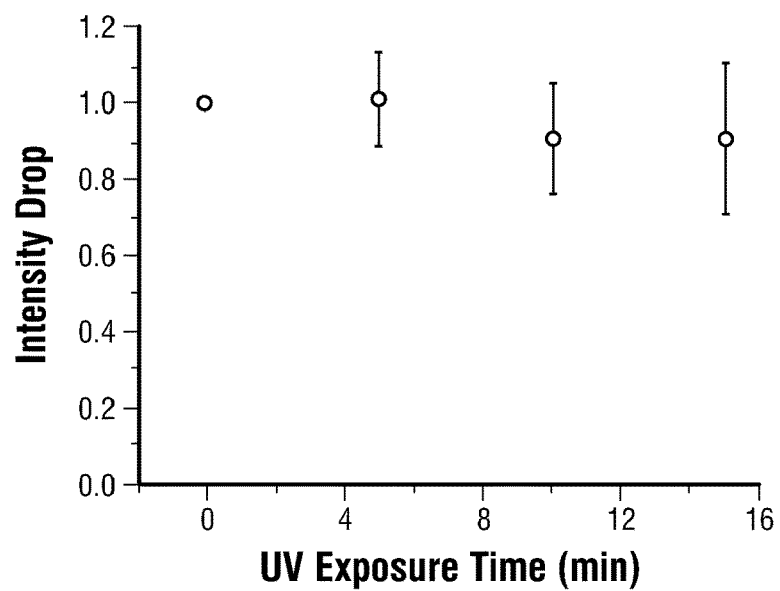
Figure 4K:
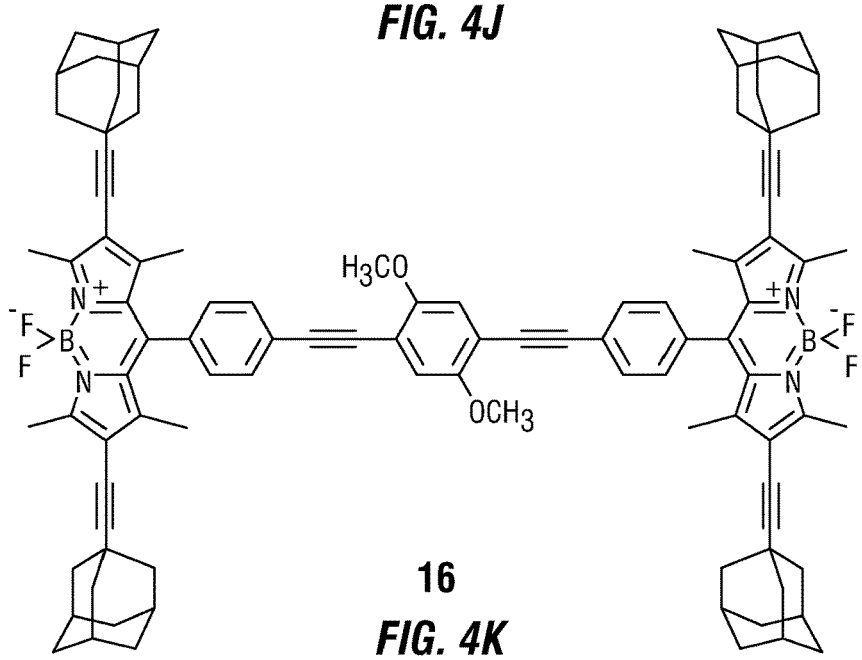

MECHANICAL OPENING OF LIPID BILAYERS BY MOLECULAR NANOMACHINES

CROSS-REFERENCE TO RELATED APPLICATIONS

This application claims priority to U.S. Provisional Patent Application No. 62/362,206, filed on Jul. 14, 2016. The entirety of the aforementioned application is incorporated herein by reference.

STATEMENT REGARDING FEDERALLY SPONSORED RESEARCH

Not applicable.

BACKGROUND

Current methods of delivering materials through lipid bilayers suffer from numerous limitations, such as ineffective delivery due to cellular resistance, and lack of specificity for desired lipid bilayers. The present disclosure addresses the aforementioned limitations.

SUMMARY

In some embodiments, the present disclosure pertains to methods of opening a lipid bilayer by associating the lipid bilayer with a molecule that includes a moving component capable of moving (e.g., rotating) in response to an external stimulus; and exposing the molecule to an external stimulus. The exposing can occur before, during or after associating the molecule with the lipid bilayer. The exposing causes the moving component of the molecule to move. Thereafter, the movement facilitates the opening of the lipid bilayer. Additional embodiments of the present disclosure pertain to the aforementioned molecules.

The molecules of the present disclosure may include various additional components. For instance, in some embodiments, the molecules of the present disclosure may also include a base component that is capable of embedding with a lipid bilayer. Additional components of the molecules of the present disclosure can also include, without limitation, targeting agents for directing the molecule to a desired lipid bilayer, tracing agents for tracking the molecule, solubilizing agents for maintaining the water solubility of the molecule, active agents that may be releasable from the molecule, and combinations thereof.

In some embodiments, the lipid bilayer that is opened by the methods and molecules of the present disclosure is a component of cell membranes in vitro. In some embodiments, the lipid bilayer is a component of cell membranes in vivo.

In some embodiments, the molecules of the present disclosure are associated with lipid bilayers in vivo in a subject. In some embodiments, the association step includes administering the molecule to the subject. In some embodiments, the administered molecules may be utilized to treat a disease in a subject, such as skin-related cancers (e.g., skin cancers, colorectal cancers, oral cancers, and vaginal cancers).

The lipid bilayers of the present disclosure may be exposed to various external stimuli. In some embodiments, the external stimuli include an energy source, such as ultraviolet light, visible light, near-infra red light, a radio frequency energy source, a magnetic field, a two-photon energy source, an electric field, an electromagnetic field, and combinations thereof. In some embodiments, the energy source includes ultraviolet light.

In some embodiments, the movement of the moving component of the molecules of the present disclosure facilitates the opening of the lipid bilayer by forming pores in the lipid bilayer. In some embodiments, the opening of the lipid bilayer allows for the passage of materials through the lipid bilayer. In some embodiments, the materials include, without limitation, analytes, active agents, drugs, nucleotides, DNA, RNA, siRNA, polypeptides, enzymes, polysaccharides, imaging agents, and combinations thereof. In some embodiments, the opening of the lipid bilayer allows for the passage of materials through the lipid bilayer and into cells for various purposes.

DESCRIPTION OF THE FIGURES

FIG. 1 provides a scheme of a method of opening a lipid bilayer.

FIG. 2 provides illustrations of molecular motors and control molecules for disruption of lipid bilayers through molecular mechanical action. FIG. 2A provides a schematic of molecular machines atop a cell membrane that open the membrane by UV-activated nanomechanical action. FIG. 2B shows a representative molecular machine with a rotor portion that is light-activated to rotate relative to the larger bottom stator portion, where the addends (R) can be varied to provide the requisite solubility, fluorophores for tracking, or recognition sites for cellular targeting. FIG. 2C shows representative structures of various nanomachines, including nanomachines 1 and 2 that bear fluorophores as pendants on the stator portions for tracking their movement, nanomachines 3 and 4 that have smaller molecular sizes with no stator-addended fluorophores for their tracking, control compound 5 which has a stator segment but no rotor and no capability of being UV-activated, and control compound 6 with a slow rotor. FIGS. 2D-1 and 2D-2 show representative structures of additional nanomachines, including nanomachines 7 and 8 that are functionalized with the DGEA peptide sequence to target $\alpha_2\beta_1$-integrin overexpressed in PC-3 human prostate cancer cells, and nanomachines 9 and 10 that are functionalized with the SNTRVAP peptide sequence to bind to the 78 kDa glucose regulated protein (GRP78) targeting castrate-resistant osteogenic prostate cancer receptors on PC-3 human prostate cancer cells. Rotors in nanomachines 1-4 and 7-10 rotate at 2-3 MHz when activated with 355 to 365 nm light. Rotor in nanomachine 6 rotates at 1.8 revolutions per hour when activated with 355 to 365 nm light at 60° C., but only cis-trans isomerizes about the rotor-stator double bond at room temperature.

FIG. 3 provides a schematic of dye releasing experiments upon UV illumination.

FIG. 4 shows data related to UV light-activated molecular motor 1 (illustrated in FIG. 2C) and its releasing of encapsulated dye molecules from synthetic bilipid vesicles through nanomechanical action. FIGS. 4A-F show data related to BODIPY dye release from the vesicles. FIG. 4A shows a dark-field image of the vesicles. FIG. 4B shows a fluorescence image of molecular motor 1. FIG. 4C shows fluorescence images of BODIPY dyes. FIG. 4D shows co-localization of the images in FIGS. 4A-C. FIG. 4E shows the fluorescence image of the BODIPY dye as a function of UV-exposure time. FIG. 4F shows normalized fluorescence intensity vs UV-exposure time of 20 vesicles from 6 different sets of movies. Since different vesicles have different initial intensities, all traces are normalized according to the first data point. The error bar stands for the standard deviation of the normalized intensities. The first data point does not have an error bar. FIGS. 4G-J show control experiments with compound 16 (illustrated in FIG. 4K) instead of molecular motor 1. FIG. 4G shows a dark-field image of the vesicles. FIG. 4H shows a fluorescence image of compound 16. The image shows that 16 is incorporated into the lipid bilayer. FIG. 4I shows a fluorescence image of the BODIPY dye and compound 16 as a function of UV-exposure time. FIG. 4J shows normalized fluorescence intensity vs UV-exposure time of 20 vesicles from 5 different sets of movies. The scale bar in FIG. 4A is 10 μm and is the same for FIGS. 4B-D, FIG. 4G and FIG. 4H. The scale bar in FIG. 4I is 2 μm and is the same for all the figures in FIG. 4E and FIG. 4I.

Figure 5A:
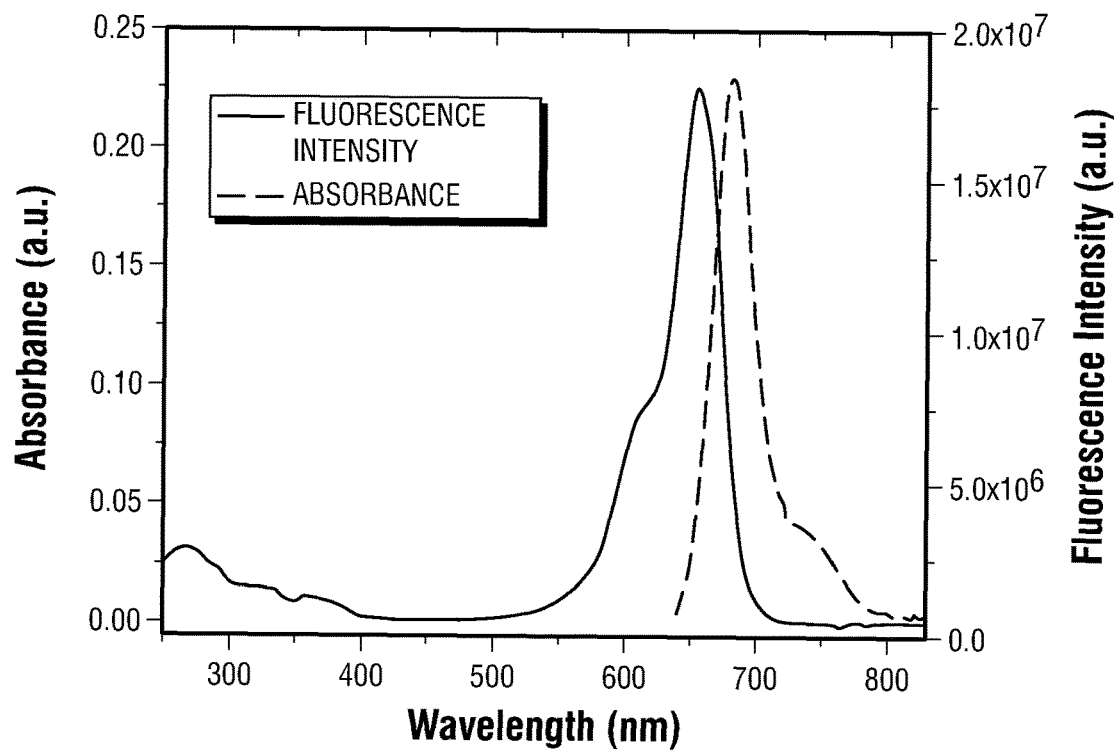
Figure 5B:
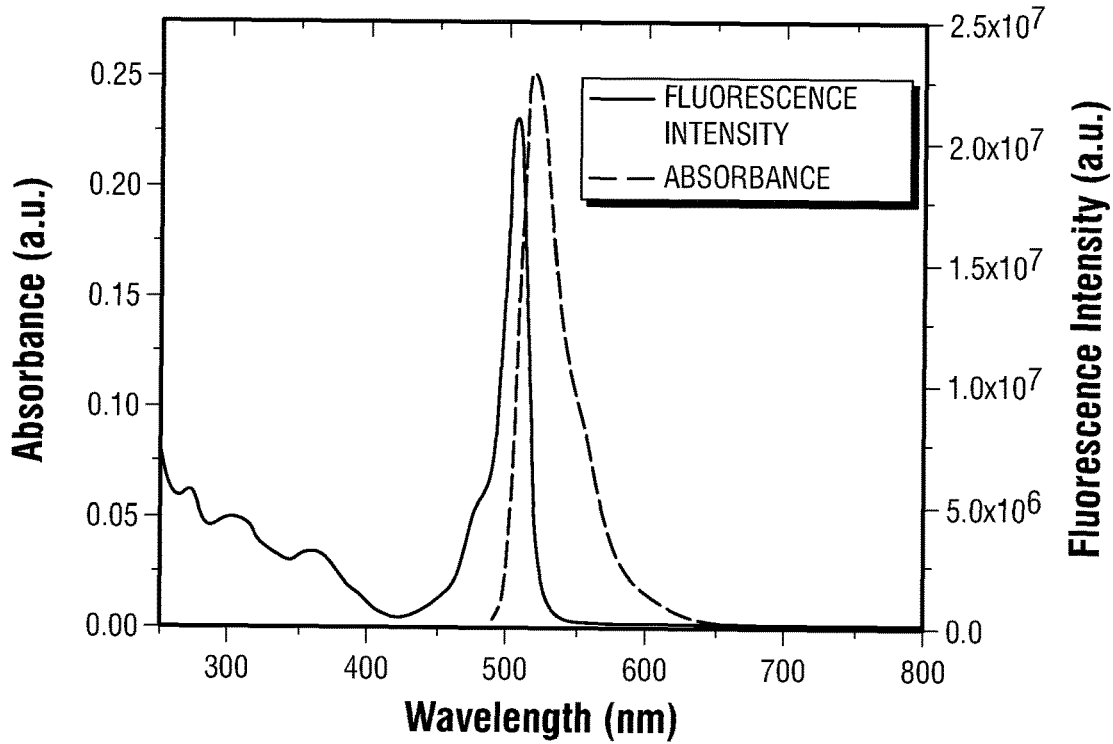

FIG. 5 shows the optical properties of molecular machines 1 and 2. FIG. 5A shows the UV/vis absorption and fluorescence spectra of molecular machine 1. Excitation was observed at 630 nm. FIG. 5B shows the UV/vis absorption and fluorescence spectra of compound 2. Excitation was observed at 474 nm.

FIG. 6 shows images of NIH 3T3 cells in the presence of the fluorescent molecular machines 1 and 2, which were studied with UV activation to cause nanomechanical-induced entry of molecular machines 1 and 2 into the cells. FIG. 6A shows images of cells exposed to nanomachine 2, including a left image (green, $C_{loading}$ 500 nM/2 h, $\lambda_{ex}$ 514 nm, $\lambda_{em}$ 520-540 nm, 2 mW); a middle image MitoTrackerRed (red, $C_{loading}$ 100 nM/30 min, $\lambda_{ex}$ 543 nm, $\lambda_{em}$ 550-600 nm, 0.5 mW); and a right image that represents the two merged transmission images verifying mitochondrial localization. FIG. 6B shows images of cells exposed to nanomachine 1, including a left image (red, $C_{loading}$ 500 nM/1 h, $\lambda_{ex}$ 633 nm, $\lambda_{em}$ 650-700 nm, 1 mW); a middle image LysoTrackerGreen (green, $C_{loading}$ 200 nM/5 min, $\lambda_{ex}$ 488 nm, $\lambda_{ex}$ 500-530 nm, 0.2 mW); and a right image that represents the two merged transmission images highlighting pit-like surface localization. FIG. 6C shows a merged transmission (488 nm, 0.2 mW) images demonstration time dependent 1 internalization. UV-activation has been achieved using parallel $\lambda_{ex}$ 355 nm, 20 mW 400 nJ/voxel total dwell time for the corresponding times noted in the images. FIG. 6D shows fluorescent images demonstrating time-dependent dispersion of formed intracellular aggregates of 1 after a 1 hour incubation and wash cycles followed by UV-activation for the corresponding times noted in the images. All scale bars are 20 μm.

FIG. 7 shows the effects of nanomachines 3 and 4, and control molecule 5 on PC-3 cells upon UV-activation. The rate of necrotic cell death and permeabilization of analytes into the cells was recorded. The UV-exposure times are shown in each image. FIG. 7A shows blank cells without molecular motors. FIG. 7B shows cells exposed to nanomachine 3. FIG. 7C shows cells exposed to nanomachine 4. FIG. 7D shows cells exposed to control molecule 5. All the exposures occurred at 500 nM with 5 minute incubation before imaging. FIG. 7E shows an identical imaging sequence using nanomachine 3 with the introduction of 100 nM PI (red, $\lambda_{ex}$ 543 nm, $\lambda_{em}$ 610-630 nm, 0.2 mW) confirming molecular mechanical cell permeabilization with intercalation of RNA and DNA primarily in the cell nuclei. All scale bars are 20 μm. The statistical analyses for each of the live cell microscopy experiments are shown to the right of the images for that row.

FIG. 8 shows interactions of compounds 3, 4 and 5 with NIH 3T3 cells, which lead to monitored necrosis. Shown are recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024×1024 pixel) images of NIH 3T3 cells depicting time-dependent UV-activated nanomechanical-induced cell morphological changes at 500 nM at 5 minute incubation time. The UV-exposure times are shown in each image. FIG. 8A shows blank cells without molecular motors. FIG. 8B shows cells with compound 3. FIG. 8C shows cells with compound 4. FIG. 8D shows cells with compound 5. All scale bars are at 20 p.m. The statistical analyses for each of the live cell microscopy experiments are shown to the right of the images for that row. The determination of onset (orange) and final stage (red) of necrosis are shown combining: 4 to 6 individual microscope slides with 5 to 6 FOV on each with an average 2.1 to 2.7 cells per FOV. The displayed standard deviations are calculated from the Gaussian fit and have been rounded up to 15 second integers due to the experimentally predefined length associated with each scanning sequence. Table 2 provides more details.

Figure 9A:
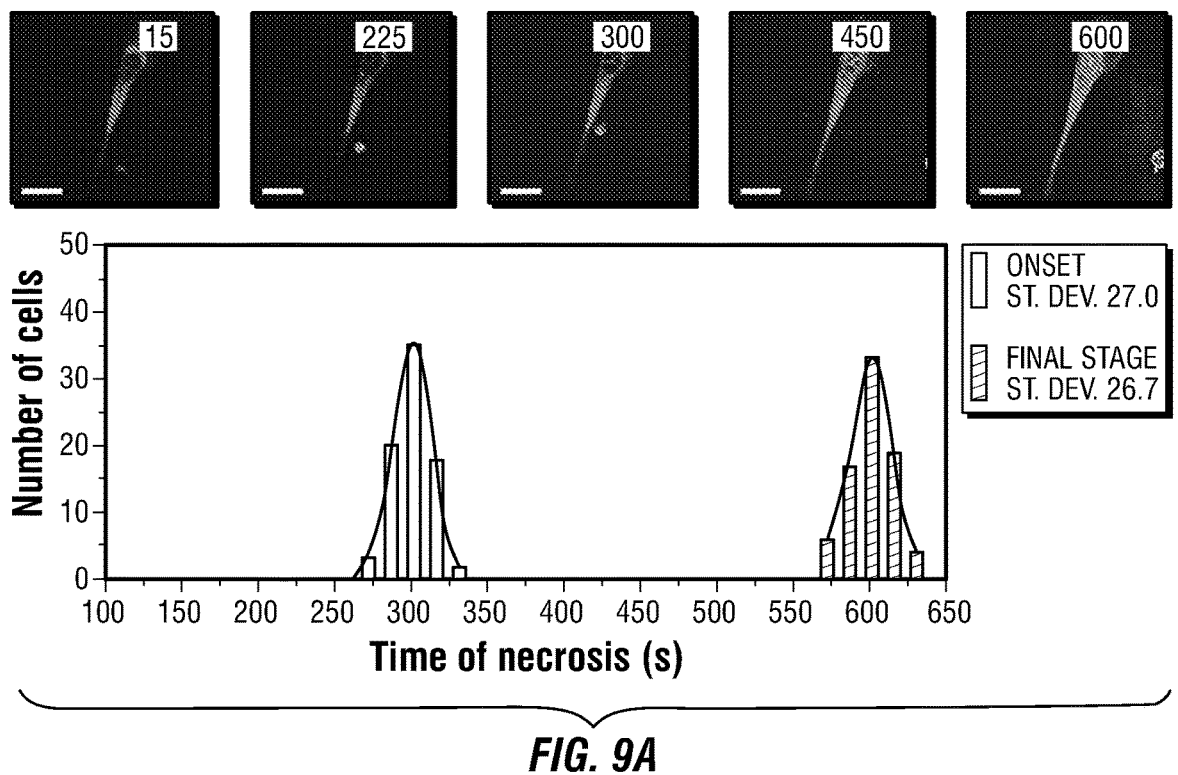
Figure 9D:
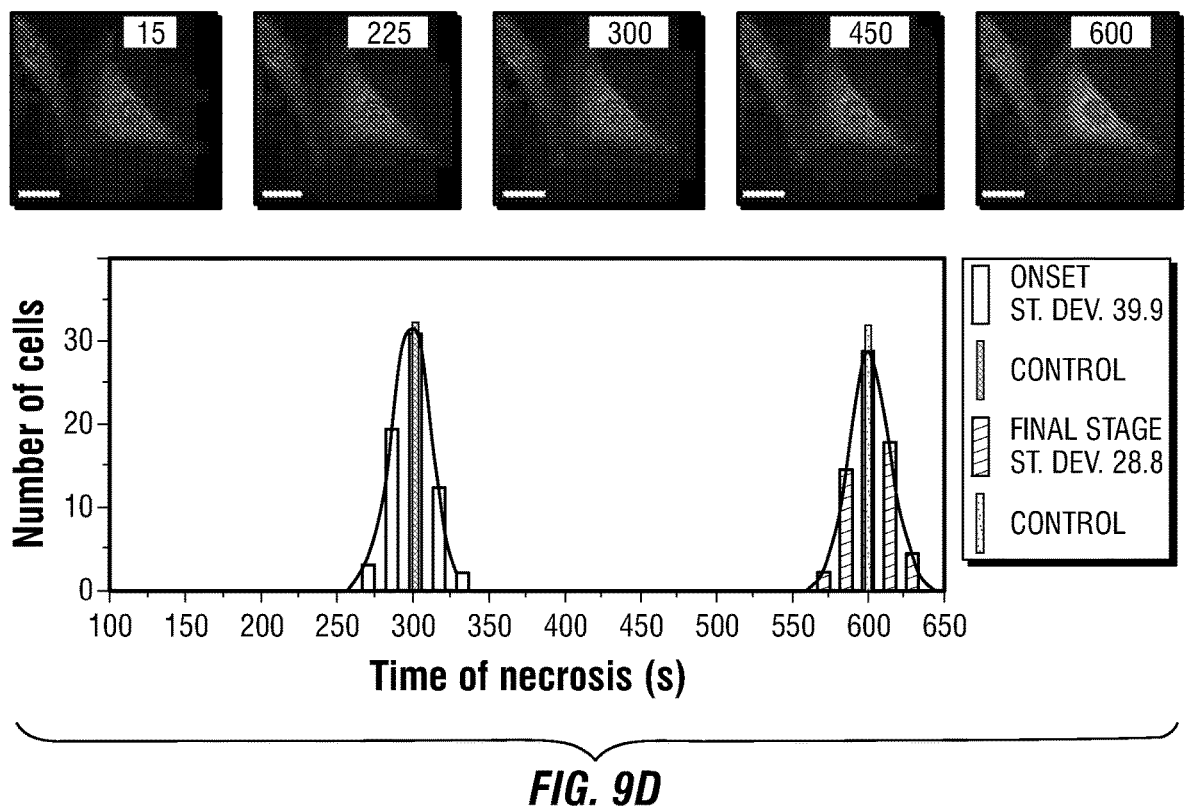
Figure 9E:
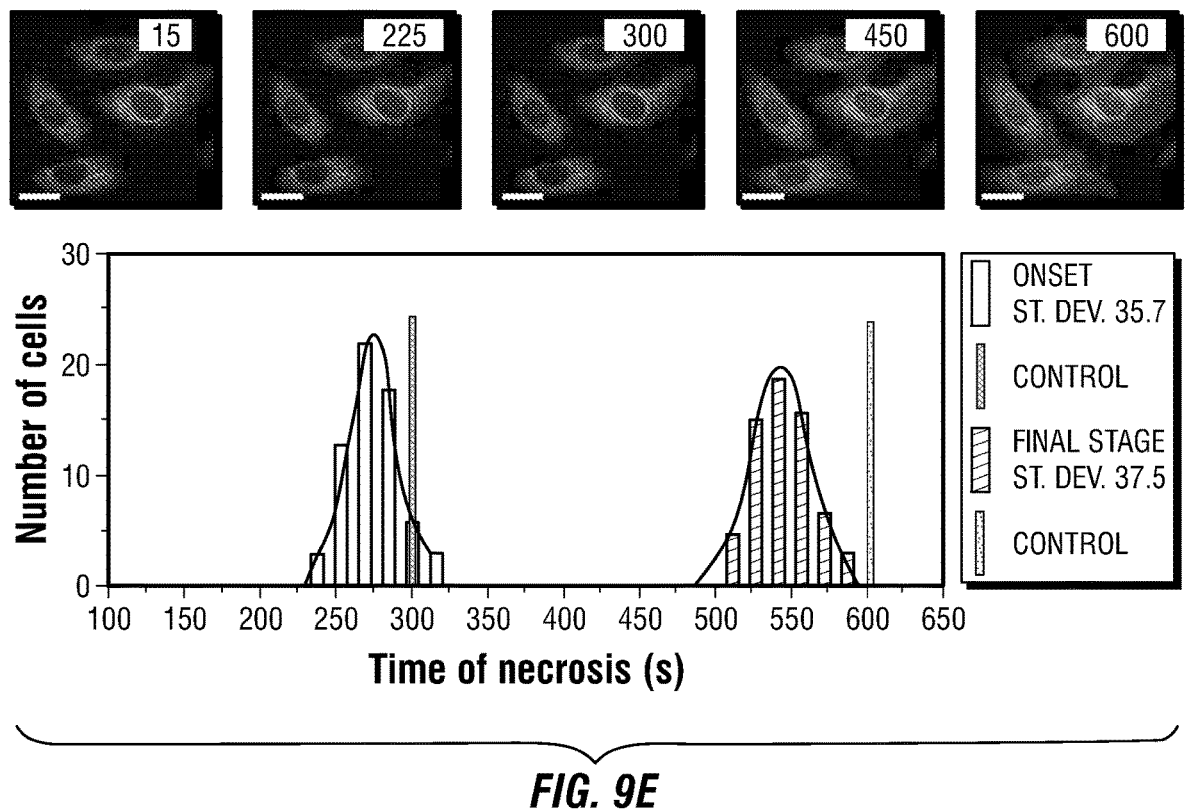

FIG. 9 shows interactions of the cis-trans isomerizing 6 with NIH 3T3 and PC-3 showing no enhanced necrosis, and non-directional rotating demethylated 3 (Table 2) showing slowed necrosis. Recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024×1024 pixel) images of NIH 3T3 and PC-3 cells depict time-dependent UV-activated cell morphological changes at 500 nM at 5 minutes incubation time using Method A. The UV-exposure times are shown in each image. FIG. 9A shows PC-3 cells without compound 6. FIG. 9B shows NIH 3T3 cells without compound 6. FIG. 9C shows NIH 3T3 cells with compound 6. FIG. 9D shows PC-3 cells with compound 6. FIG. 9E shows PC-3 cells with a demethylated version of compound 3 (no methyl group at the allylic position, so no unidirectional rotation). All scale bars are 20 μm. The statistical analyses for each of the live cell microscopy experiments are shown to the right of the images for that row. The determination of onset (orange) and final stage (red) of necrosis are shown by combining 4 to 5 individual microscope slides with 21 to 25 FOV on each with an average 2.5 to 3.1 cells per FOV. The displayed standard deviations are calculated from the Gaussian fit and have been rounded up to 15 second integers due to the experimentally predefined length associated with each scanning sequence. See Table 2 for more details.

Figure 10A:
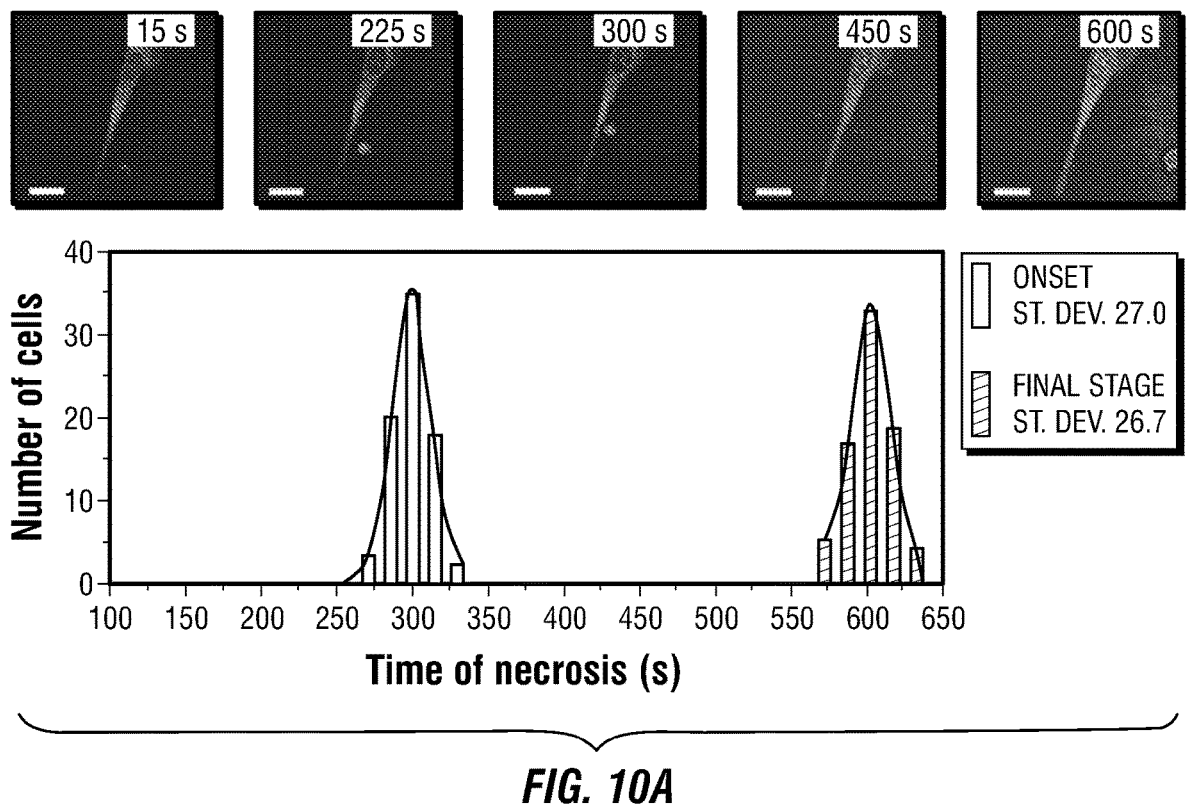
Figure 10B:
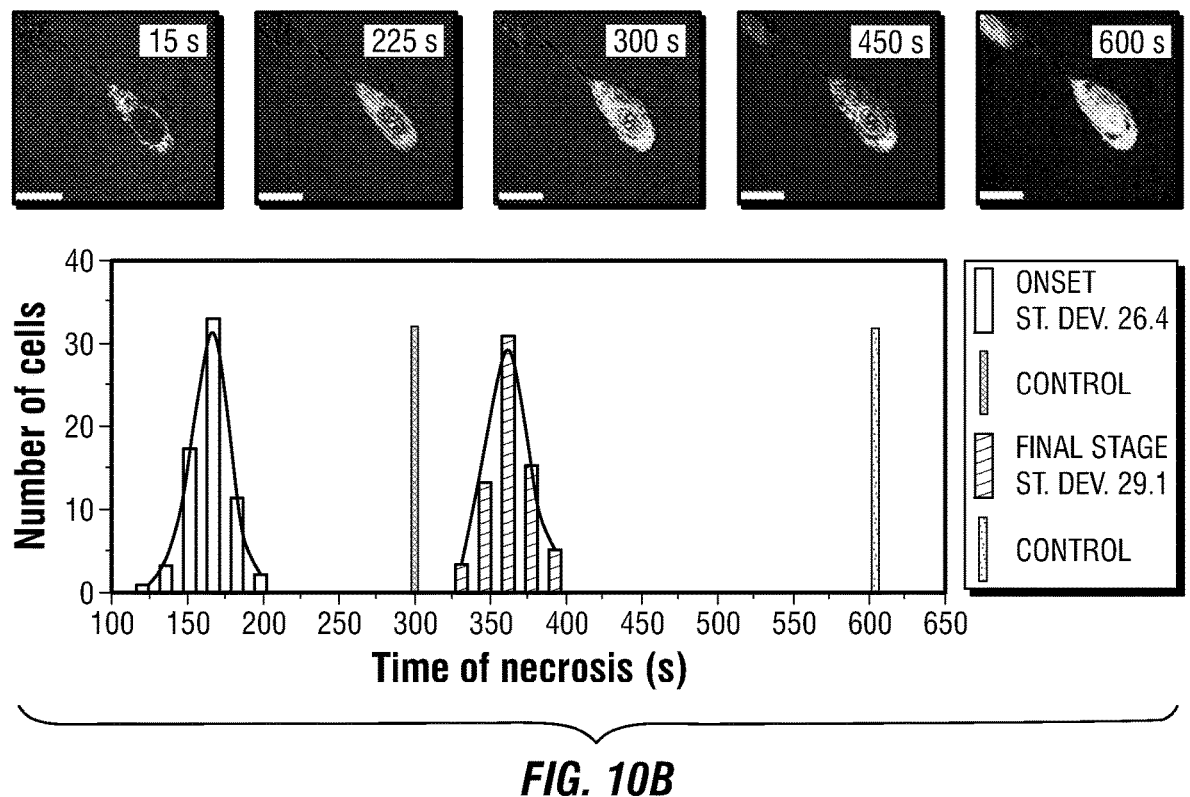
Figure 11B:
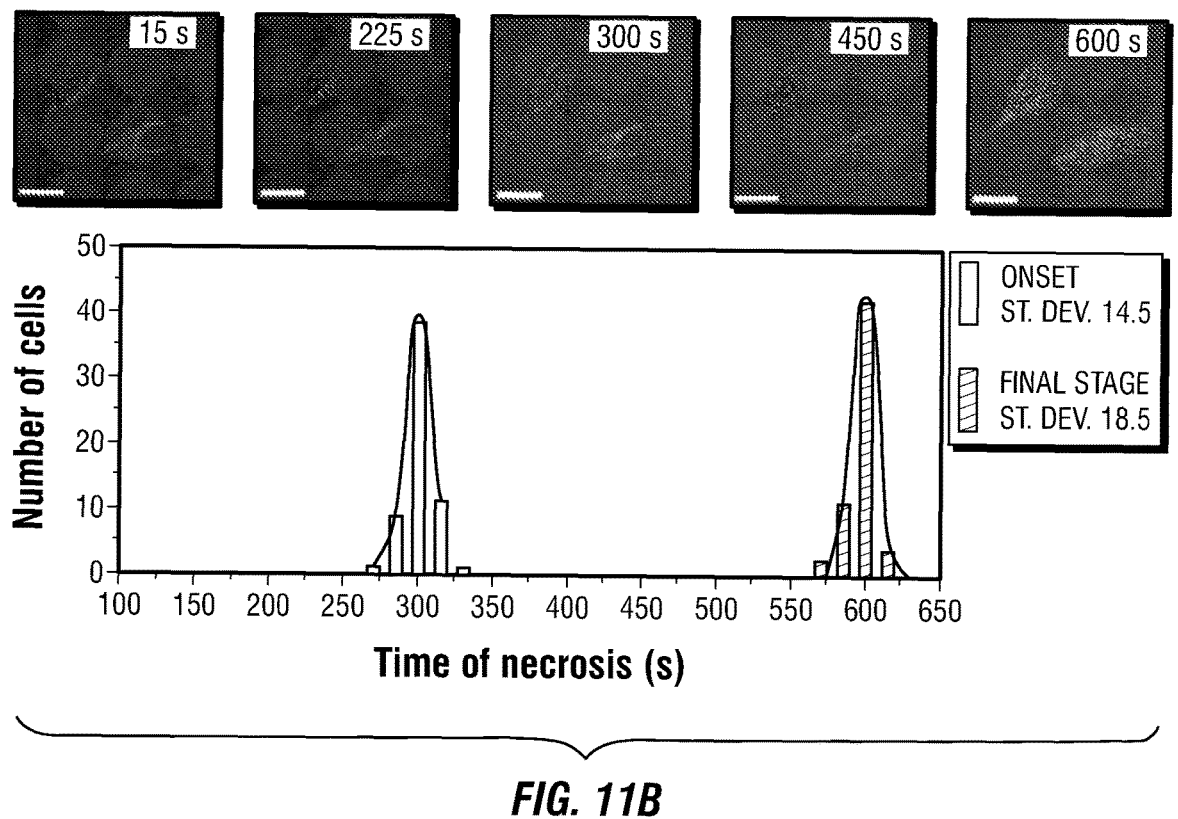
Figure 11C:
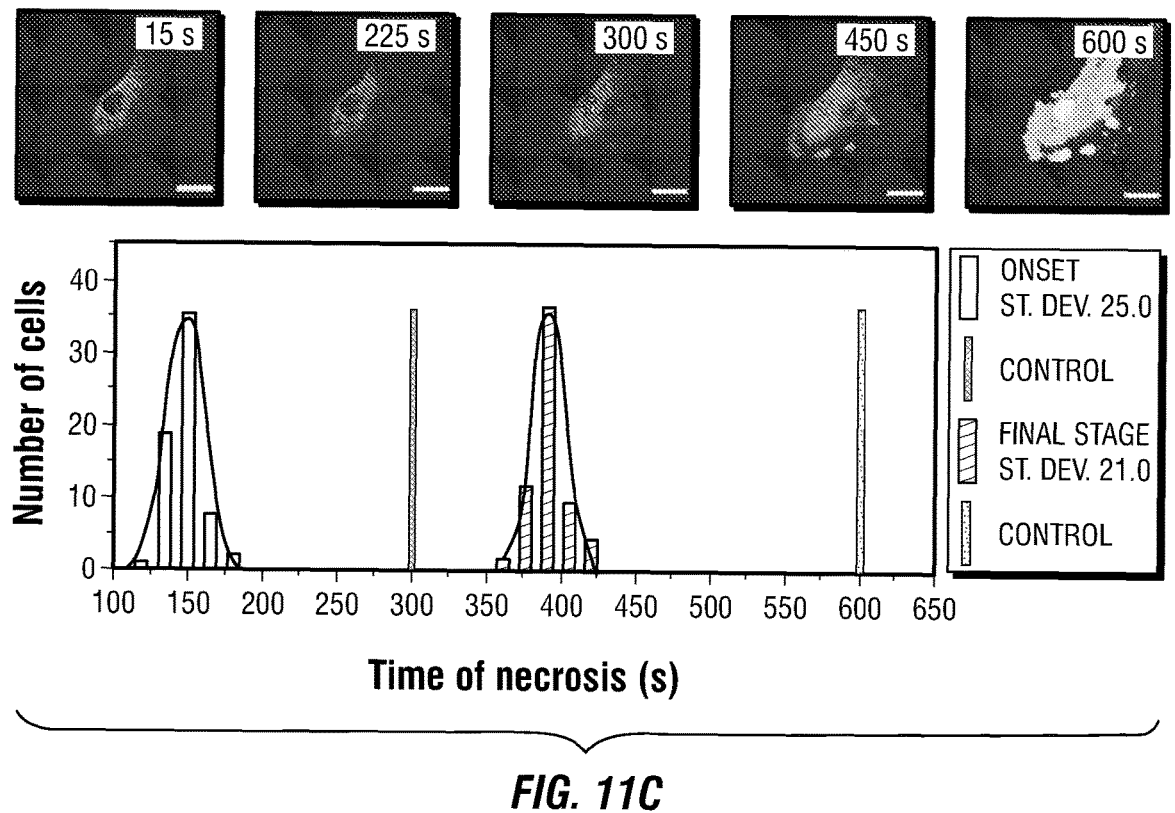
Figure 11D:
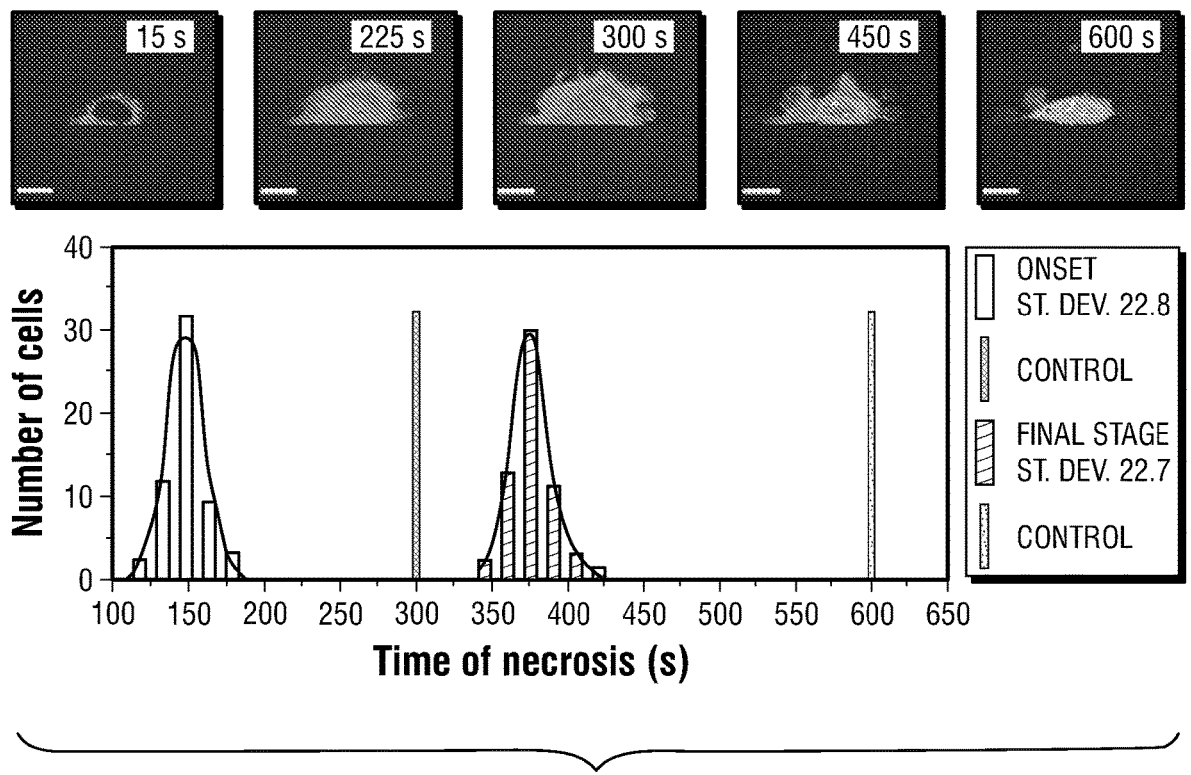
Figure 11E:
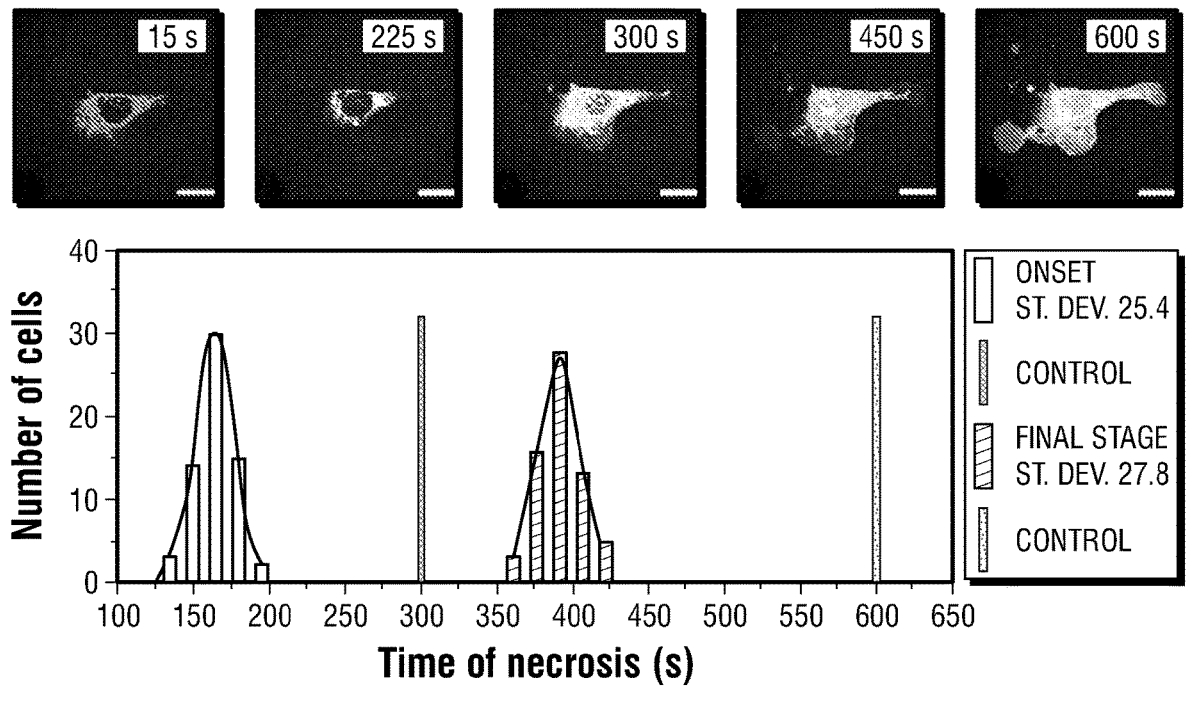
Figure 11F:
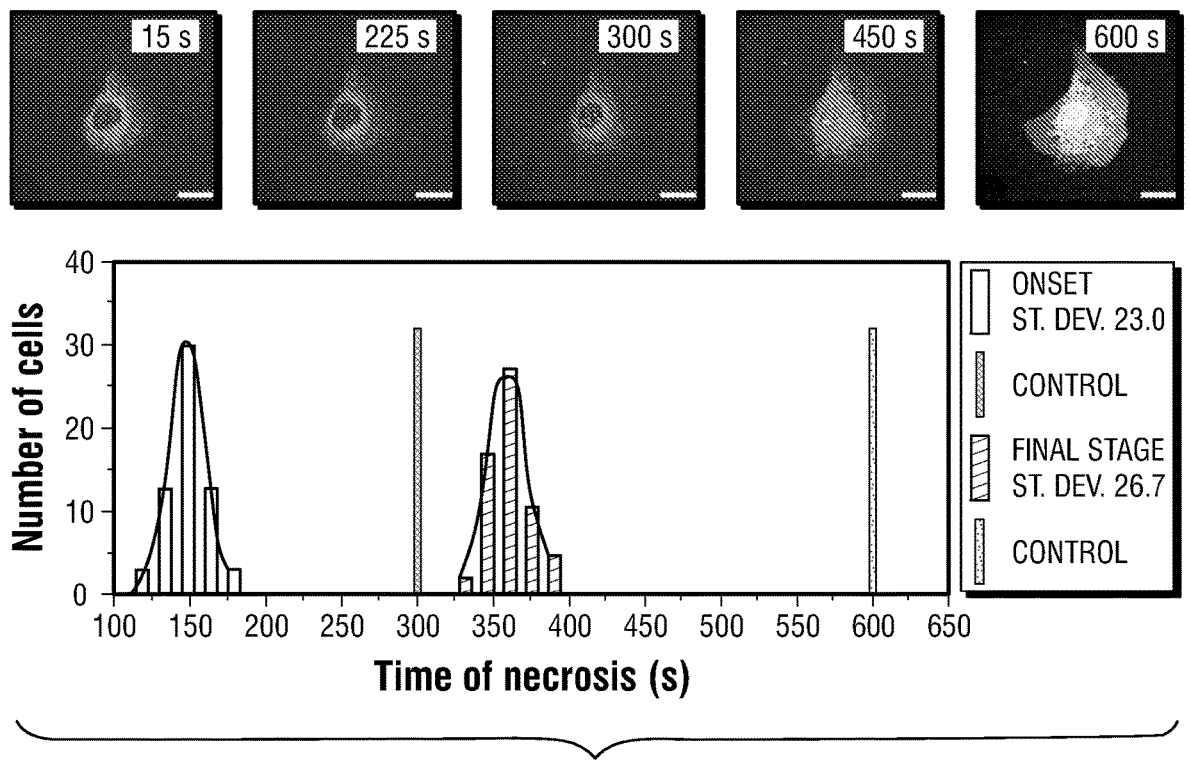
Figure 12A:
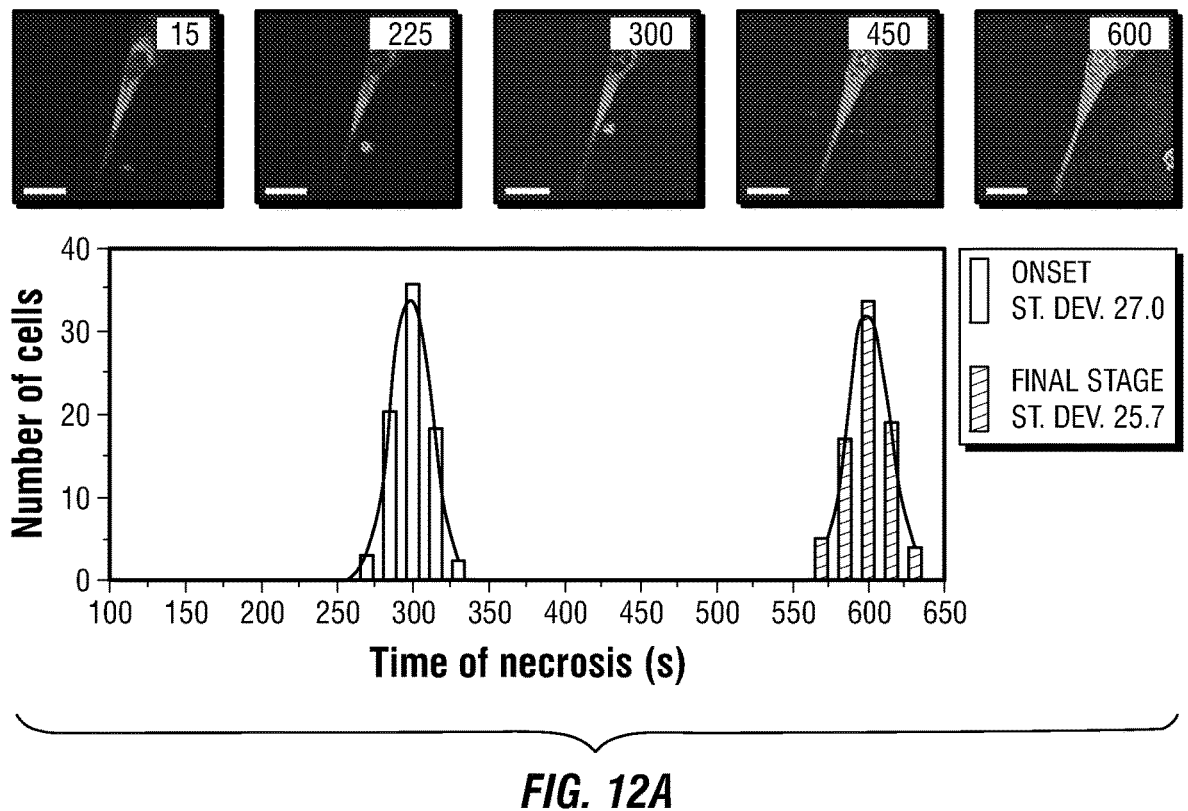
Figure 12B:
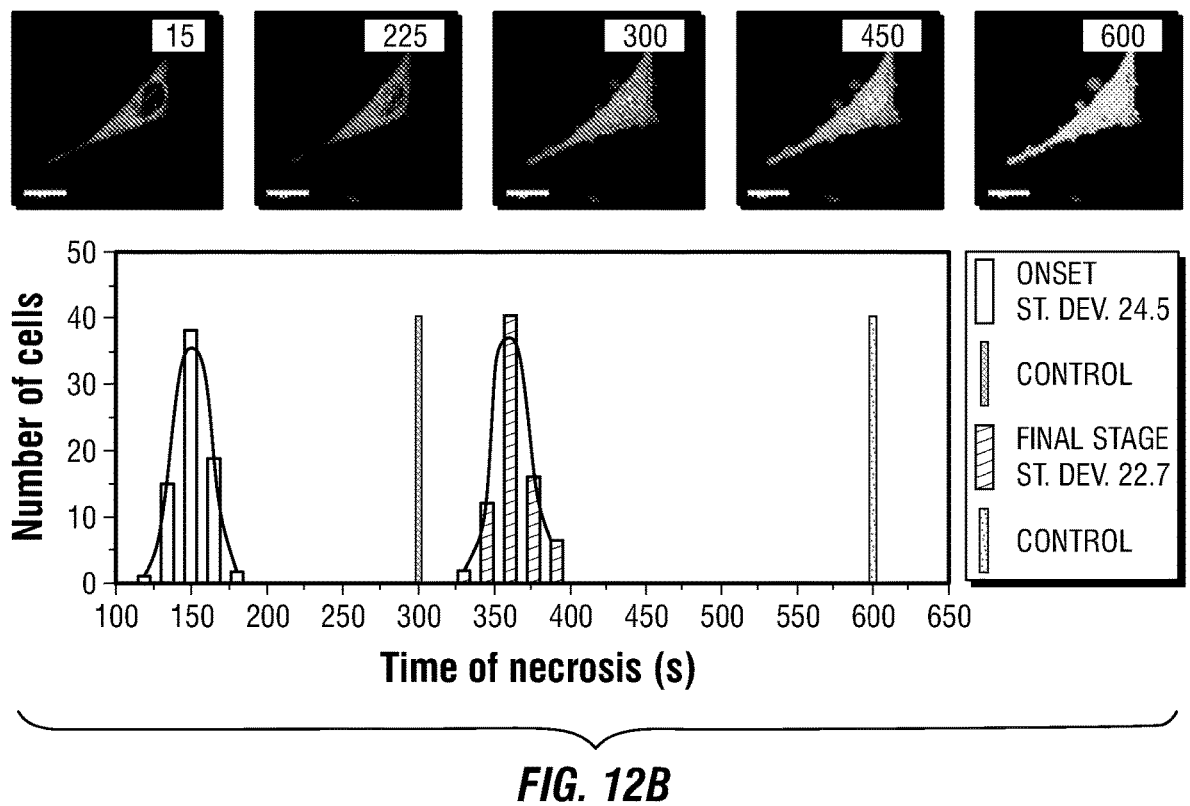
Figure 12C:
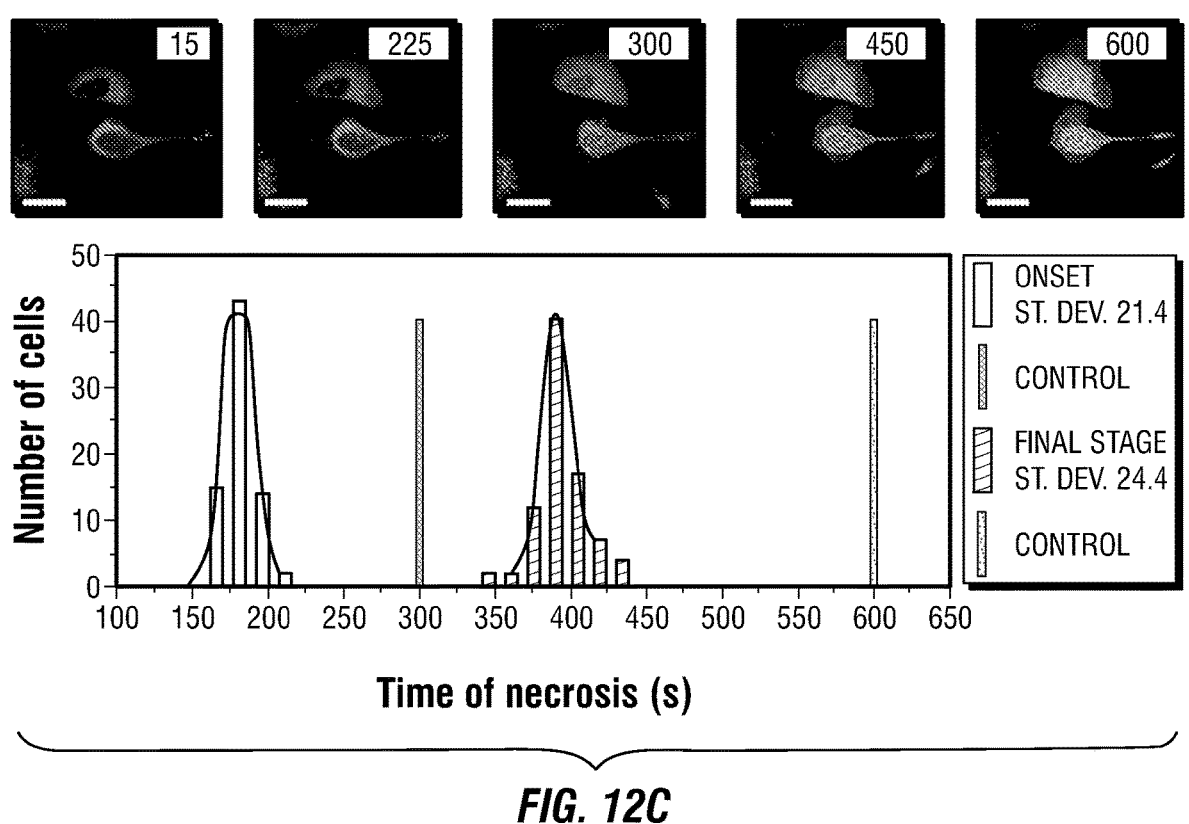
Figure 12D:
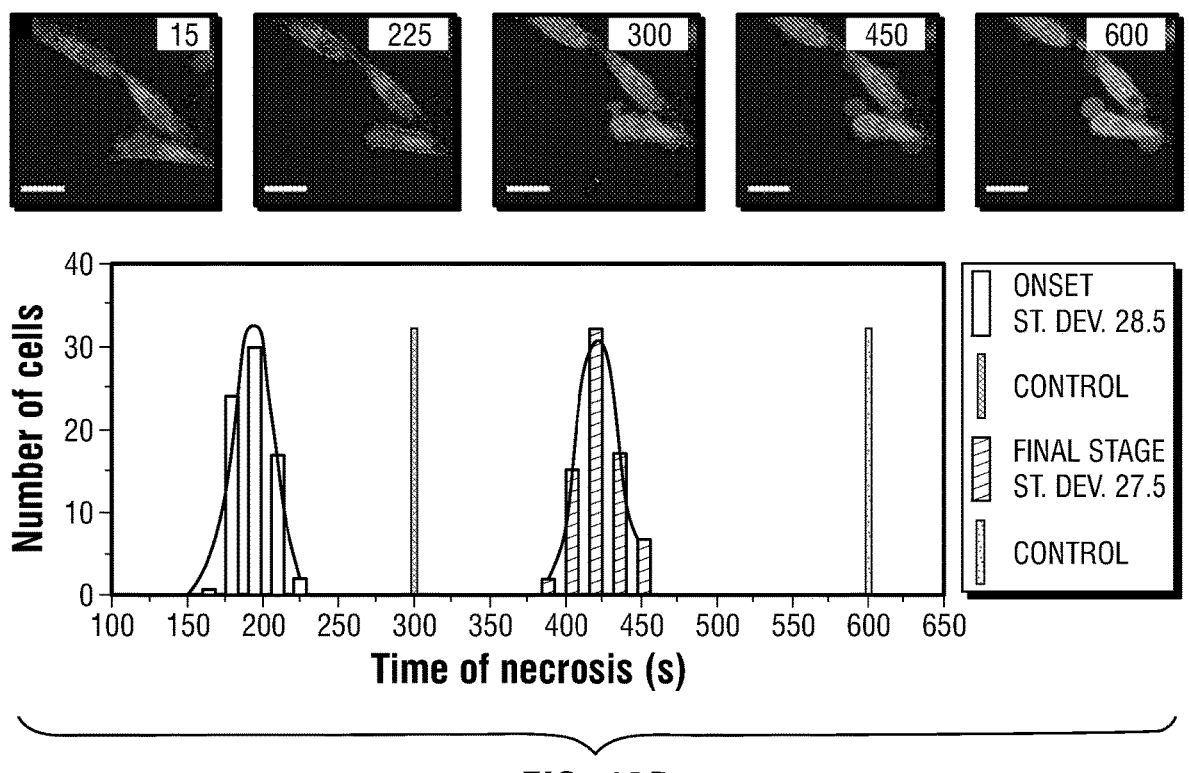
Figure 12E:
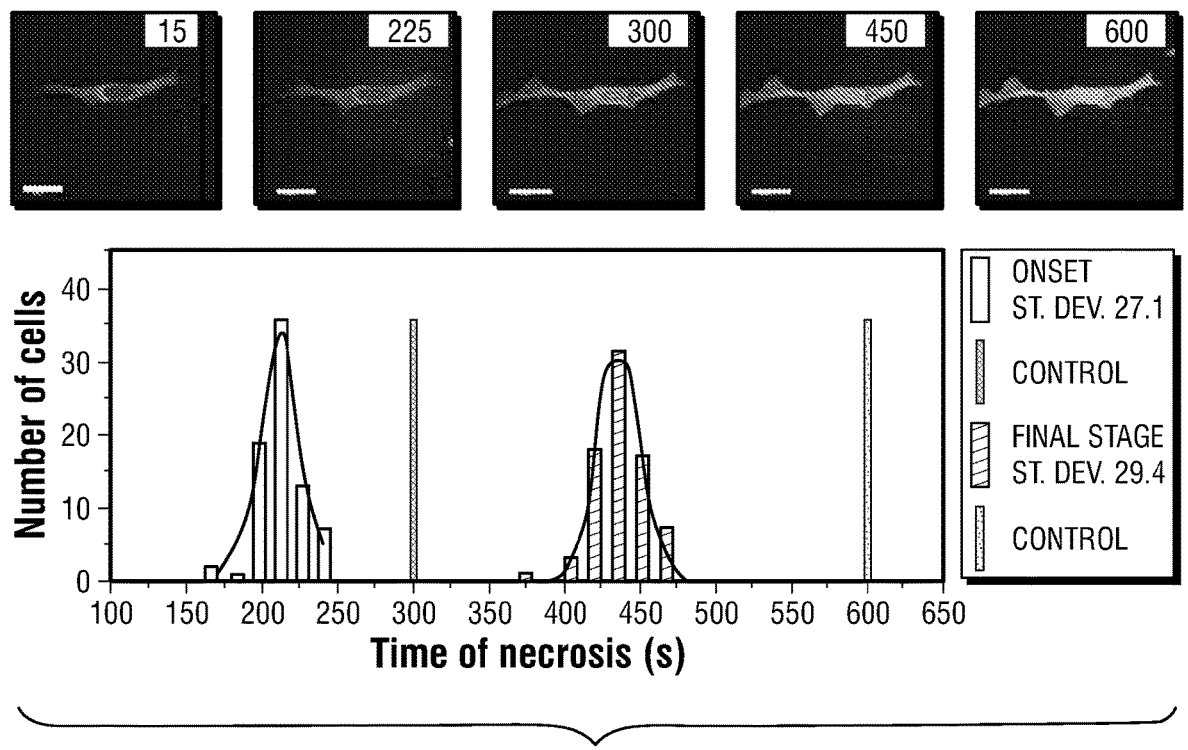
Figure 13A:
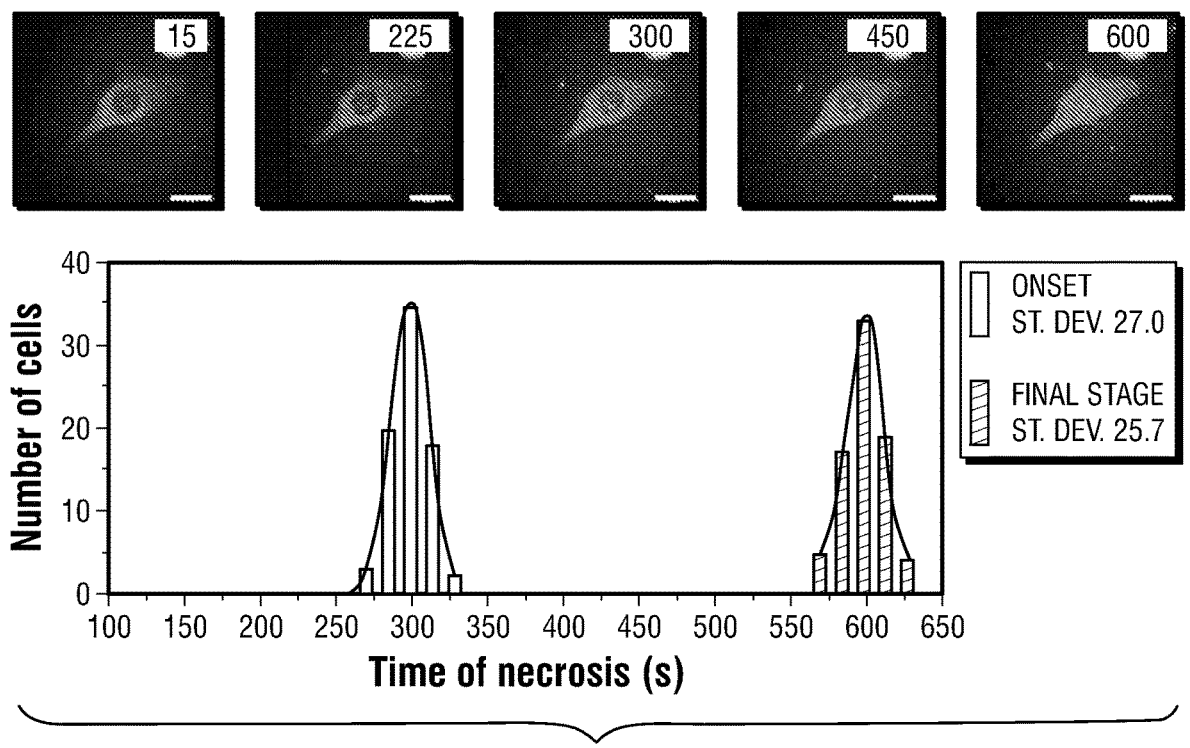
Figure 13B:
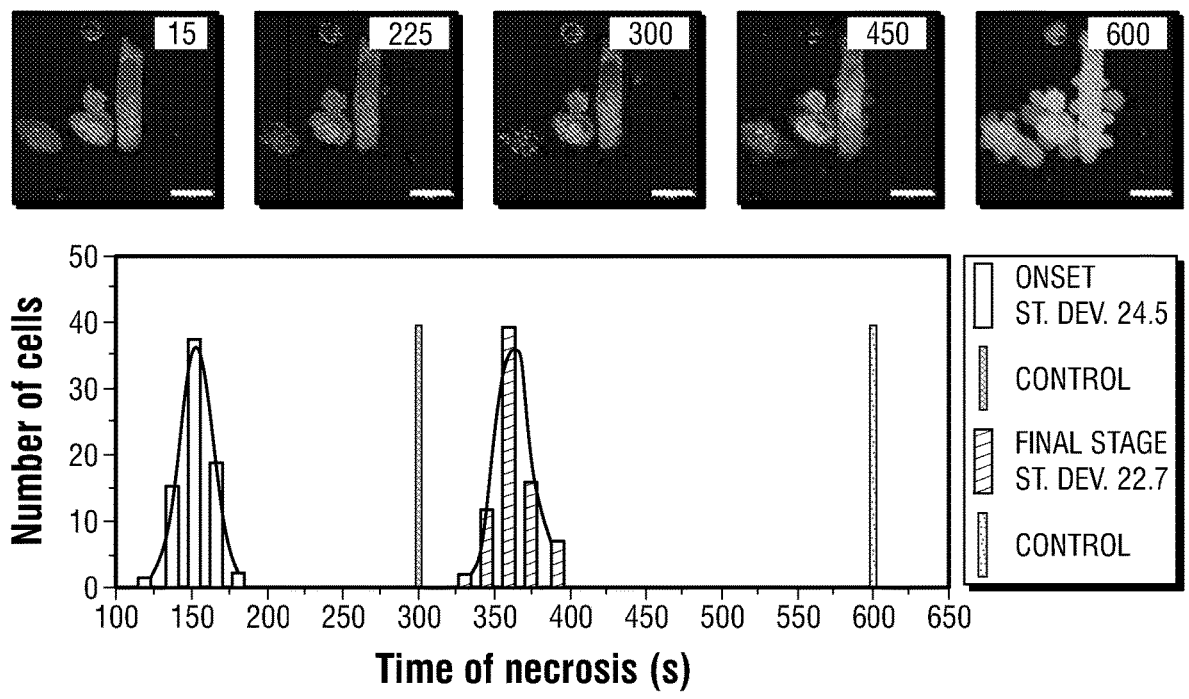
Figure 13C:
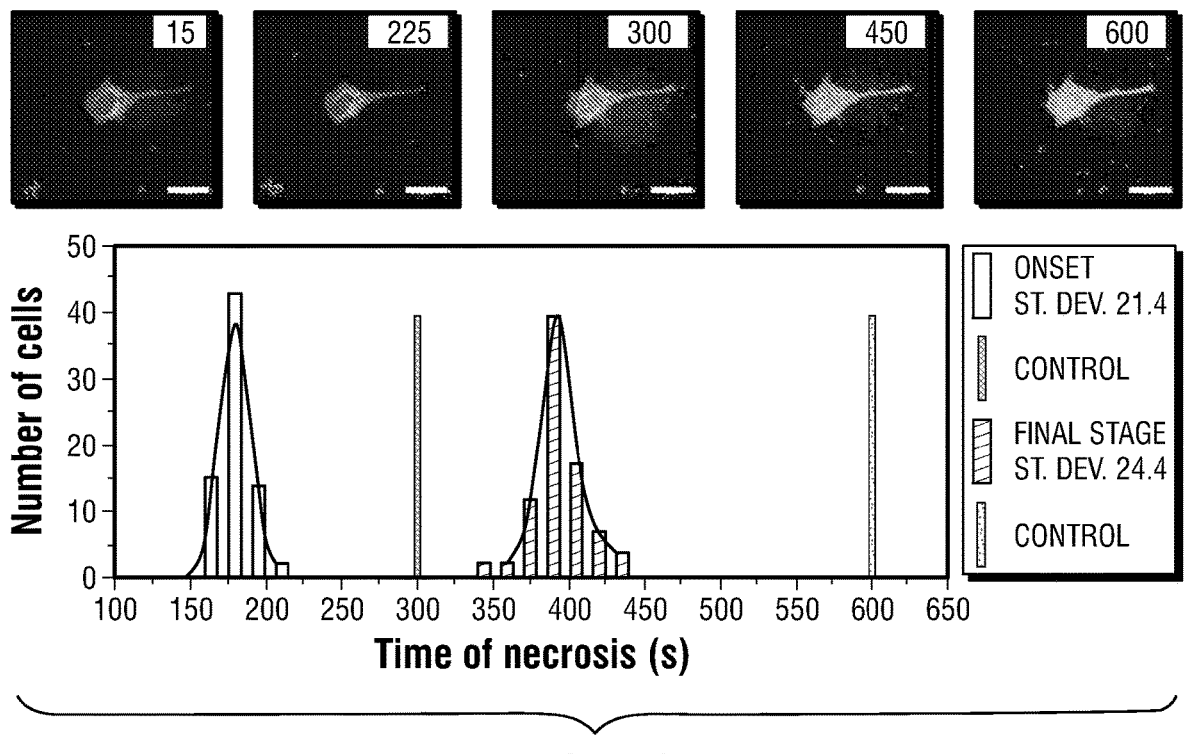
Figure 13D:
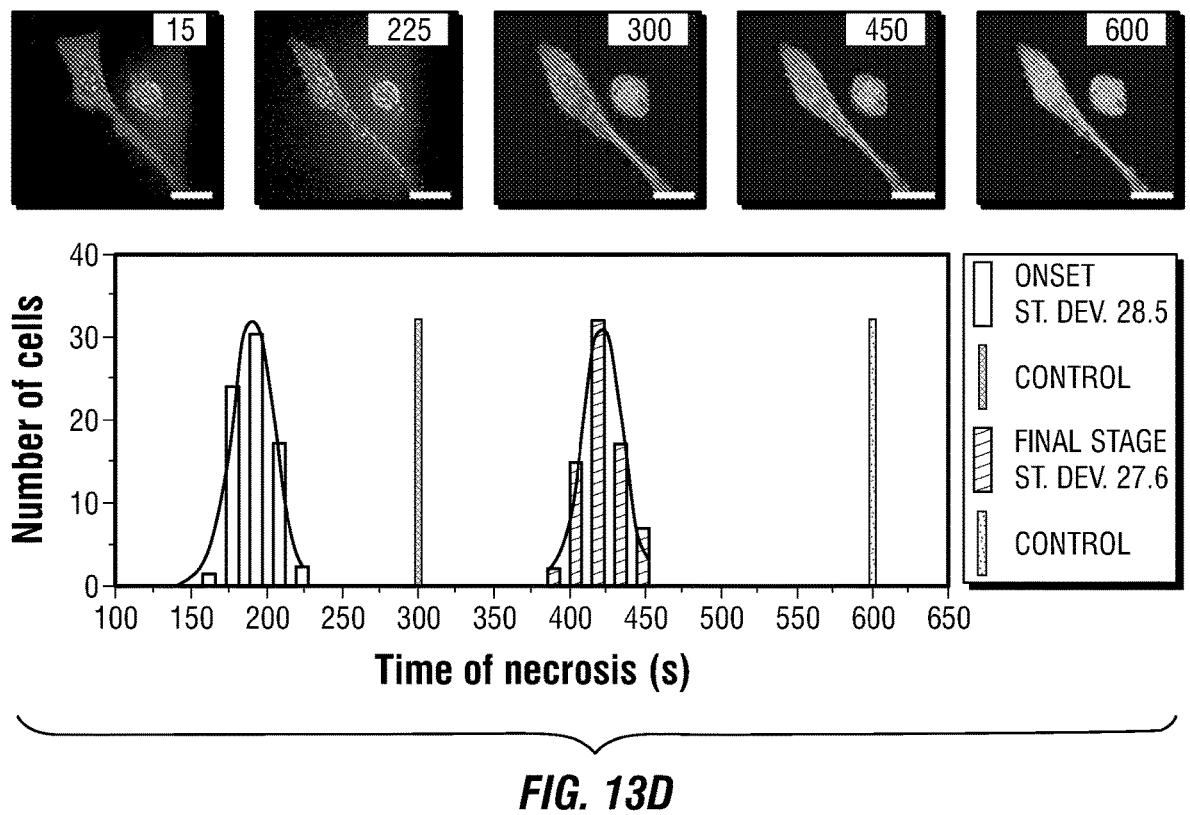
Figure 13E:
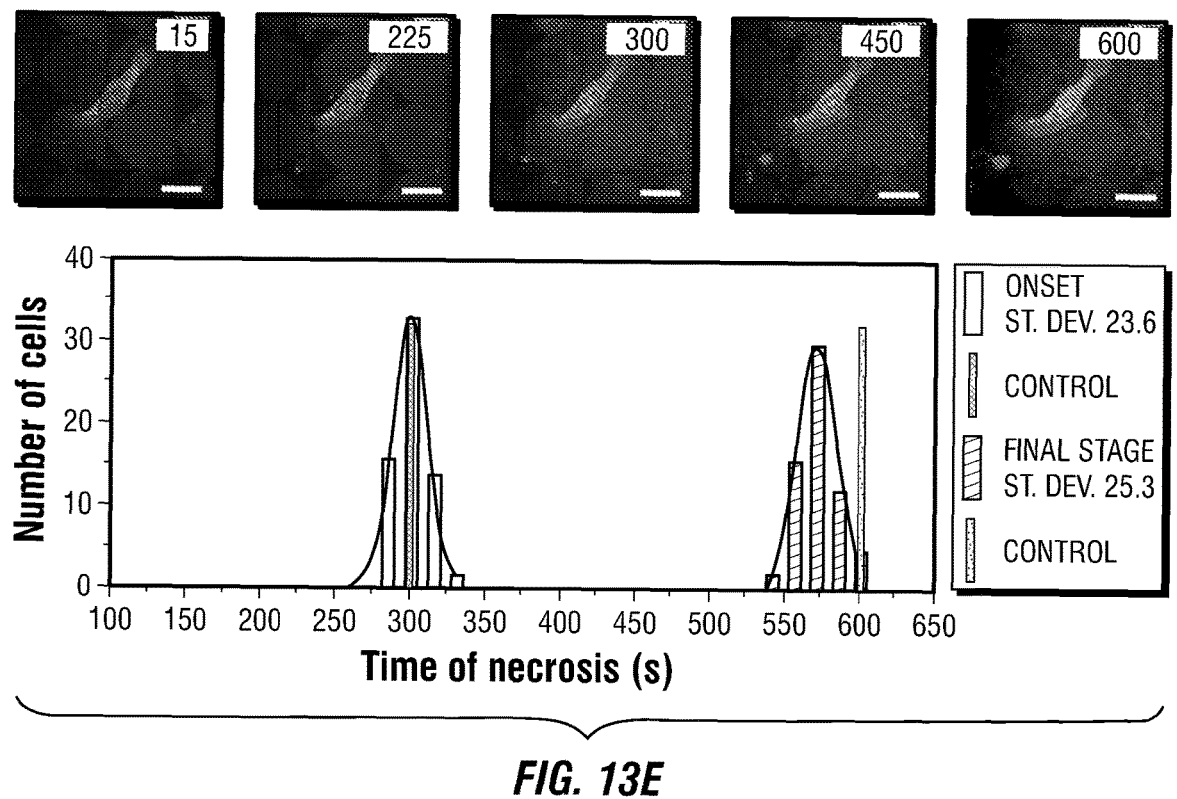
Figure 14A:
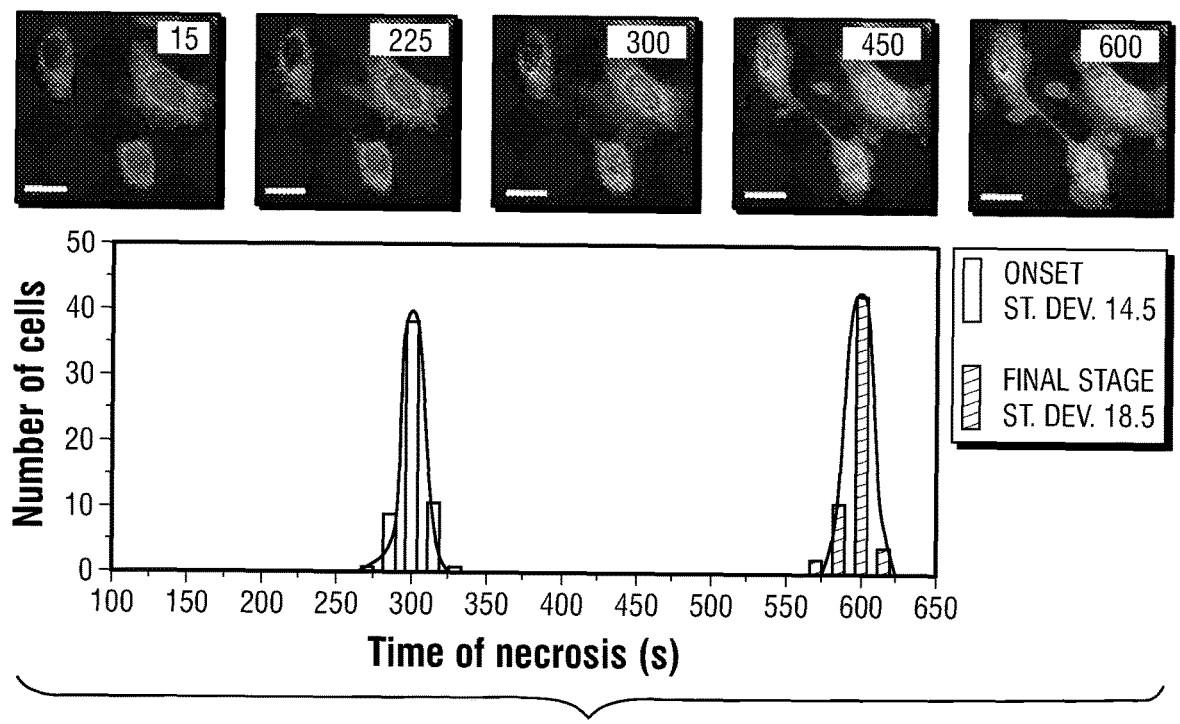
Figure 14B:
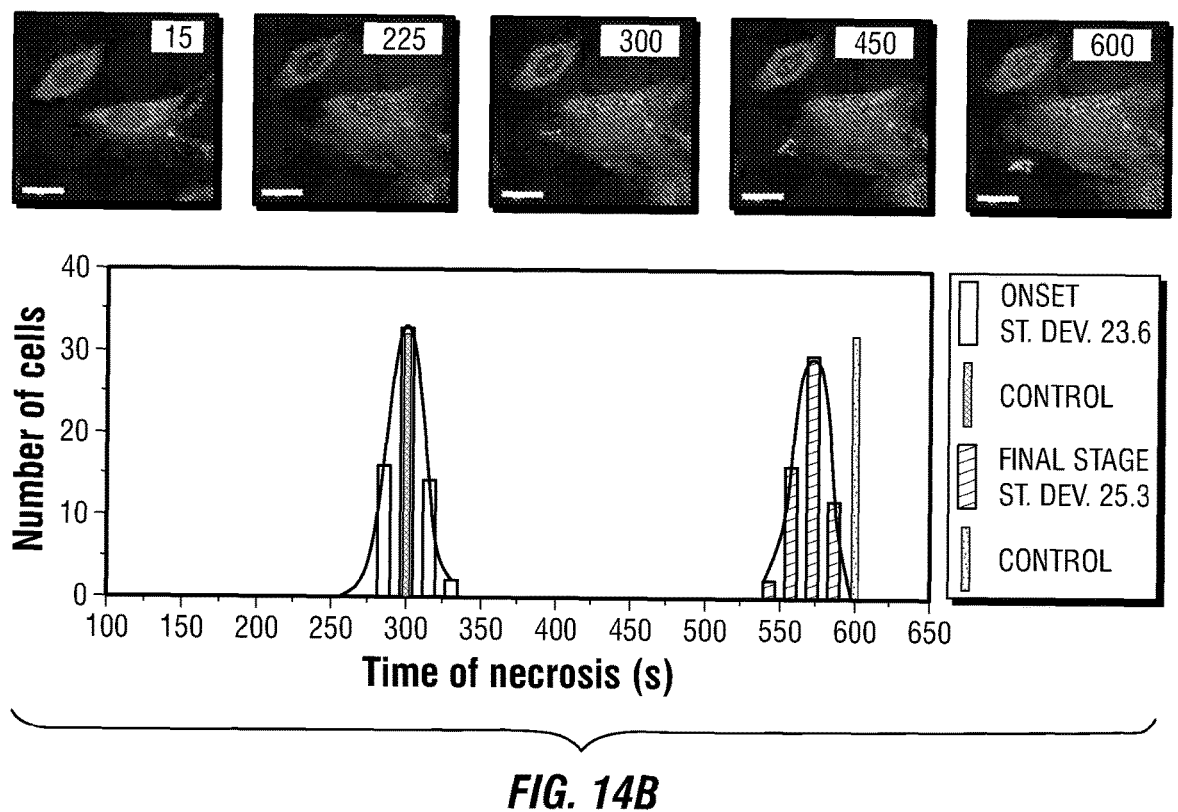
Figure 14C:
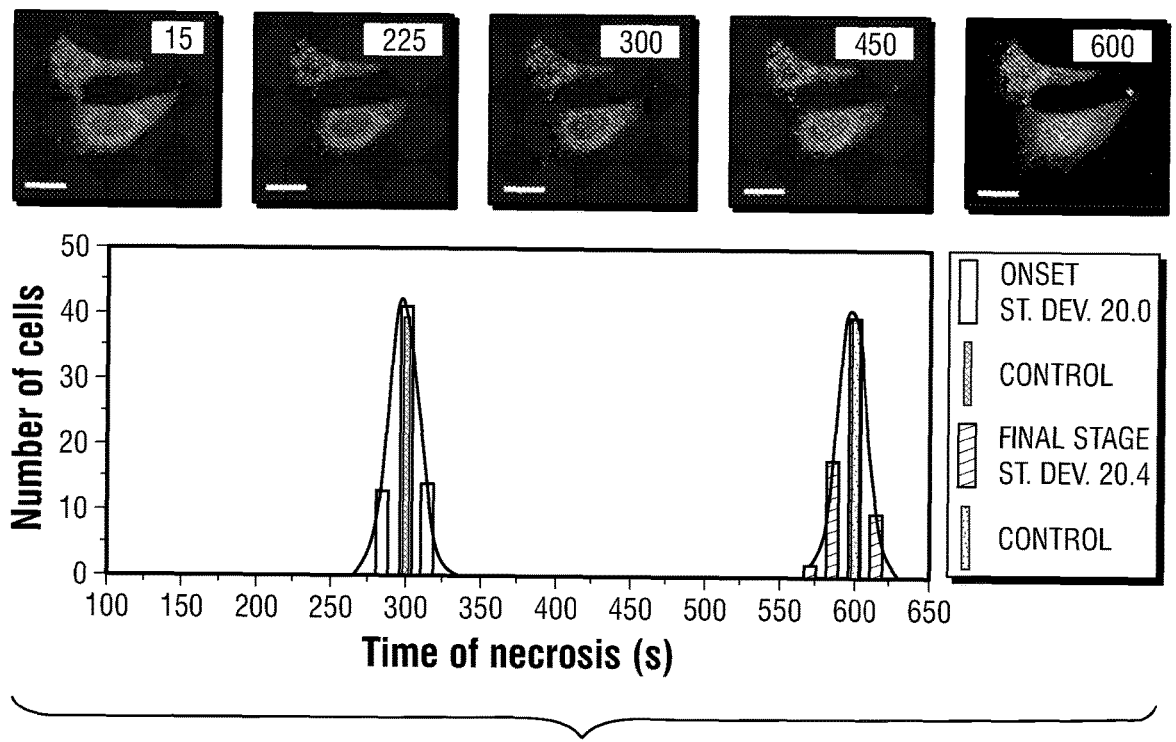
Figure 14D:
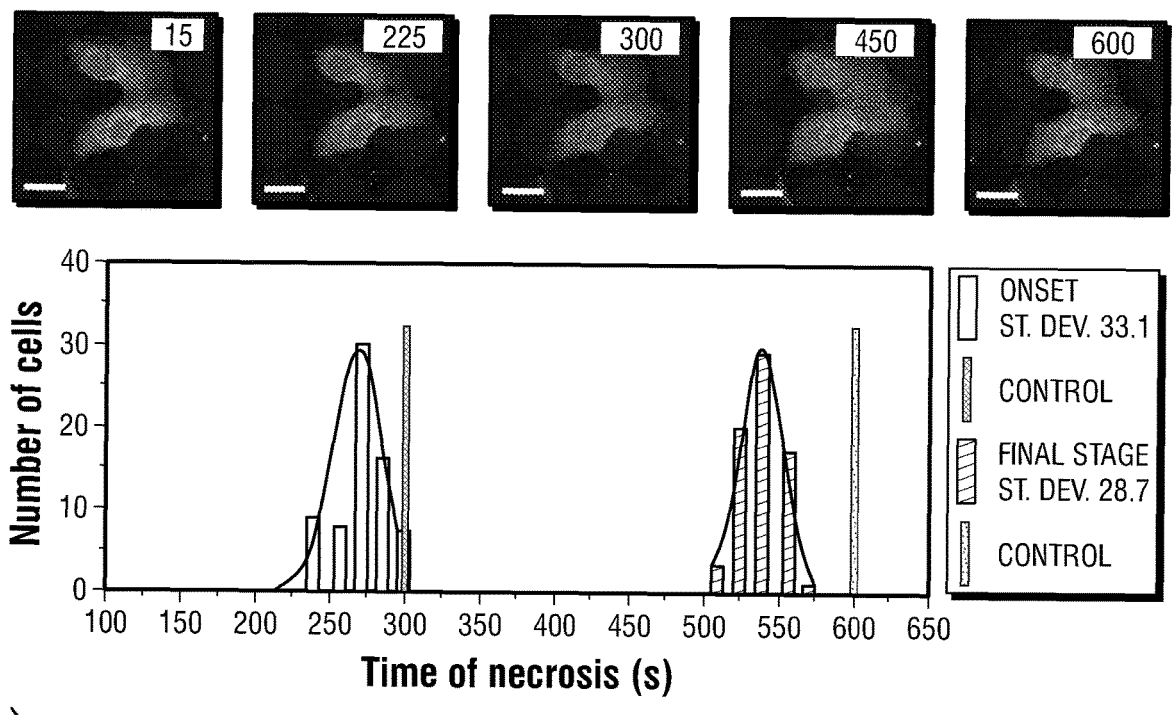
Figure 14E:
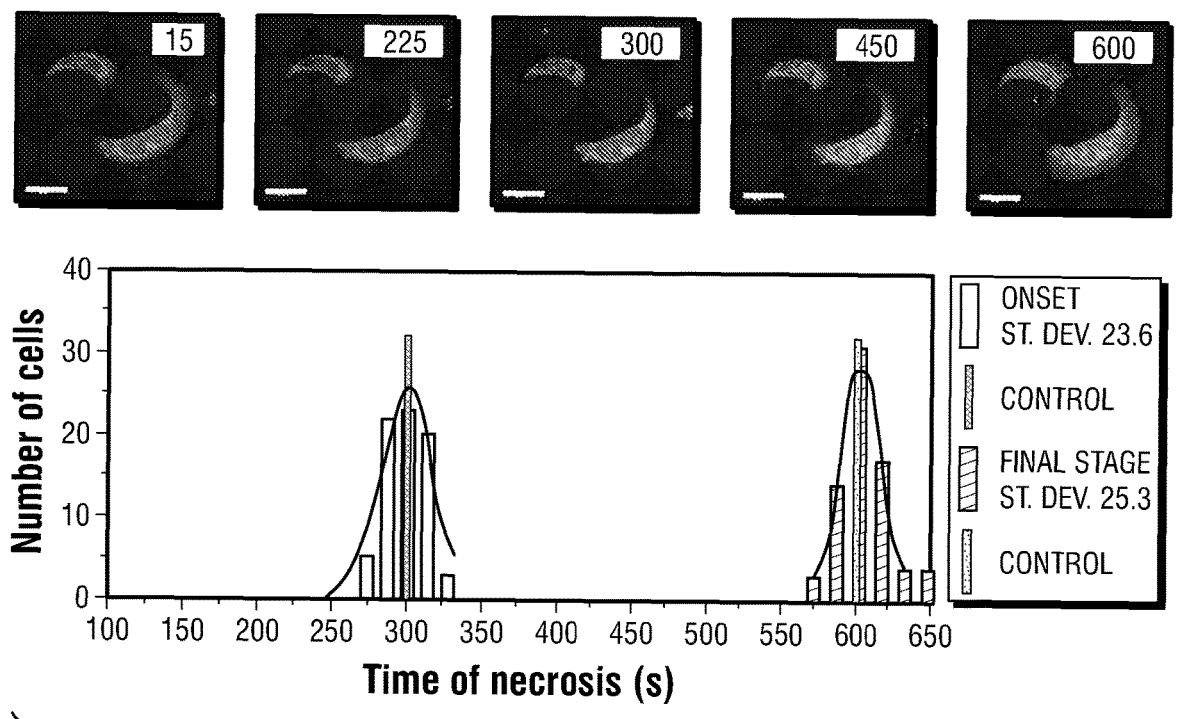
Figure 15A:
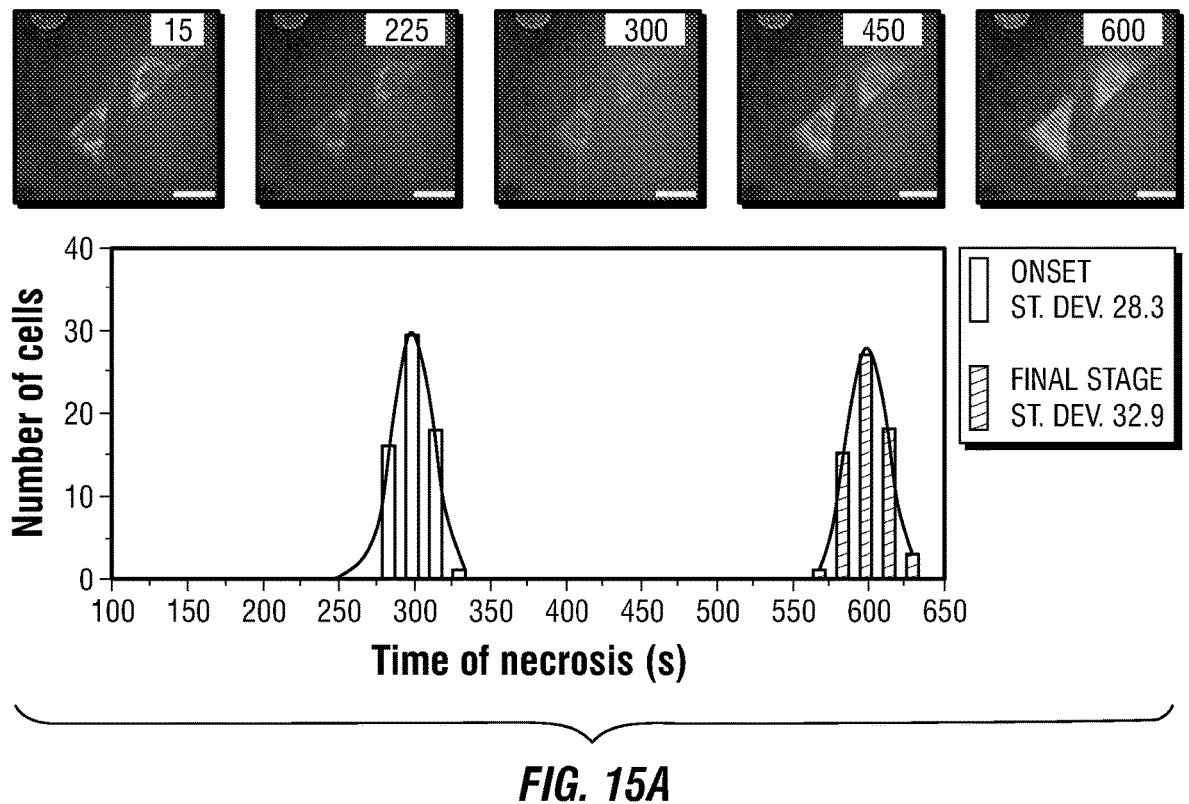
Figure 15B:
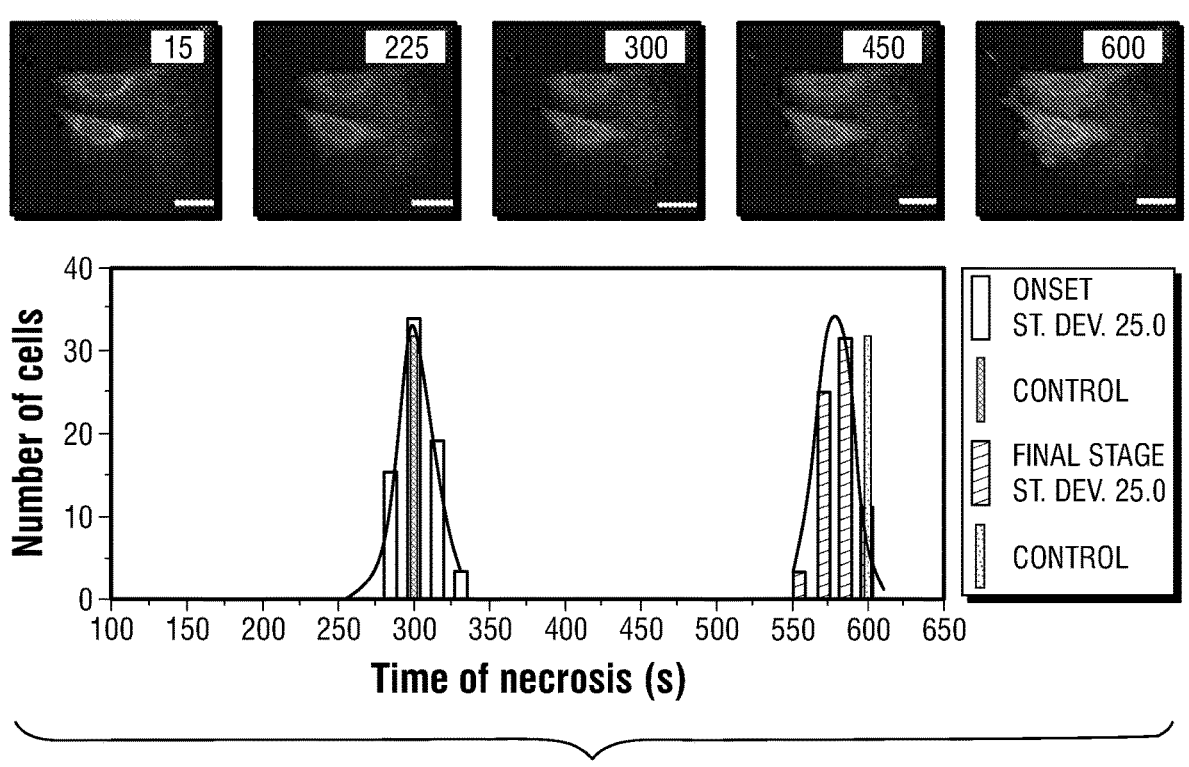
Figure 15C:
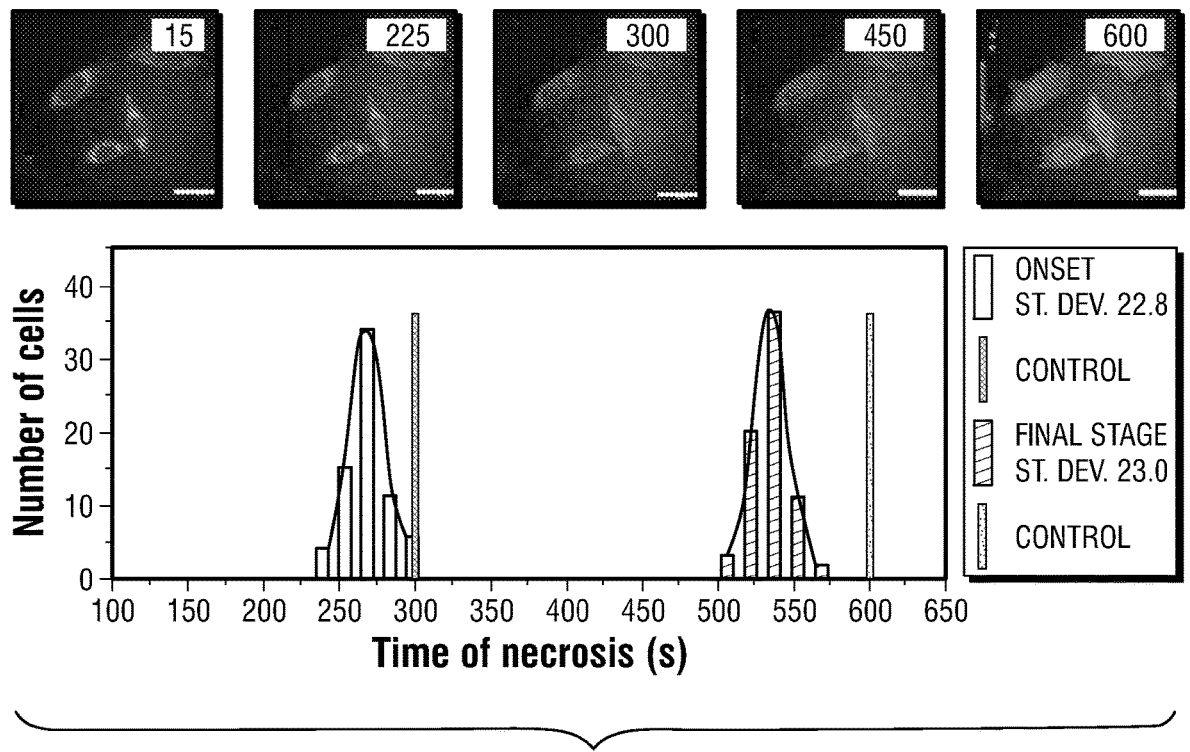
Figure 15D:
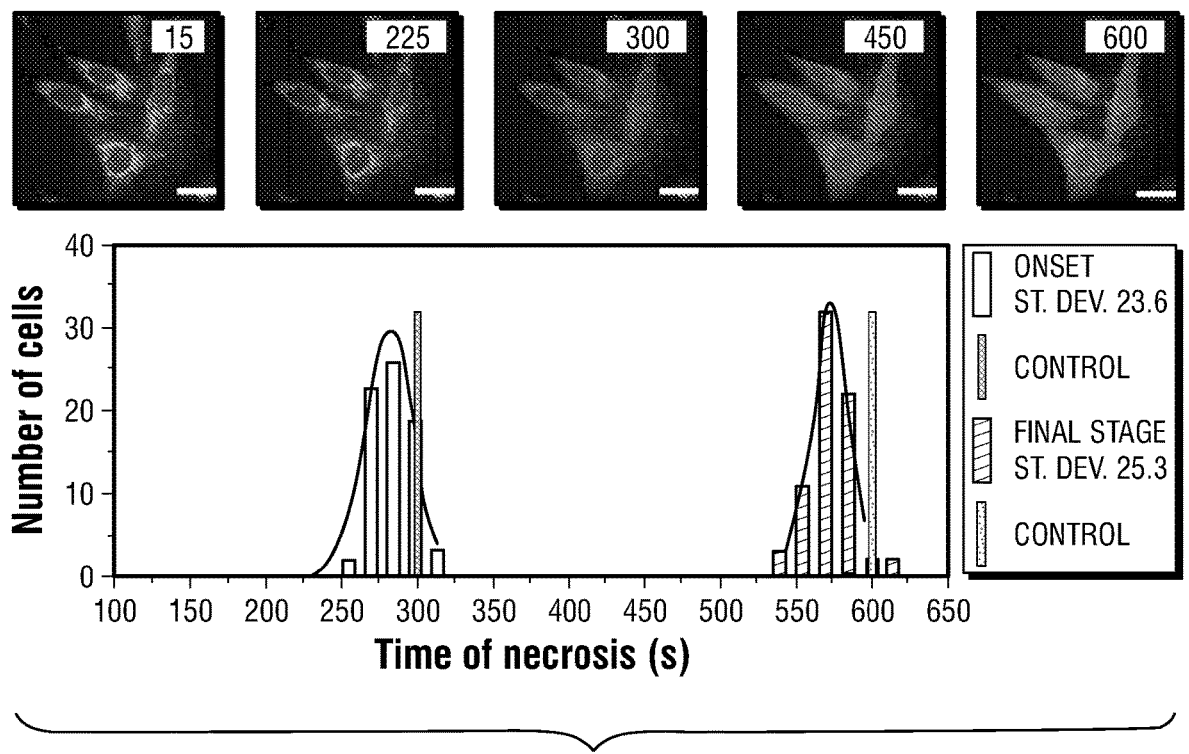
Figure 15E:
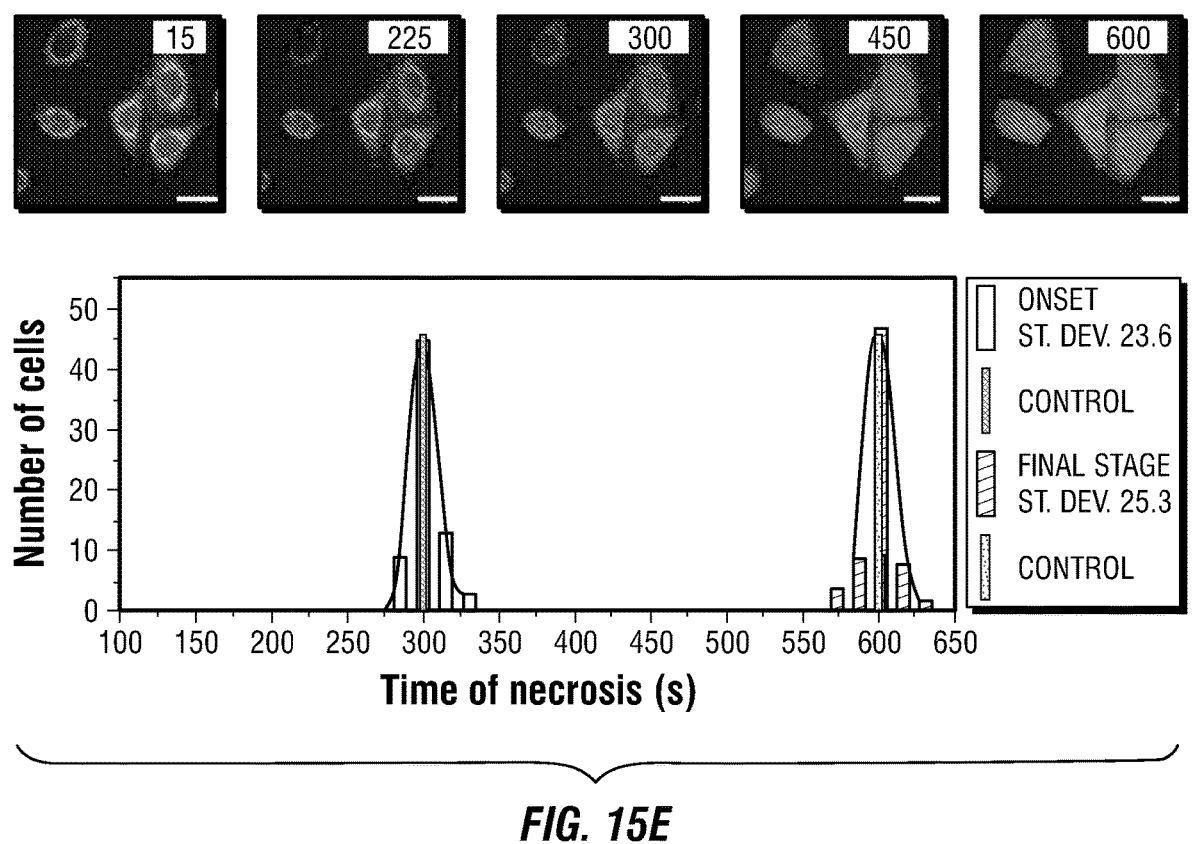

FIG. 10 shows the effects of UV-activated compounds 7 and 8 on PC-3 cells while monitoring necrotic cell death. Recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024×1024 pixel) images of PC-3 cancer cells depict time dependent UV-activated nanomechanical-induced cell morphological changes. PI was added in all the experiments. FIG. 10A shows blank cells without molecular motors. FIG. 10B shows cells with compound 7 before washing. FIG. 10C shows cells with compound 8 before washing. FIG. 10D shows cells with compound 7 after washing. FIG. 10E shows cells with compound 8 after washing. Scale bars are 20 μm. The statistical analyses for each of the live cell microscopy experiments are shown to the right of the images for that row. The determination of onset (orange) and final stage (red) of necrosis are shown combining 4 to 5 individual microscope slides with 5 to 7 FOV on each with an average 2.2 to 3.1 cells per FOV. The displayed standard deviations are calculated from the Gaussian fit and have been rounded up to 15 second integers due to the experimentally predefined length associated with each scanning sequence. See Table 2 for more details.

FIG. 11 provides data indicating that molecular motors 7 and 8 show an unexpectedly strong association with NIH 3T3 cells during nanomechanical-induced necrosis. UV-activated nanomechanical-accelerated necrosis by compounds 7 and 8 occurred in the same timeframe as with the PC-3 cells, indicating no desired selectivity of PC-3 over the NIH 3T3 cells studied in this Figure. Shown are recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024× 1024 pixel) images of NIH 3T3 cancer cells depicting time dependent UV-activated nanomechanical-induced cell morphological changes. PI was added in all experiments. FIG. 11A shows cells with compound 3. FIG. 11B shows blank cells without nanomachines. FIG. 11C shows cells with compound 7 before washing. FIG. 11D shows cells with compound 8 before washing. FIG. 11E shows cells with compound 7 after washing. FIG. 11F shows cells with compound 8 after washing. Scale bars are 20 µm. The statistical analyses for each of the live cell microscopy experiments are shown to the right of the images for that row. The determination of onset (orange) and final stage (red) of necrosis are shown by combining 4 to 6 individual microscope slides with 5 to 7 FOV on each with an average 2.2 to 2.6 cells per FOV. The displayed standard deviations are calculated from the Gaussian fit and have been rounded up to 15 second integers due to the experimentally predefined length associated with each scanning sequence. See Table 2 for more details.

FIG. 12 shows the study of targeted nanomechanical action of compounds 9 and 10 upon PC-3 cell necrosis. Shown are recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024×1024 pixel) images of PC-3 human prostate cancer cells depicting time-dependent UV-activated nanomechanical-induced cell morphological changes. PI was added to all the cell media. The UV-exposure times are shown in each image. FIG. 12A shows blank cells without molecular motors. FIG. 12B shows cells exposed to compound 9 without washing. FIG. 12C shows cells exposed to compound 9 followed by washing. FIG. 12D shows cells exposed to compound 10 without washing. FIG. 12E shows cells exposed to compound 10 followed by washing. All scale bars are 20 µm. The statistical analyses for each of the live cell microscopy experiments are shown to the right of the images for that row. The determination of onset (orange) and final stage (red) of necrosis are shown by combining 5 to 6 individual microscope slides with 5 to 9 FOV on each with an average 2.5 to 3.1 cells per FOV. The displayed standard deviations are calculated from the Gaussian fit and have been rounded up to 15 second integers due to the experimentally predefined length associated with each scanning sequence. See Table 2 for more details.

FIG. 13 shows the study of nanomechanical action of compounds 9 and 10 upon PC-3 (targeted) and NIH 3T3 cells (untargeted) showing that PC-3 cell necrosis occurs faster than NIH 3T3 cell necrosis. Shown are recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024× 1024 pixel) images of cancer cells depicting time-dependent UV-activated nanomechanical-induced cell morphological changes. The UV-activation times are noted in each image and 100 nM PI was in the medium. FIG. 13A shows PC-3 blank cells without motors after 24 hours. FIG. 13B shows PC-3 cells exposed to compound 9 and no washing after 24 hours. FIG. 13C shows PC-3 cells exposed to compound 9, followed by washing, after 24 hours of incubation. FIG. 13D shows PC-3 cells exposed to compound 10 without washing after 24 hours. FIG. 13E shows NIH 3T3 cells exposed to compound 9 without washing after 24 hours. Scale bars are 20 µm. The statistical analyses for each of the live cell microscopy experiments are shown to the right of the images for that row. The determination of onset (orange) and final stage (red) of necrosis are shown by combining 5 to 6 individual microscope slides with 5 to 9 FOV on each with an average 2.5 to 3.1 cells per FOV. The displayed standard deviations are calculated from the Gaussian fit and have been rounded up to 15 second integers due to the experimentally predefined length associated with each scanning sequence. See Table 2 for more details.

FIG. 14 shows the study of the nanomechanical action of compounds 9 and 10 upon NIH 3T3 cells (untargeted) showing little enhanced rate of necrosis. Shown are recorded merged transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024× 1024 pixel) images of NIH 3T3 cells depicting time dependent UV-activated nanomechanical-induced cell morphological changes. The UV-activation times are noted in each image and 100 nM PI was in the medium. FIG. 14A shows blank cells without motors. FIG. 14B shows cells exposed to compound 9 by a 1 hour incubation and no washing. FIG. 14C shows cells exposed to compound 9 by a 1 hour incubation followed by washing. FIG. 14D shows cells exposed to compound 10 by a 1 hour incubation without washing. FIG. 14E shows cells exposed to compound 10 by a 1 hour incubation followed by washing. Scale bars are 20 µm. The statistical analyses for each of the live cell microscopy experiments are shown to the right of the images for that row. The determination of onset (orange) and final stage (red) of necrosis are shown by combining 5 to 6 individual microscope slides with 4 to 6 FOV on each with an average 2.4 to 3.3 cells per FOV. The displayed standard deviations are calculated from the Gaussian fit and have been rounded up to 15 second integers due to the experimentally predefined length associated with each scanning sequence. See Table 2 for more details.

FIG. 15 shows the study of nanomechanical action of compounds 9 and 10 upon CHO cells (untargeted) showing little enhanced necrosis. Shown are recorded transmission (458 nm, 0.2 mW) and UV-induced mitochondrial auto-fluorescence (green, $\lambda_{ex}$ 355 nm, $\lambda_{em}$ 460-550 nm, 20 mW 400 nJ/voxel total dwell time, 1024×1024 pixel) images of the study of compounds 9 and 10 in CHO cells depicting time dependent UV-activated nanomechanical-induced cell morphological changes. The UV-activation times are noted in each image and 100 nM PI was in the medium. FIG. 15A shows blank cells. FIG. 15B shows cells exposed to compound 9 without washing. FIG. 15C shows cells exposed to compound 10 without washing. FIG. 15D shows cells exposed to compound 9 by 30 minutes of incubation with cells after washing. FIG. 15E shows cells exposed to compound 9 with 24 hours of incubation followed by washing of cells. Scale bars are 20 µm. The statistical analyses for each of the live cell microscopy experiments are shown to the right of the images for that row. The determination of onset (orange) and final stage (red) of necrosis are shown by combining 3 to 5 individual microscope slides with 5 to 9 FOV on each with an average 2.5 to 3.2 cells per FOV. The displayed standard deviations are calculated from the Gaussian fit and have been rounded up to 15 second integers due to the experimentally predefined length associated with each scanning sequence. See Table 2 for more details.

Figure 16A:
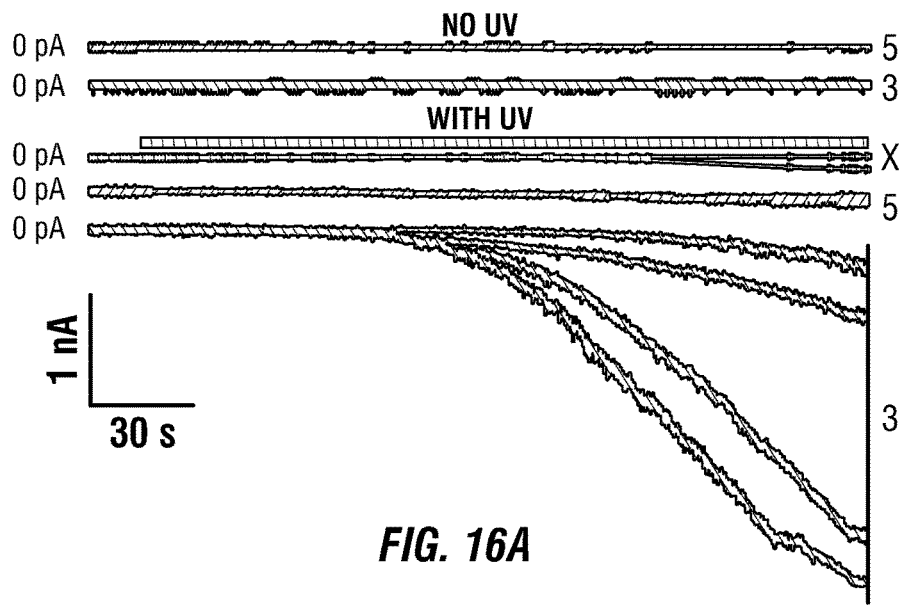
Figure 16B:
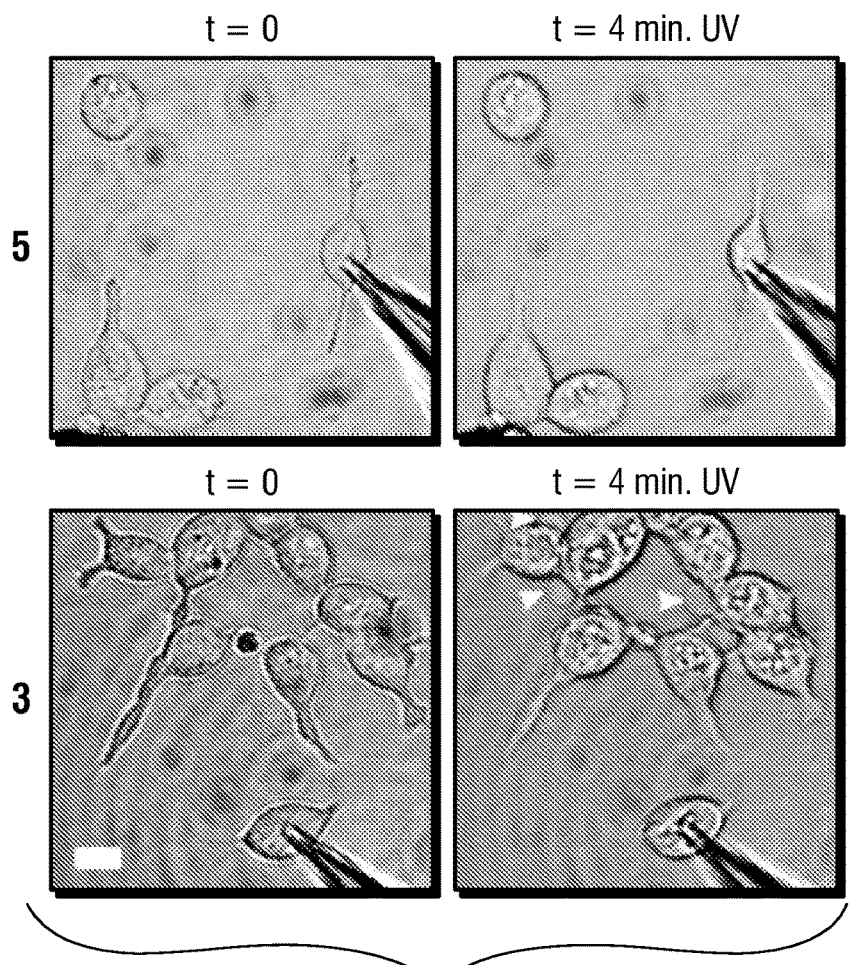
Figure 17A:
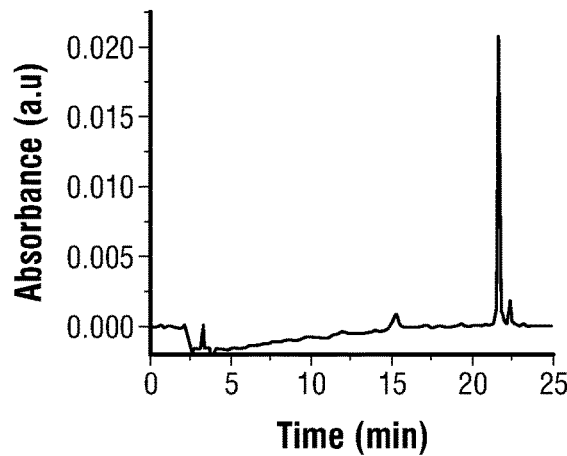
Figure 17B:
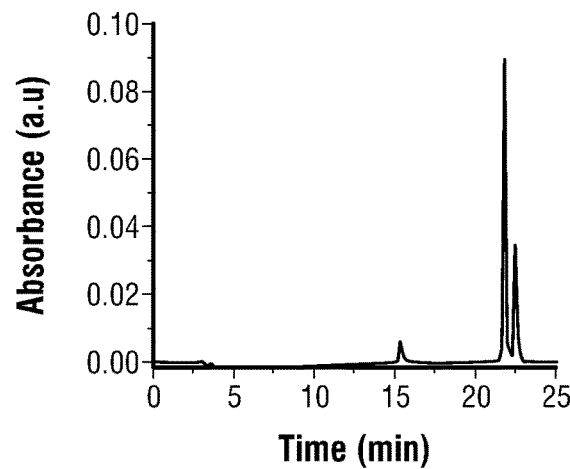
Figure 17C:
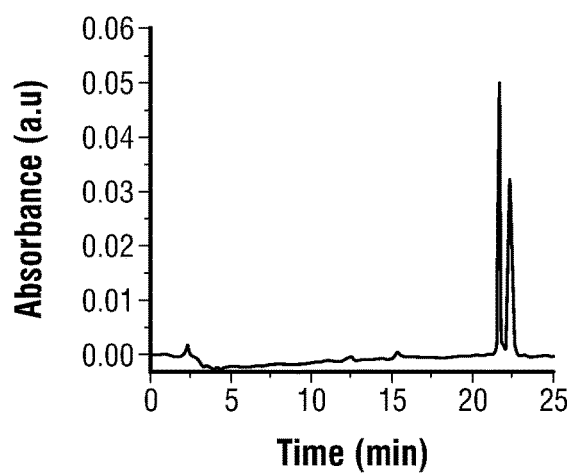
Figure 17D:
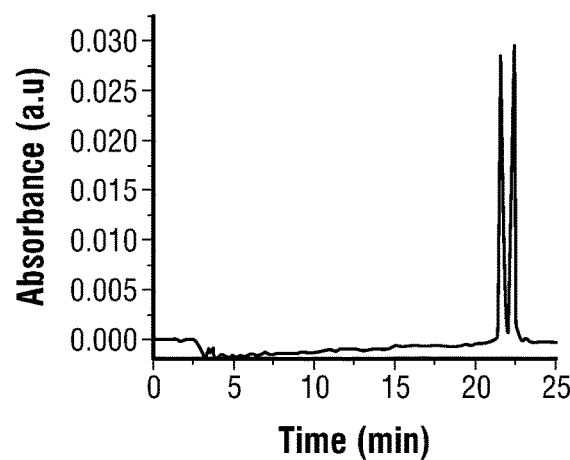
Figure 20A:
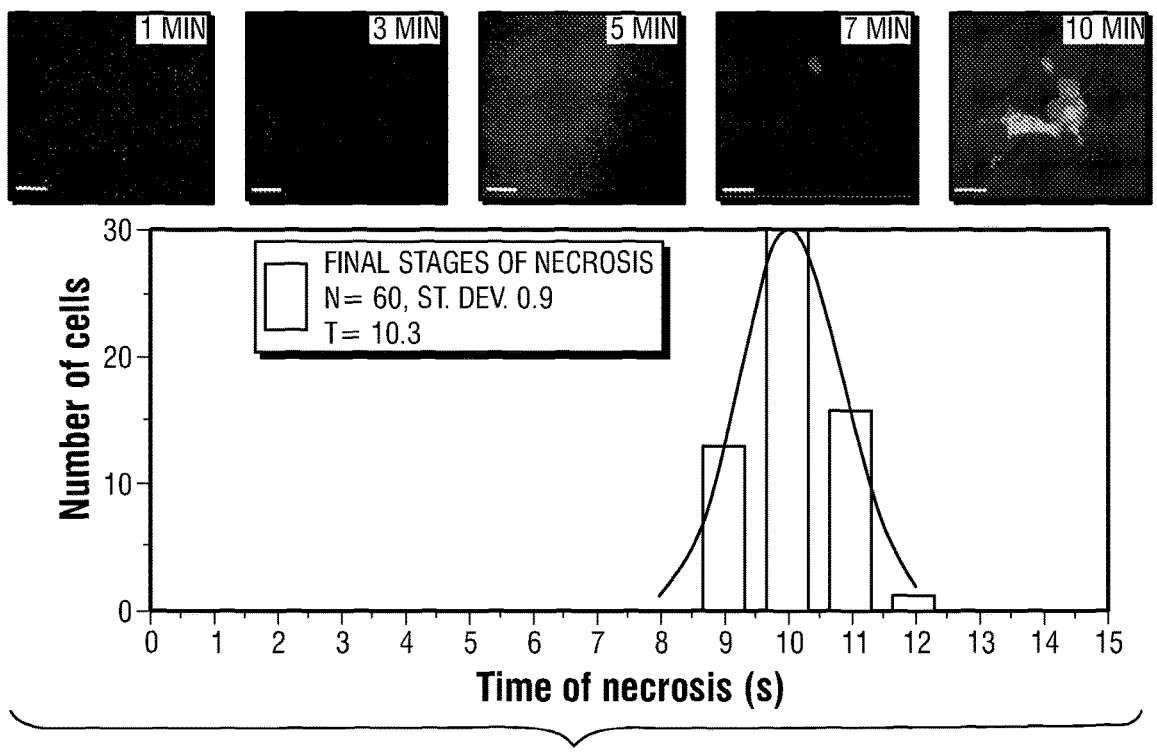
Figure 20B:
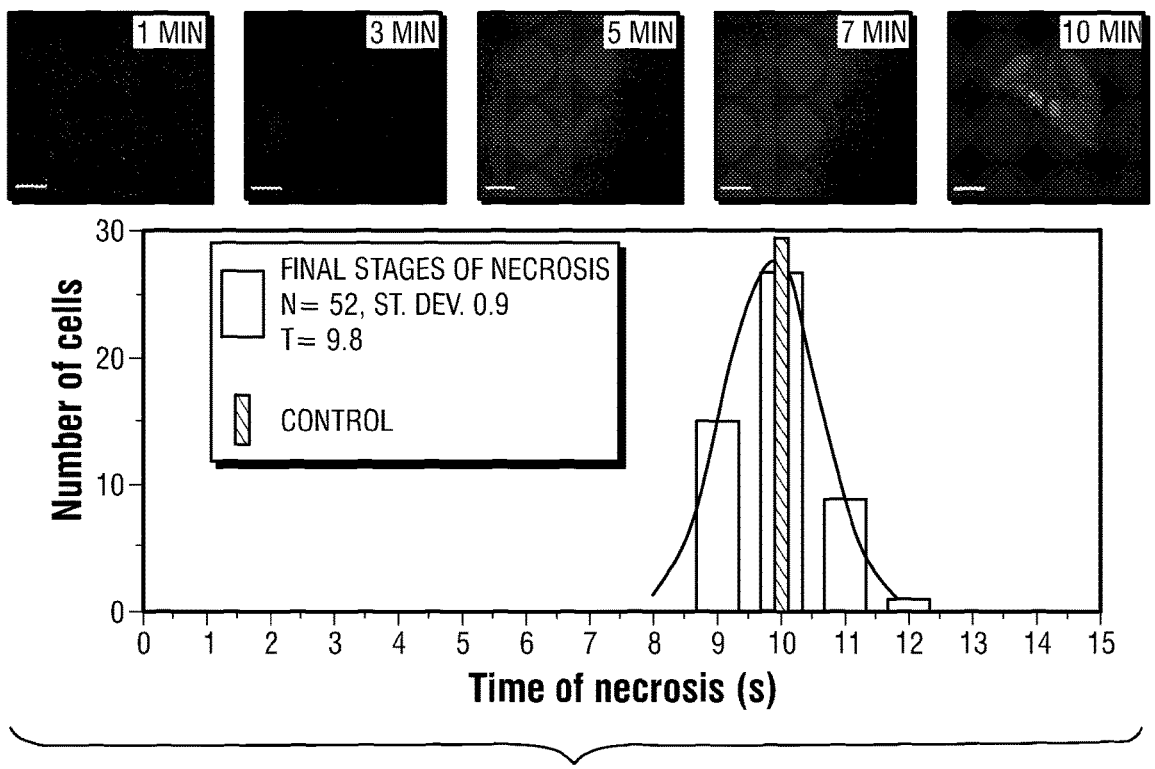
Figure 20C:
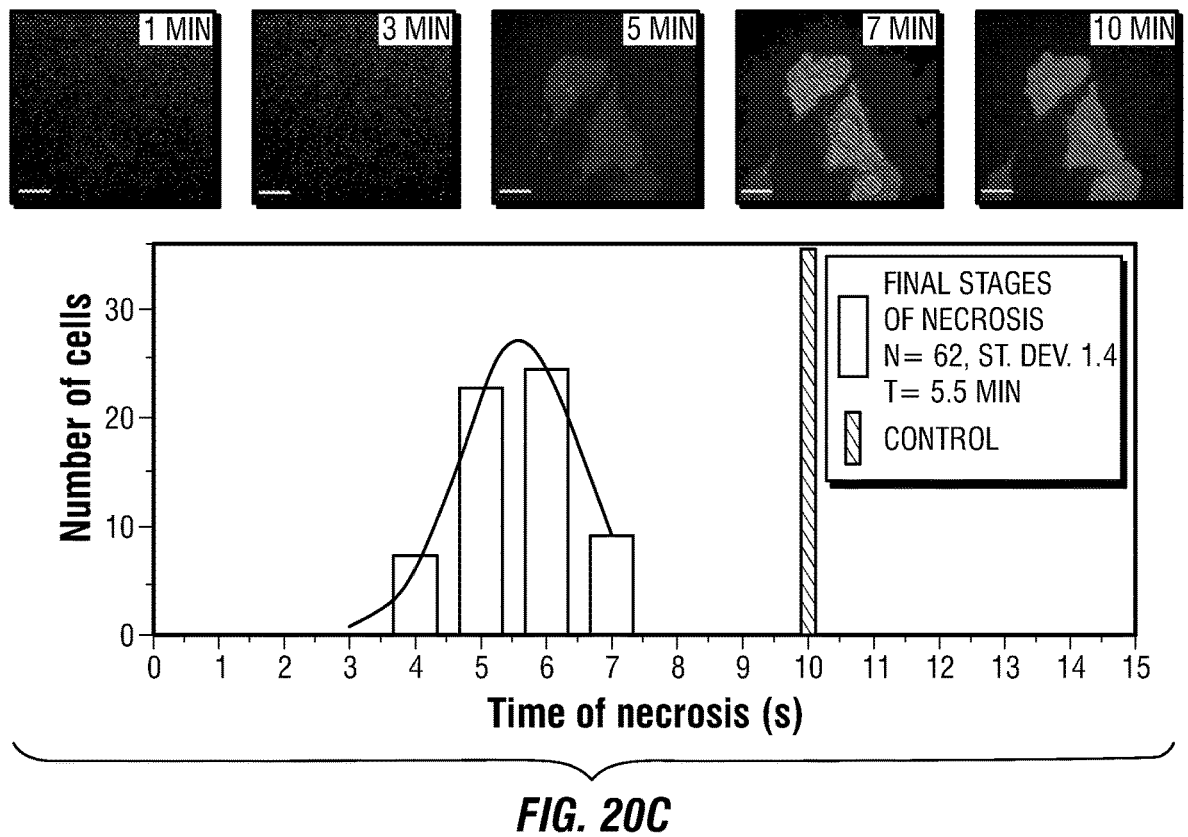
Figure 20D:
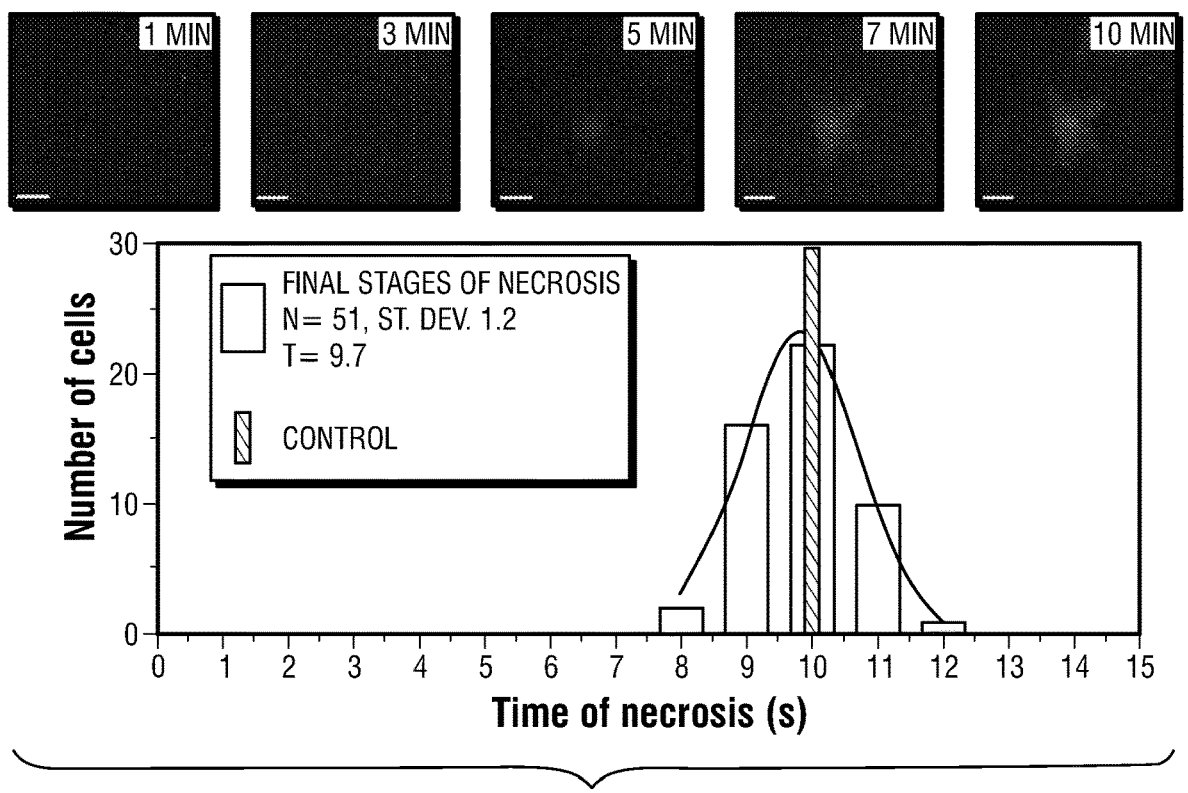
Figure 20E:
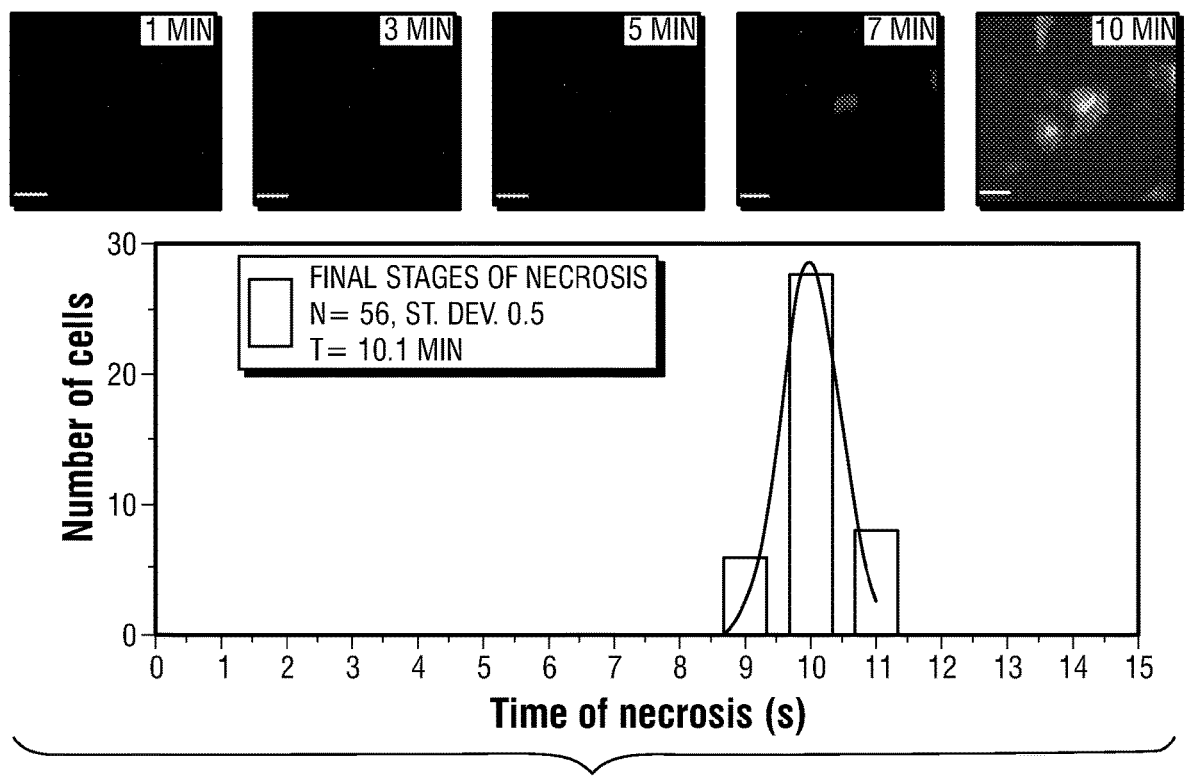
Figure 20F:
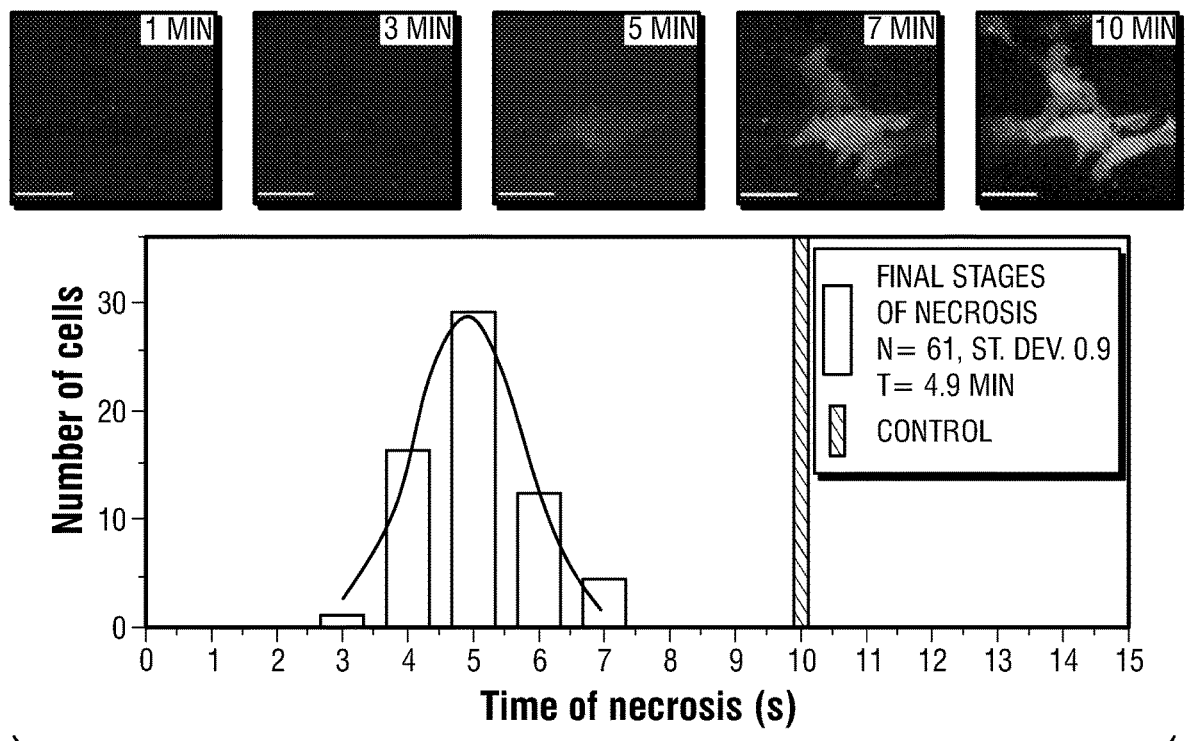
Figure 20G:
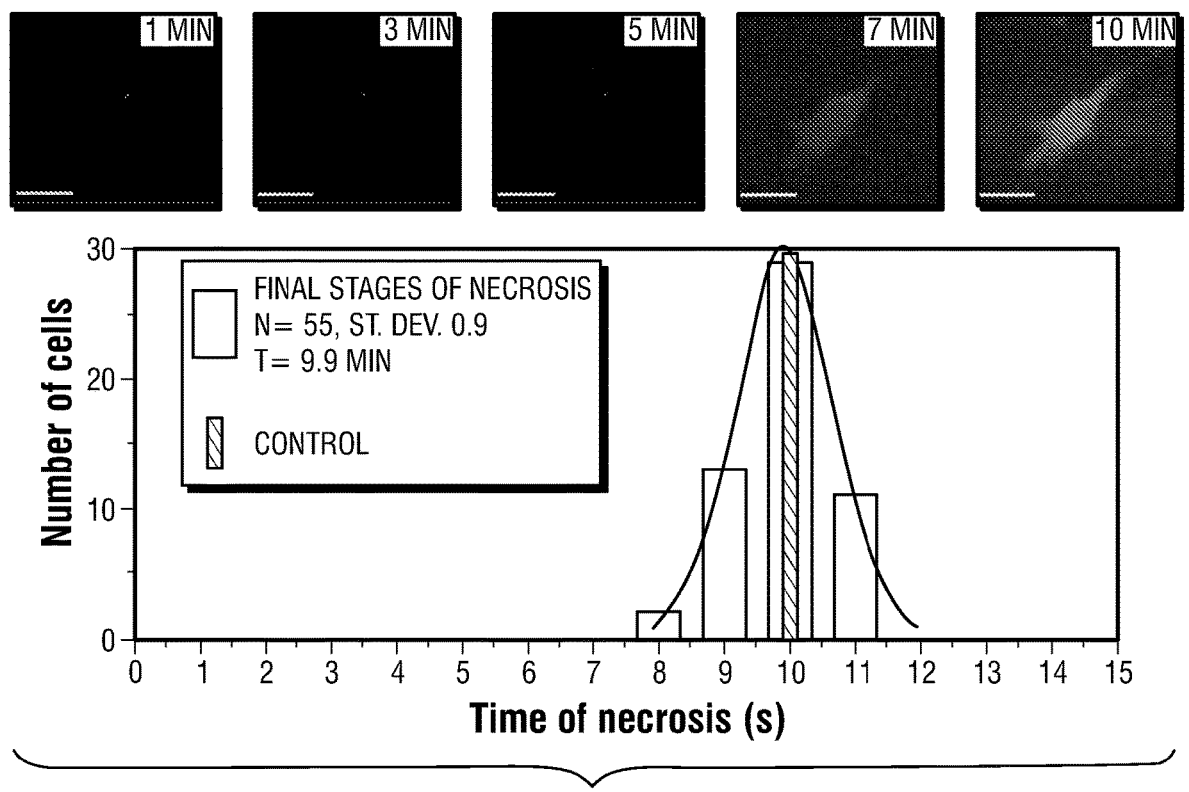
Figure 20H:
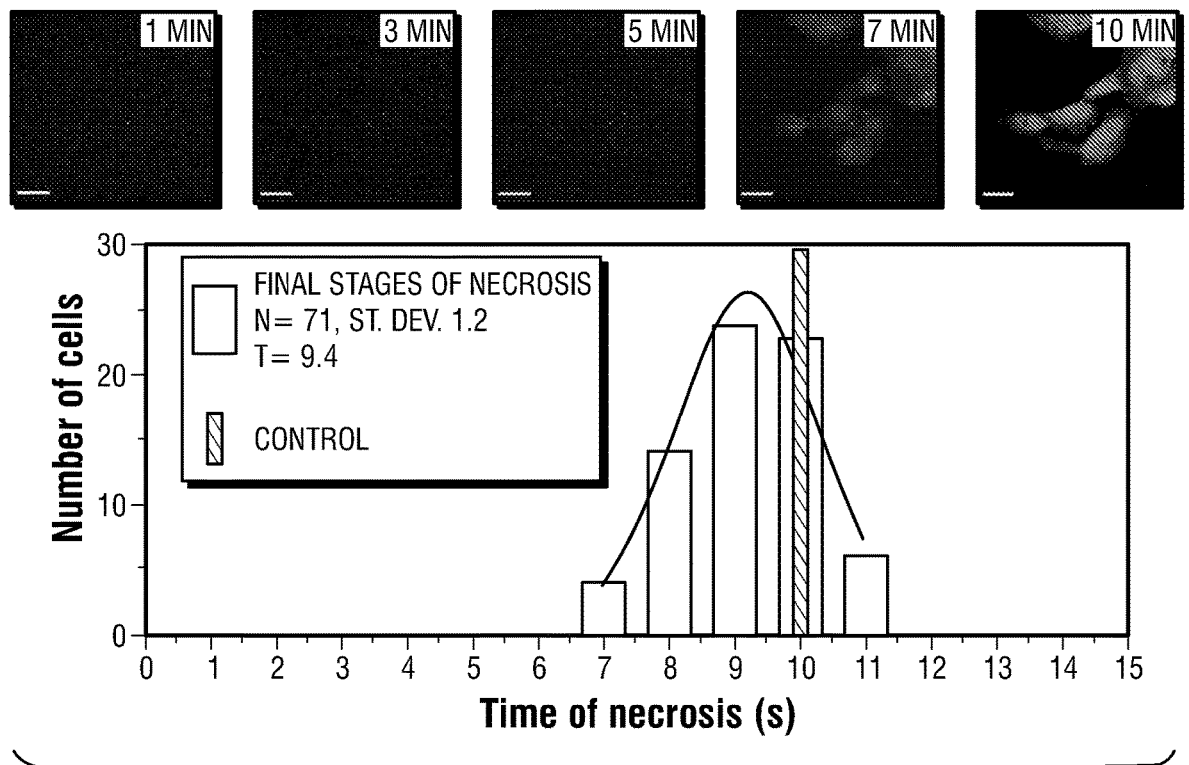
Figure 20I:
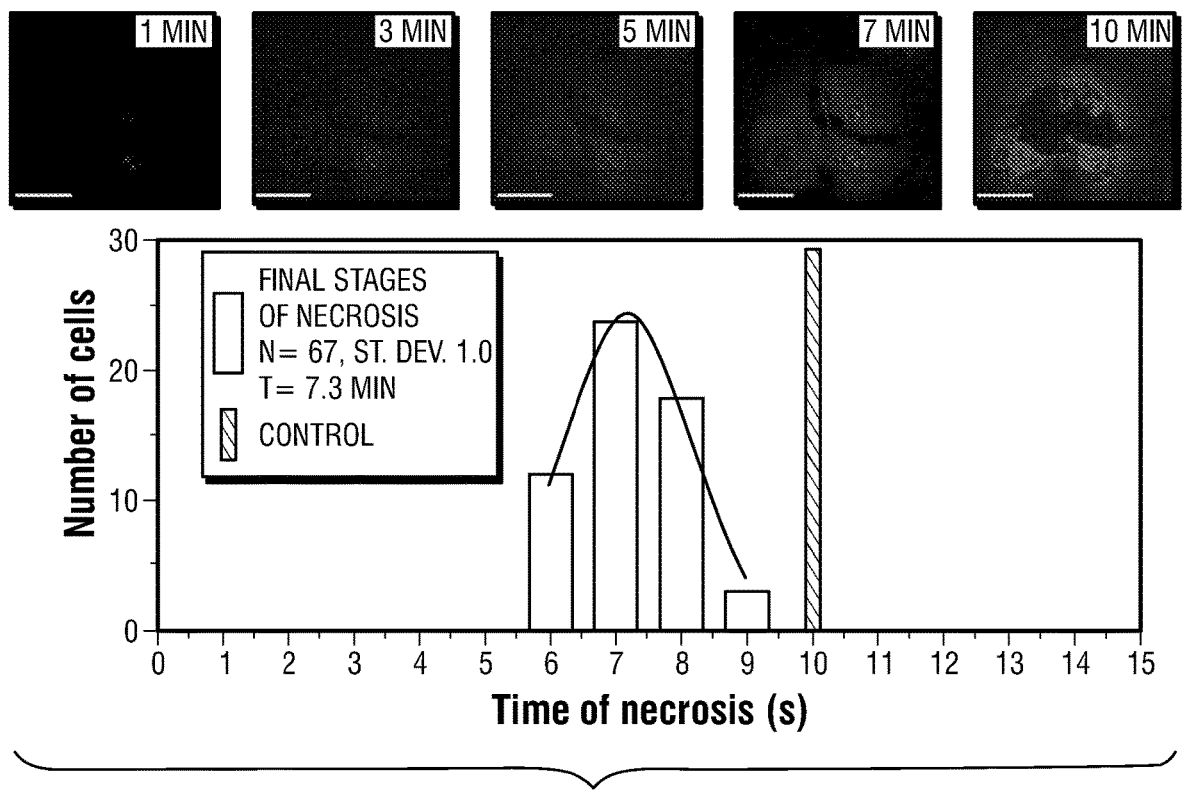
Figure 20J:
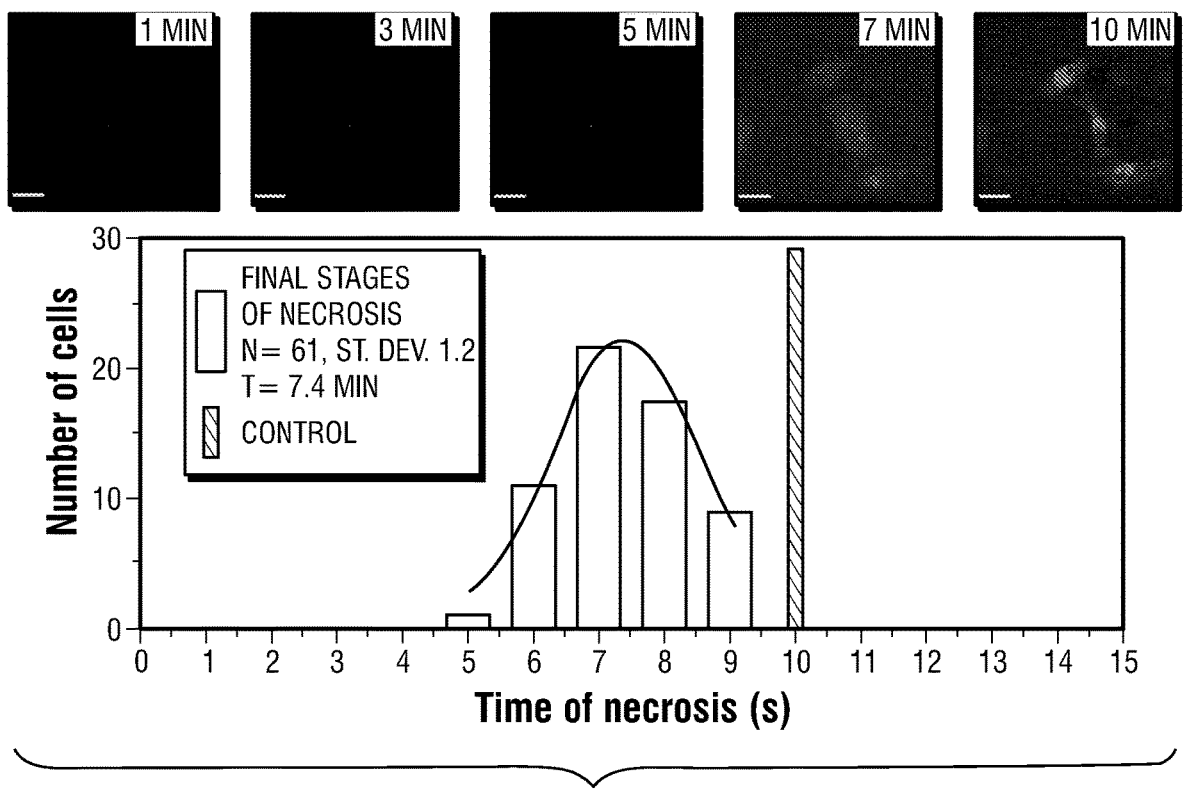
Figure 20K:
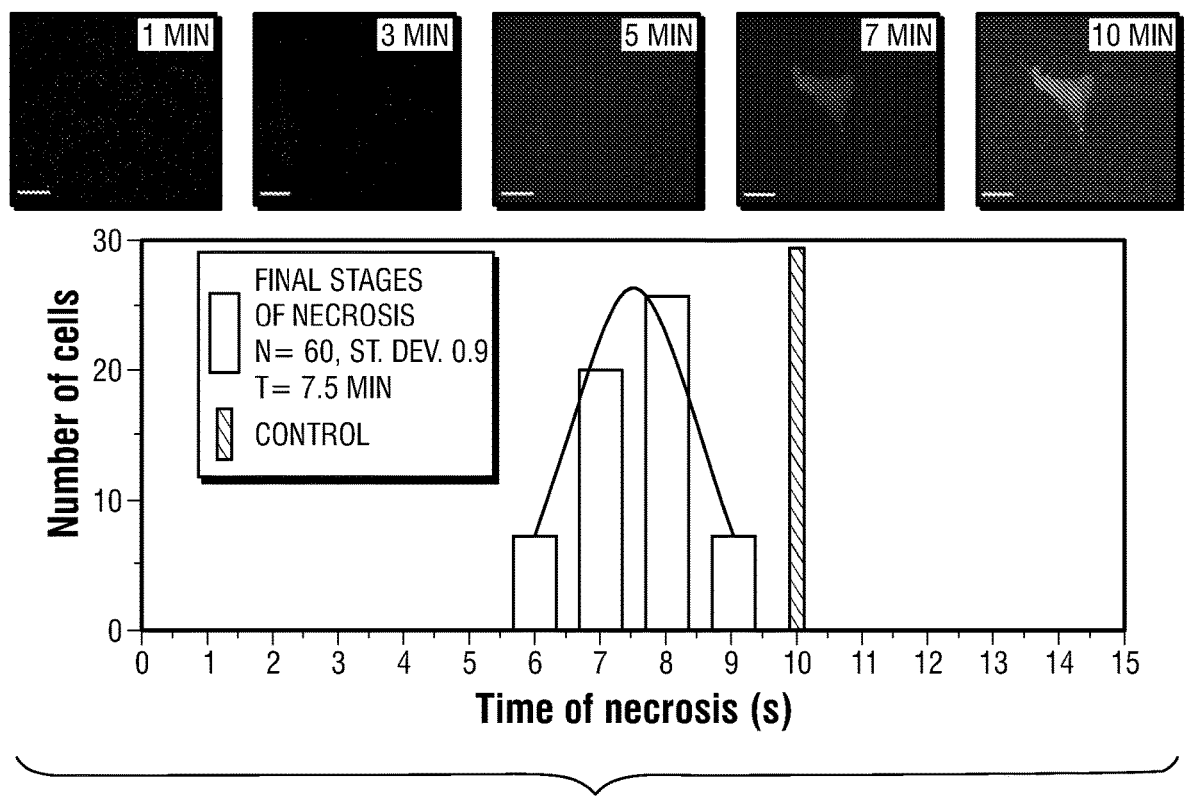
Figure 20L:
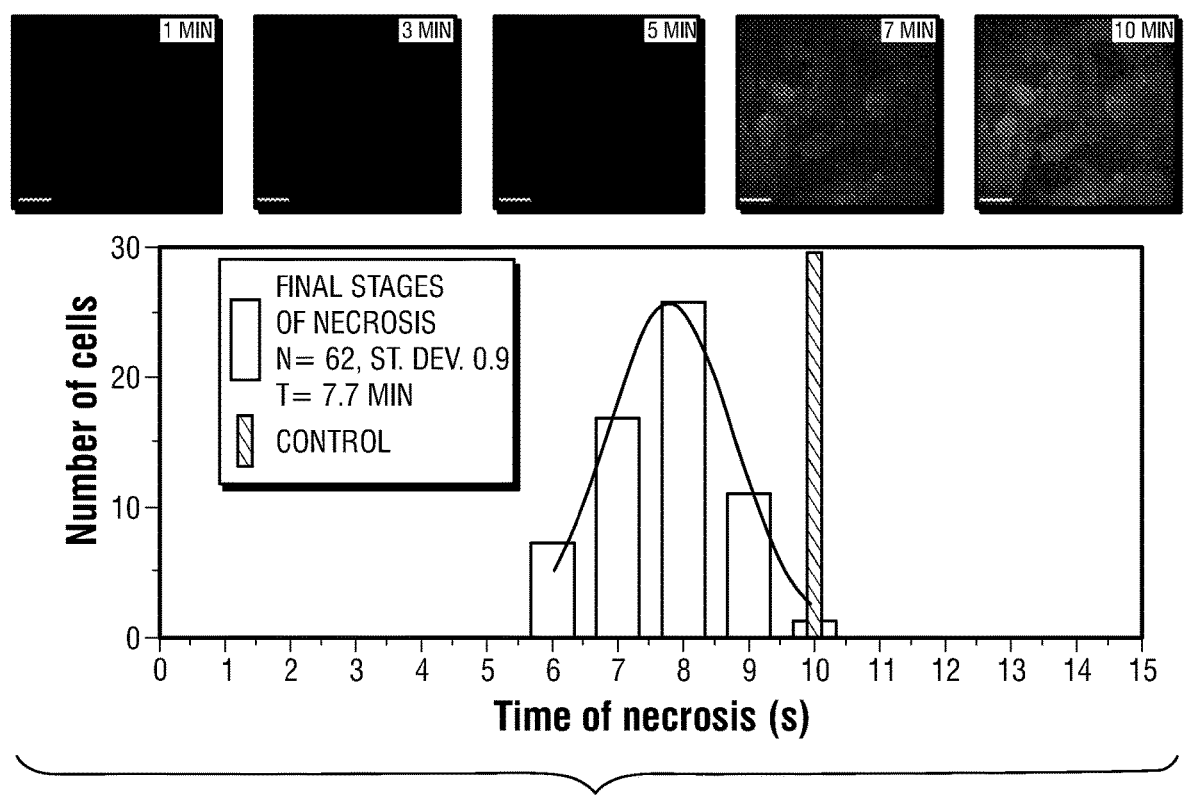

FIG. 16 shows whole-cell patch clamp studies of the dynamic effects of UV-induced molecular mechanical action of compound 3 upon HEK293 cells. Also shown are control studies using compound 3 without UV activation, UV-exposed rotor-free control molecule 5, and no molecular additives x. Compounds 3 and 5 were used at 1.0 µM concentrations. FIG. 16A shows transmembrane currents in HEK293 cells showing that cells treated with UV (355 nm)-activated molecular motors 3 have inward currents consistent with membrane degradation (bottom trace). Without UV illumination, cells treated with compounds 3 or 5 show no change in membrane currents over the 4 minute recording period (top two traces). Similarly, the rotor-free compound 5, and no molecular additive x, show no inward currents during UV illumination (center two traces). Cells were held at −70 mV in voltage clamp mode and UV exposure began 15 seconds after the start of the recording. Each recording is a biological replicate and all traces are shown (n=4 recordings from different cells for 3+UV; n=3 recordings from different cells for each other condition). FIG. 16B shows representative differential interference chromatography (DIC) images of cells captured before (t=0) and after (t=4 min) exposure to UV in the presence of compounds 3 or 5. The white arrows (lower right image) highlight membrane blebbing that appears only in the cells treated with UV-activated compound 3. The scale bar represents 10 µm and is applicable for each micrograph.

FIG. 17 shows the consecutive monitoring of the interconversion of cis and trans isomers of compound 8. FIG. 17A is a chromatogram of one of the isomers immediately after separation. FIG. 17B is a chromatogram of the fraction after being stored in the freezer for two weeks. FIG. 17C is a chromatogram of the fraction after being exposed to room light for 20 minutes. FIG. 17D is a chromatogram of the fraction after being irradiated with laboratory TLC UV light for 15 minutes.

FIG. 18 shows data related to monitoring the UV-activated nanomechanical action of compound 3 upon exposure to NIH 3T3 cells using a conventional CW mercury-arc excitation source equipped with an epi-fluorescence setup consisting of a Zeiss Axiovert 200M inverted microscope. Shown are live cell microscopy images of a selected NIH 3T3 cell pre-incubated with 500 nm of compound 3 for 30 minutes in live cell imaging cell culture media (Method A), including; (1) (green) UV-induced mitochondrial autofluorescence ($\lambda_{ex}$ BP365/50 nm, $\lambda_{dm}$ 395, $\lambda_{em}$ LP420 nm, $t_{aq}$=880 ms/FOV); (2) (red) PI (100 nM) fluorescence ($\lambda_{ex}$ BP456/12 nm, $\lambda_{dm}$ 570, $\lambda_{em}$ LP580 nm, $t_{aq}$=370 ms/FOV); (3) (orange) RGB merge and (4) corresponding transmission images using a conventional epi-fluorescence setup and high resolution CCD camera. The selected FOV was exposed to continuous UV radiation (365/50 Band-pass filter) for an initial time (i.e., 0 minute) (FIG. 18A), 5 minutes (FIG. 18B), and 30 minutes (FIG. 18C) to confirm UV-activated molecular-motor-induced cell necrosis.

FIG. 19 provides a demonstration that a two-photon illumination in the near-infra red (IR) region can activate molecular motors 3 or 8 and result in PI dye entering NIH 3T3 or PC-3 cells. FIG. 19A shows images of cells in live cell media with no molecular motors present. FIG. 19B shows images of identical cells but with a 1 µM control molecular motor 5 using Method A. FIG. 19C shows images of identical cells but with 1 µM of molecular motor 3 present using Method A. FIG. 19D shows images of PC-3 cells with 1.0 µM of molecular motor 8 present using Method B. The scale bars correspond to 20 µm.

FIG. 20 provides an additional demonstration that a two-photon illumination in the near-infra red (IR) region can activate the molecular motors 3, 8 or 9 and result in PI dye entering NIH 3T3 or PC-3 cells. FIG. 20A shows images of control NIH 3T3 cells in live cell media under two-photon illumination with no molecular motors present. FIG. 20B shows images of identical NIH 3T3 cells with 1 µM of control 5 present using Method A. FIG. 20C shows images of identical NIH 3T3 cells with 1 µM of molecular motor 3 present using Method A. FIG. 20D shows images of NIH 3T3 cells with 1 µM of molecular motor 8 present using Method B. FIG. 20E shows images of identical control PC 3 cells under two-photon illumination with no molecular motors present. FIG. 20F shows images of identical PC 3 cells with 1 µM of molecular motor 3 present using Method A. FIG. 20G shows images of identical PC-3 cells with 1 µM of control 5 present using Method A. FIG. 20H shows images of identical PC-3 cells with 1 µM of molecular motor 3 present using Method B. FIG. 20I shows images of identical PC-3 cells with 1 µM of molecular motor 8 present using Method A. FIG. 20J shows images of identical PC-3 cells with 1 µM of molecular motor 9 present using Method A. FIG. 20K shows images of identical PC3 cells with 1 µM of molecular motor 8 present using Method B. FIG. 20L shows images of identical PC-3 cells with 1 µM of molecular motor 9 present using Method B. The scale bars correspond to 20 µm.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

An important aspect of biomedical therapy is the effective delivery of various molecules such as drugs and genetic information into cells. In order to be effective, such delivery methods must facilitate the passage of the molecules across the lipid bilayer of cell membranes. Thus, several physical techniques have been used to open lipid bilayers of cellular membranes. Such techniques use physical energies such as electric fields, magnetic fields, temperature, ultrasound, and light. These techniques have been used to intentionally introduce foreign materials into cells, release molecular species from cells, or to induce necrosis.

Recently, molecular motors and switches that can change their conformation in a controlled manner after external stimulus have been explored to develop molecular machines that can have applications in the biomedical field. For example, the molecular photoswitch azobenzene has been adapted and used as a photochromic $K^+$ channel opener, as an optical controller of insulin secretion, and for restoration of light sensitivity in blind retinae.

However, current methods of facilitating the passage of materials through lipid bilayers continue to suffer from numerous limitations. For instance, many methods of delivering materials through lipid bilayers of cells become ineffective because cells develop resistance to the delivery agents. Furthermore, many of the existing methods of delivering materials into cells are not able to target desired lipid bilayers in a specific manner. The present disclosure addresses the aforementioned limitations.

In some embodiments, the present disclosure pertains to methods of opening a lipid bilayer. In some embodiments illustrated in FIG. 1, the methods of the present disclosure include steps of associating the lipid bilayer with a molecule that includes a moving component capable of moving in response to an external stimulus (step 10), and exposing the molecule to an external stimulus (step 12). The exposure of the molecule to the external stimulus causes the moving component of the molecule to move (step 14). Thereafter, the movement of the moving component of the molecule facilitates the opening of the lipid bilayer (step 16). In some embodiments, the opening of the lipid bilayer can be used to facilitate the passage of various materials through the lipid bilayer (step 18). Additional embodiments of the present disclosure pertain to the aforementioned molecules for opening a lipid bilayer.

Figure 2A:
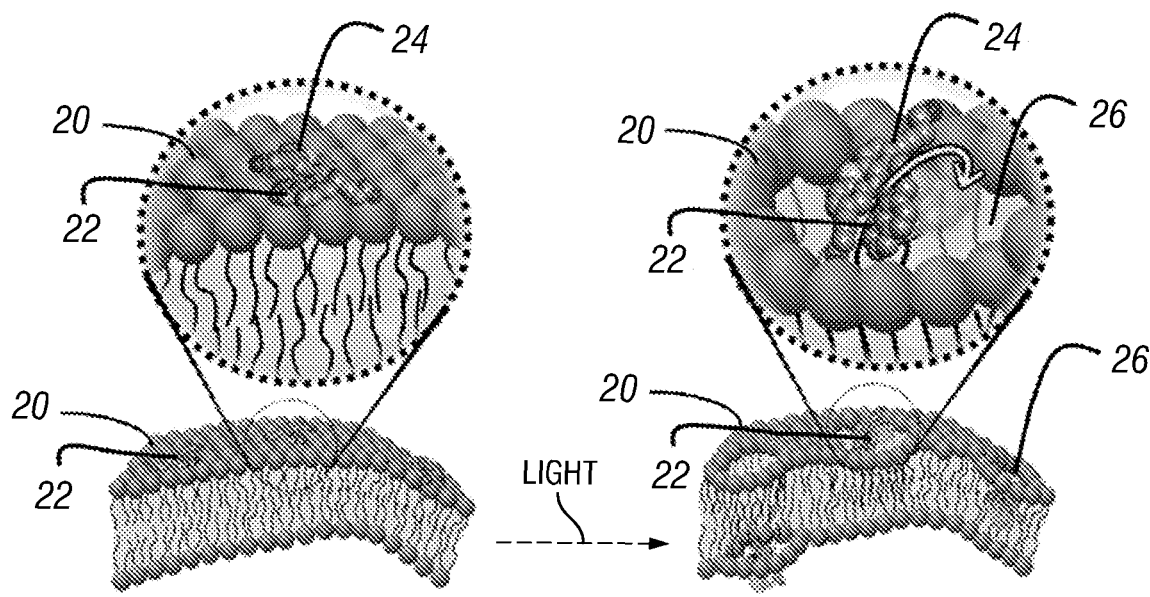

Examples of the methods and molecules of the present disclosure are also depicted in FIG. 2A. In this depiction, molecule 22 with moving component 24 becomes associated with lipid bilayer 20. Thereafter, the molecule is exposed to light irradiation (i.e., an external stimulus). The light irradiation causes moving component 24 of molecule 22 to move (i.e., rotate in this embodiment) and facilitate the opening of lipid bilayer 20 through the formation of pores 26.

As set forth in more detail herein, the present disclosure can have numerous embodiments. In particular, various molecules may become associated with various types of lipid bilayers in various manners. Moreover, the molecules may be exposed to various external stimuli in order to open the lipid bilayers through various mechanisms. Furthermore, the molecules and methods of the present disclosure can be utilized to pass various materials through the opened lipid bilayers for various purposes and applications.

Molecules for Opening Lipid Bilayers

The methods of the present disclosure can utilize various types of molecules for opening lipid bilayers. Additional embodiments of the present disclosure pertain to the aforementioned molecules for opening lipid bilayers.

The molecules of the present disclosure generally include a moving component capable of moving in response to an external stimulus. In some embodiments, the moving components of the present disclosure can include one or more conjugated systems. In some embodiments, the wavelength of the conjugated system may shift to the visible region, thereby making the moving component activatable to visible light.

In some embodiments, the molecules of the present disclosure also include a base component that is capable of embedding with a lipid bilayer. In some embodiments, the moving component is also capable of embedding with the lipid bilayer. In some embodiments, the base component is also capable of moving in response to an external stimulus.

In some embodiments, the molecules of the present disclosure also include one or more targeting agents. In some embodiments, the targeting agent is capable of directing the molecule to a specific type of a lipid bilayer, such as a lipid bilayer associated with cell membranes of particular cells, organs, or tissues. In some embodiments, the targeting agent is capable of binding to a receptor on a lipid bilayer of a cell membrane.

The molecules of the present disclosure may be associated with various types of targeting agents. For instance, in some embodiments, the targeting agent includes, without limitation, amino acids, peptides, proteins, aptamers, antibodies, small molecules, carbohydrates, polysaccharides, and combinations thereof. In some embodiments, the targeting agent includes peptides. In some embodiments, the targeting agent includes antibodies, such as monoclonal antibodies.

In some embodiments, the targeting agents may be used to target specific cell types, such as cancer cells (e.g., cancer cells associated with a specific type of cancer, such as skin-related cancers), fat (adipocyte) cells, or diseased cells. In some embodiments, the targeted cells have an overexpressed and specific cell surface receptor that is recognized by the targeting agents.

In some embodiments, the molecules of the present disclosure may also include one or more tracing agents. In some embodiments, the tracing agent can be utilized to track the association of molecules with a lipid bilayer.

The molecules of the present disclosure may be associated with various types of tracing agents. In some embodiments, the tracing agents may be detectable by magnetic resonance imaging (MRI), positron emission tomography (PET), or other imaging techniques. In some embodiments, the tracing agents include, without limitation, fluorophores, chromophores, dyes, radio-labeled molecules, radioactive nuclei, high contrast agents, gadolinium, gallium, thallium, fluorinated compounds, and combinations thereof.

In some embodiments, the molecules of the present disclosure also include one or more solubilizing agents. In some embodiments, the solubilizing agents help maintain the water solubility of the molecule.

The molecules of the present disclosure may be associated with various types of solubilizing agents. For instance, in some embodiments, the solubilizing agents include, without limitation, peptides, glycols, alcohols, carboxylates, polysaccharides, salts, acids, polyethers, polyethylene glycols (PEGs), carbohydrates, and combinations thereof. In some embodiments, the solubilizing agents include glycols, such as polyethylene glycol units. In some embodiments, the solubilizing agents include alcohols, such as polyvinyl alcohol and polyols. In some embodiments, the solubilizing agents include carboxylates, such as carboxylate moieties. In some embodiments, the solubilizing agents include acids, such as sulfonic acids. In some embodiments, the solubilizing agents include salts, such as ammonium salts.

In some embodiments, the molecules of the present disclosure may also include one or more active agents. In some embodiments, the molecules of the present disclosure may be associated with one or more active agents in a releasable manner. For instance, in some embodiments, the molecules of the present disclosure are releasably associated with one or more active agents through a cleavable bond, such as an ester linkage (e.g., cleavable by an esterase), an amide linkage (e.g., cleavable by an amidase), or a photolabile linkage (e.g., cleavable by UV light). In some embodiments, the molecules of the present disclosure are releasably associated with one or more active agents such that the one or more active agents are released from the molecules once the molecules facilitate the opening of the lipid bilayer or enter cells.

The molecules of the present disclosure may be associated with various types of active agents. For instance, in some embodiments, the active agents include, without limitation, drugs, peptides, polypeptides, nucleotides, DNA, RNA, siRNA, enzymes, and combinations thereof. In some embodiments, the active agents include drugs, such as anti-cancer drugs. In some embodiments, the active agents include peptides. The use of additional active agents can also be envisioned.

In more specific embodiments, the molecules of the present disclosure include the following structure (depicted as structure 1):

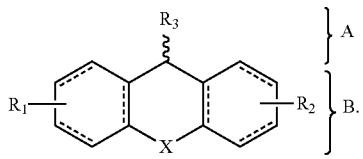

1

Region A in structure 1 includes moving component $R_3$, which is capable of moving in response to an external stimulus. Region B in structure 1 includes a base component. In some embodiments, the base component is capable of embedding with a lipid bilayer. In some embodiments, the moving component is capable of embedding with a lipid bilayer. In some embodiments the moving and base components can embed with a lipid bilayer. Structure 1 can also include other components, such as targeting agents, tracing agents, fluorophores, solubilizing agents, and active agents. In some embodiments, the other components can also embed with the lipid bilayer.

$R_1$ and $R_2$ in structure 1 can include various groups and moieties. For instance, in some embodiments, $R_1$ and $R_2$ can each independently include, without limitation, hydrogen, alkanes, alkenes, alkynes, carboxyl groups, ketone groups, alkoxy groups, methoxy groups, ethers, nitro groups, nitriles, sulfates, sulfonates, halogens, amine groups, amide groups, alcohols, aromatic groups, aryl groups, phenyl groups, annulated rings, carbohydrates, polysaccharides, peptides, targeting agents, tracing agents, fluorophores, solubilizing agents, active agents, and combinations thereof.

In some embodiments, $R_1$ and $R_2$ can each include annulated rings. In some embodiments, the annulated rings, when aromatic or further pi-electron-conjugated, can facilitate the activation of the molecules of the present disclosure by a lower energy source, such as visible light. X in structure 1 can also include various groups and moieties. For instance, in some embodiments, X can include, without limitation, S, $CH_2$, O, and combinations thereof. In some embodiments, X includes S.

Moving component $R_3$ in structure 1 can also include various structures. For instance, in some embodiments, $R_3$ includes the following structure (depicted as structure 2):

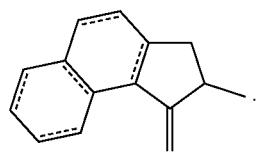

2

In some embodiments, $R_3$ in structure 1 includes the following structure (depicted as structure 3):

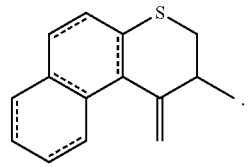

3

The use of additional moving component structures can also be envisioned. For instance, in some embodiments, the moving components or molecules may have one or more annulated rings, such has annulated aromatic rings. Due to the additional annulated aromatic rings, the light absorbance and emission spectra of a molecule's moving component may undergo bathochromic shifts in some embodiments, thereby being excited in the visible region at 400 nm or higher wavelengths (e.g., at least 500 nm or even 700 nm).

In some embodiments, the presence of additional annulated aromatic rings on a molecule or a moving component may facilitate the excitation of the moving component in the near infra-red (IR) region at greater than 700 nm. In some embodiments, as excitation wavelength increases, the energy that the moving component exerts on the lipid bilayer decreases. Therefore, in some embodiments, an assessment of the energy requirements for lipid bilayer disruption followed by correlation to the excitation and emission energies of the molecule may be required. The Examples provide various methods for such energy calculation.

In more specific embodiments, the molecules of the present disclosure include the following structure (depicted as structure 4):

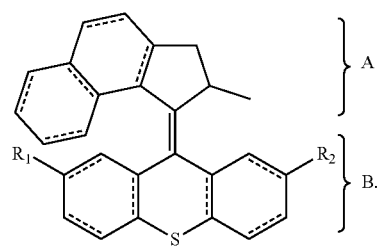

4

Region A in structure 4 includes a moving component capable of moving in response to an external stimulus. Region B in structure 4 includes a base component that is capable of embedding with a lipid bilayer. Structure 4 can also include other components, such as targeting agents, tracing agents, fluorophores, solubilizing agents, and active agents. In addition, $R_1$ and $R_2$ can include various moieties and functional groups that were described previously.

In more specific embodiments, the molecules of the present disclosure include the following structure (depicted as structure 5):

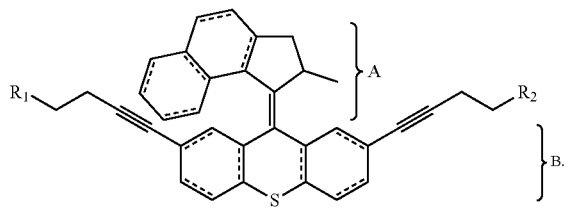

Region A in structure 5 includes a moving component capable of moving in response to an external stimulus. Region B in structure 5 includes a base component that is capable of embedding with a lipid bilayer. Structure 5 can also include other components, such as targeting agents, tracing agents, fluorophores, solubilizing agents, and active agents. In addition, $R_1$ and $R_2$ can include various moieties and functional groups that were described previously.

The use of additional molecules capable of opening lipid bilayers can also be envisioned. For instance, more specific examples of the molecules of the present disclosure that resemble the molecules depicted in the aforementioned structures are shown in FIGS. 2C, 2D-1 and 2D-2 (e.g., molecules 1-4 and 6-10). For the sake of clarity, aforementioned structures 1-5 are different from molecules 1-5 depicted in FIG. 2C.

Lipid Bilayers

The molecules and methods of the present disclosure can be utilized to open various types of lipid bilayers. In some embodiments, the lipid bilayers may be components of cell membranes, such as external or internal cellular membranes. In some embodiments, the lipid bilayers may be components of an organelle, such as the mitochondria. In some embodiments, the lipid bilayers may be components of a nuclear membrane.

In some embodiments, the lipid bilayers may be components of cell membranes in vivo, such as cell membranes of a tissue or organ in a subject (e.g., a human being). In some embodiments, the cell membranes may be components of various cell types of interest, such as cancer cells, tumor cells, diseased cells, fat cells, and combinations thereof.

In some embodiments, the lipid bilayers may be components of cell membranes in vitro, such as cell membranes in a cell culture medium. In some embodiments, the lipid bilayers may be components of vesicles, such as synthetic vesicles in vitro. The use of additional lipid bilayers can also be envisioned.

Association of Molecules with Lipid Bilayers

The molecules of the present disclosure may become associated with lipid bilayers in various manners. For instance, in some embodiments, the molecules of the present disclosure become embedded within the lipid bilayer. In some embodiments, the molecules of the present disclosure are inserted into the lipid bilayer. In some embodiments, the molecules of the present disclosure are placed on surfaces of the lipid bilayer.

The molecules of the present disclosure may become associated with lipid bilayers by various steps. For instance, in some embodiments, the molecules of the present disclosure become associated with lipid bilayers by exposing the lipid bilayers to the molecules. In some embodiments, the molecules of the present disclosure become associated with lipid bilayers by incubating the lipid bilayers with the molecules. In some embodiments, the molecules of the present disclosure become associated with lipid bilayers by contacting the lipid bilayers with the molecules.

In some embodiments, the molecules of the present disclosure become associated with lipid bilayers in vitro. In some embodiments, the molecules of the present disclosure become associated with lipid bilayers in vivo in a subject (e.g., a human being). In some embodiments, the molecules of the present disclosure become associated with lipid bilayers in vivo in a subject by administering the molecules to the subject.

Various methods may be utilized to administer the molecules of the present disclosure to a subject. For instance, in some embodiments, the administration occurs by a method that includes, without limitation, oral administration, inhalation, subcutaneous administration, intravenous administration, intraperitoneal administration, intramuscular administration, intrathecal injection, topical administration, central administration, peripheral administration, and combinations thereof.

In some embodiments, the molecules of the present disclosure may be co-administered to a subject with additional materials, such as active agents. In some embodiments, the administered molecules of the present disclosure may be releasably linked to an active agent. In some embodiments, the administered molecules may be utilized to treat a disease in a subject, such as skin-related cancers. In some embodiments, the skin-related cancers include, without limitation, skin cancer (e.g., melanoma), colorectal cancers, oral cancers, vaginal cancers, and combinations thereof.

In more specific embodiments, the molecules of the present disclosure may be administered to a subject through intravenous administration (e.g., intravenous injection). In some embodiments, the molecules of the present disclosure may be administered onto a skin of subject through subcutaneous (i.e., subdermal) administration (e.g., subcutaneous injection). In some embodiments, the subdermal administration can occur in the presence of a skin-penetrating material, such as dimethylsulfoxide, thereby carrying the molecule through the skin. In some embodiments, the molecule (e.g., the molecule and its associated or co-administered active agent) can be carried through the skin using these dermal transport agents. In some embodiments, the dermal transport agents can also facilitate transport of the molecules of the present disclosure (e.g., the molecule and its associated or co-administered active agents) through the vaginal, colorectal, oral and gastrointestinal layers to facilitate transport of the molecules to their sites of interest before or during activation by exposure to an external stimulus (e.g., light or other external stimuli).

In some embodiments, the molecules of the present disclosure may be co-administered to a subject along with an energy source capable of providing an external stimulus. In some embodiments, the energy source includes a light source, such as an LED lamp in capsule form. In some embodiments, the molecules of the present disclosure may be co-administered to a subject along with an energy source (e.g., LED lamp) and an active agent (e.g., peptide-based drug).

In some embodiments, a capsule that contains an LED lamp and the molecules of the present disclosure (i.e., nanomachines) and an active agent (e.g., a drug associated with the molecule or co-administered with the molecule, such as a peptide-based drug) can be dissolved in the small intestines such that the LED lamp activates the molecules (i.e., nanomachines) which aid in opening the gastrointestinal lining to permit the active agent to enter the bloodstream. In some embodiments, the aforementioned administration can occur in conjunction with an epithelial transport agent. Additional administration methods can also be envisioned.

The lipid bilayers of the present disclosure may be associated with the molecules of the present disclosure for various periods of time. For instance, in some embodiments, the association takes place from about 1 minute to about 48 hours. In some embodiments, the association takes place from about 5 minutes to about 48 hours. In some embodiments, the association takes place from about 5 minutes to about 2 hours.

The lipid bilayers of the present disclosure may become associated with various concentrations of the molecules of the present disclosure. For instance, in some embodiments, the molecule concentrations range from about 10 nM to about 10 µM. In some embodiments, the molecule concentrations range from about 100 nM to about 1 µM. In some embodiments, the molecule concentrations range from about 100 nM to about 500 nM. In some embodiments, the molecule concentrations range from about 100 nM to about 200 nM. In some embodiments, the molecule concentrations are at least about 100 nM.

Exposure of Molecules to External Stimuli

The molecules of the present disclosure may be exposed to various external stimuli in order to cause the movement of their moving component. For instance, in some embodiments, the molecules of the present disclosure are exposed to an external stimulus that includes an energy source. In some embodiments, the energy source includes, without limitation, ultraviolet (UV) light, visible light, near-infra red (IR) light, a radio frequency (RF) energy source, a two-photon energy source, an electric field, a magnetic field, an electromagnetic field, and combinations thereof. In some embodiments, the energy source includes ultraviolet light. In some embodiments, the energy source is in the form of electromagnetic radiation.

In some embodiments, a two-photon energy source is utilized to provide a very focused area of exposure. In some embodiments, the energy source includes two photons of near-infra red light. In some embodiments, the near-infra red light activates the molecules of the present disclosure by the use of two photons at about 710 nm.

In some embodiments, the molecules of the present disclosure are exposed to an energy source at various wavelengths. For instance, in some embodiments, the wavelength of the energy source ranges from about 355 nm to about 365 nm. In some embodiments, the wavelength of the energy source ranges from about 500 nm to about 610 nm. In some embodiments, the wavelength of the energy source ranges from about 600 nm to about 750 nm. Additional wavelength ranges can also be envisioned.

The molecules of the present disclosure may be exposed to an external stimulus for various periods of time. For instance, in some embodiments, the exposure time may be from about 1 second to about 600 seconds. In some embodiments, the exposure time may be from about 1 second to about 400 seconds. In some embodiments, the exposure time may be from about 1 second to about 300 seconds. In some embodiments, the exposure time may be from about 1 second to about 200 seconds. In some embodiments, the exposure time may be from about 1 second to about 60 seconds. In some embodiments, the exposure time may be from about 1 second to about 30 seconds. Additional exposure times can also be envisioned.

The molecules of the present disclosure may be exposed to an external stimulus at various periods of time. For instance, in some embodiments, the exposing occurs after the molecule is associated with a lipid bilayer. In some embodiments, the exposing occurs before the molecule is associated with a lipid bilayer. In some embodiments, the exposing occurs while the molecule is associated with a lipid bilayer. In some embodiments, the exposing occurs before or during the association of the molecule with the lipid bilayer.

The molecules of the present disclosure may be exposed to external stimuli in various environments. For instance, in some embodiments, the molecules of the present disclosure are exposed to an external stimulus in vitro. In some embodiments, the in vitro environment may be a cell culture medium that contains lipid bilayers as components of cell membranes.

In some embodiments, the molecules of the present disclosure are exposed to an external stimulus in vivo. In some embodiments, the in vivo environment may be the organ or tissue of a subject that has been administered with the molecules of the present disclosure. In some embodiments, the in vivo environment may be the skin of a subject that has been administered with the molecules of the present disclosure.

Molecular Movement

The exposure of the molecules of the present disclosure to an external stimulus can have various effects on the molecules. In particular, the exposure causes the moving component of the molecule to move in various manners in response to the external stimulus. For instance, in some embodiments, the movement includes, without limitation, rotation, flapping, jumping, and combinations thereof. In some embodiments, the movement includes flapping.

In some embodiments, the movement is confined to the moving component of the molecule. In some embodiments, the movement occurs throughout the entire molecule.

In more specific embodiments, the movement includes rotation. The moving components of the molecules of the present disclosure can rotate in various manners. For instance, in some embodiments, the moving component of the molecules of the present disclosure rotates in a unidirectional manner. In some embodiments, the moving component rotates in a non-reciprocating unidirectional manner. In some embodiments, the moving component rotates in a bi-direction manner. In some embodiments, the moving component rotates relative to a base component of the molecule.

The moving component of the molecules of the present disclosure can rotate for various degrees in response to an external stimulus. For instance, in some embodiments, the moving component rotates from about 45 degrees to about 360 degrees. In some embodiments, the moving component rotates from about 60 degrees to about 180 degrees. In some embodiments, the moving component rotates for at least about 180 degrees. In some embodiments, the moving component rotates for at least about 360 degrees.

The moving component of the molecules of the present disclosure can also rotate at various rates in response to an external stimulus. For instance, in some embodiments, the moving component of the molecules of the present disclosure can rotate at rotation rates of about 1-10 MHz. In some embodiments, the moving component of the molecules of the present disclosure can rotate at rotation rates of about 2-3 MHz.

In some embodiments, the moving component of the molecules of the present disclosure can rotate at 1-10 revolutions per hour. In some embodiments, the moving component of the molecules of the present disclosure can rotate at 1-5 revolutions per hour. In some embodiments, the moving component of the molecules of the present disclosure can rotate at 1-2 revolutions per hour. In some embodiments, the moving component of the molecules of the present disclosure can rotate at about 1.8 revolutions per hour.

Opening of Lipid Bilayers

The movement of the moving component of the molecules of the present disclosure can have various effects on lipid bilayers. In some embodiments, the movement facilitates the opening of the lipid bilayers in various manners.

For instance, in some embodiments, the movement of the moving component of the molecules of the present disclosure changes the conformation of the molecule (e.g., change in the conformation of molecule 22, as depicted in FIG. 2A). Thereafter, the change in the conformation of the molecule leads to the opening of the lipid bilayer. In some embodiments, the movement produces a tangential mechanical force that leads to the opening of the lipid bilayer.

In some embodiments, the movement of the moving component of the molecules of the present disclosure facilitates the opening of lipid bilayers by disrupting the lipid bilayers. In some embodiments, the movement facilitates the opening of the lipid bilayers by dislocation of lipid bilayer molecules. In some embodiments, the movement facilitates the opening of the lipid bilayers by causing rupture or degradation of the lipid bilayers.

The opening of lipid bilayers by the molecules of the present disclosure may result in the formation of various structures. For instance, in some embodiments, the lipid bilayers are opened by forming pores (e.g., pores 26, as depicted in FIG. 2A). In some embodiments, the formed pores may be transient. In some embodiments, the formed pores may be permanent. In some embodiments, the formed pores may have various diameters. In some embodiments, the pore diameters range from about 10 nm to about 500 µm.

Applications and Advantages

The methods and molecules of the present disclosure may be utilized to open various types of lipid bilayers for various applications. For instance, in some embodiments, the methods and molecules of the present disclosure can be utilized to open lipid bilayers for passage of various materials through the lipid bilayer. In some embodiments, such materials can include, without limitation, analytes, active agents, drugs, nucleotides, DNA, RNA, siRNA, polypeptides, enzymes, polysaccharides, imaging agents, and combinations thereof. In some embodiments, the materials can include nucleotides, such as siRNA, DNA, RNA, and combinations thereof.

In some embodiments, the methods and molecules of the present disclosure can be utilized for passage of materials through a lipid bilayer and into cells. In some embodiments, the methods and molecules of the present disclosure can be utilized for passage of materials through a lipid bilayer and out of cells. In some embodiments, the methods and molecules of the present disclosure can be utilized for passage of materials through a lipid bilayer and into vesicles. In some embodiments, the methods and molecules of the present disclosure can be utilized for passage of materials through a lipid bilayer and out of vesicles.

In some embodiments, the methods and molecules of the present disclosure can be utilized for passage of materials through a lipid bilayer and into organelles of cells, such as the mitochondria. In some embodiments, the methods and molecules of the present disclosure can be utilized for passage of materials through a lipid bilayer and into the nucleus of cells.

In more specific embodiments, the methods and molecules of the present disclosure can be utilized for passage of materials through a lipid bilayer and into cells in order to induce various effects on the cells. In some embodiments, such induced effects can include, without limitation, cell death, necrosis, disease treatment, and combinations thereof. In some embodiments, such effects can occur in vitro (e.g., in a cell culture medium) or in vivo (e.g., in a subject).

In more specific embodiments, the methods and molecules of the present disclosure can be utilized to open lipid bilayers of a cell membrane in a cell culture medium. Such methods can include associating the lipid bilayers of the cell membranes with the molecules of the present disclosure and exposing the molecules to an external stimulus in the presence of various materials (e.g., analytes, active agents, drugs, nucleotides, DNA, RNA, siRNA, polypeptides, enzymes, polysaccharides, imaging agents, and combinations thereof) such that the materials enter the cells after exposure and induce various effects on the cells (e.g., cell death, necrosis, disease treatment, and combinations thereof).

In further embodiments, the methods and molecules of the present disclosure can be utilized to open lipid bilayers of a cell membrane associated with an organ or a tissue in a subject by administering the molecules of the present disclosure to the subject such that the lipid bilayers of the cell membranes of the desired organ or tissue become associated with the molecules of the present disclosure. The desired organ or tissue may be exposed to an external stimulus in the presence of various co-administered materials (e.g., analytes, active agents, drugs, nucleotides, DNA, RNA, siRNA, polypeptides, enzymes, polysaccharides, imaging agents, and combinations thereof) such that the materials enter the cells of the tissue or organ after exposure and induce various effects (e.g., cell death, necrosis, disease treatment, and combinations thereof).

In some embodiments, the methods and molecules of the present disclosure can be utilized for the sculpting of cells, such as fat (adipocyte) cells. For instance, in some embodiments, the molecules of the present disclosure may be administered (e.g., subcutaneously injected) under the skin of a subject where fat cells reside (or administered through other methods, such as transdermal administration or intravenous injection). An external stimulus (e.g., light or other external stimuli, such as radiofrequency fields, electric fields or magnetic fields) may be applied outside the skin to expose the molecules of the present disclosure to irradiation (e.g., UV, visible (e.g., red light) or two-photon near-infra red irradiation) through the skin and necrose the fat cells. After a few days, the aforementioned steps may be repeated for additional sculpting. In some embodiments, the sculpting of cells in accordance with the methods of the present disclosure can be utilized to selectively remove cells (e.g., fat cells) from a desired area.

In additional embodiments, the methods and molecules of the present disclosure can be utilized to treat skin-related cancers, such as skin cancer (e.g., melanoma), colorectal cancers, oral cancers, and vaginal cancers. In some embodiments, the molecules of the present disclosure are administered to the affected cells (e.g., via subcutaneous injection or oral administration). An energy source (e.g., a light source, such as a light source via an endoscope or an administered pill) could then be utilized to expose the molecules to an external stimulus (e.g., UV irradiation) and destroy those cells. In some embodiments, a UV light source (e.g., at wavelengths of about 350-360 nm) or a near-infra red light source could be utilized to irradiate the cells.

In more specific embodiments, the methods and molecules of the present disclosure can be utilized to facilitate the uptake of various active agents (e.g., peptide-based drugs) by a subject. For instance, in some embodiments, the active agent may be co-administered to a subject along with the molecules of the present disclosure and an energy source that is capable of providing an external stimulus (e.g., an LED light). In some embodiments, the molecules of the present disclosure may be associated with the active agents and co-administered with the energy source. In some embodiments, the co-administration occurs through the use of a carrier, such as a capsule. In some embodiments, the carrier may release the active agent (e.g., peptide-based drug), the molecule (i.e., the nanomachine), and the energy source (e.g., an LED light) near a particular cellular region, tissue or organ of the subject (e.g., the jejunum). Thereafter, the molecule associates with lipid bilayers and is activated by the energy source. This in turn facilitates the lipid bilayers of the particular cellular region, tissue or organ to open and uptake the active agents.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Opening of Cell Membranes by Molecular Machines

In this Example, Applicants use nanomechanical action to open cellular membranes by association of molecular motors with lipid bilayers, and then activating the motors with light. Using precisely designed molecular motors and complementary experimental protocols, nanomechanical action can (a) induce the diffusion of analytes out of synthetic vesicles, (b) enhance diffusion of traceable molecular machines into and within live cells, (c) induce necrosis, (d) introduce analytes into live cells, and (e) be selectively targeted to specific live cell-surface recognition sites through nanomachines bearing short peptide addends. Applicants demonstrate that, beyond in vitro applications demonstrated in this Example, in vivo use can follow, especially through the use of two-photon-, near-infrared- and radio-frequency-activated domains.

Figure 2B:
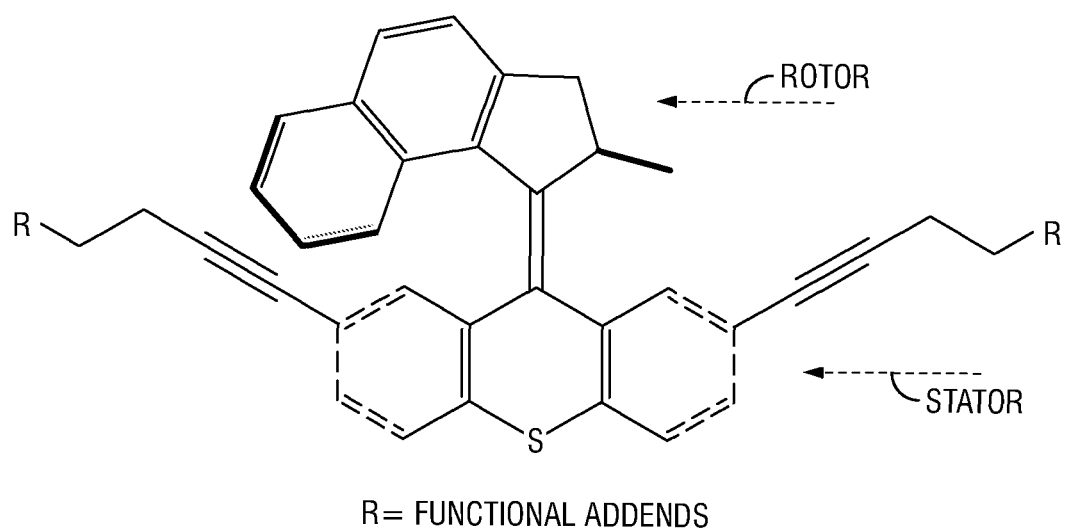
Figure 2D:
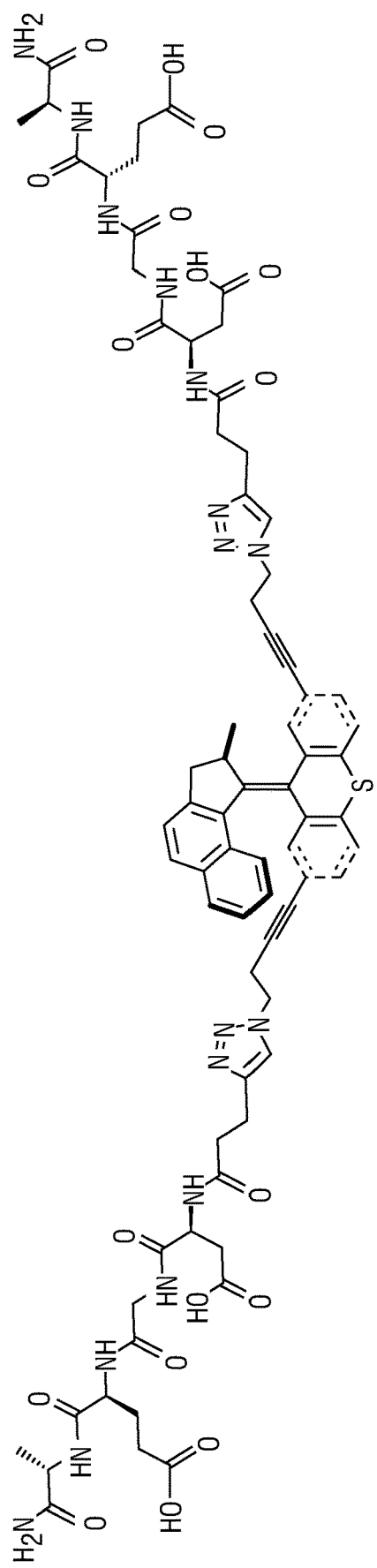
Figure 1:
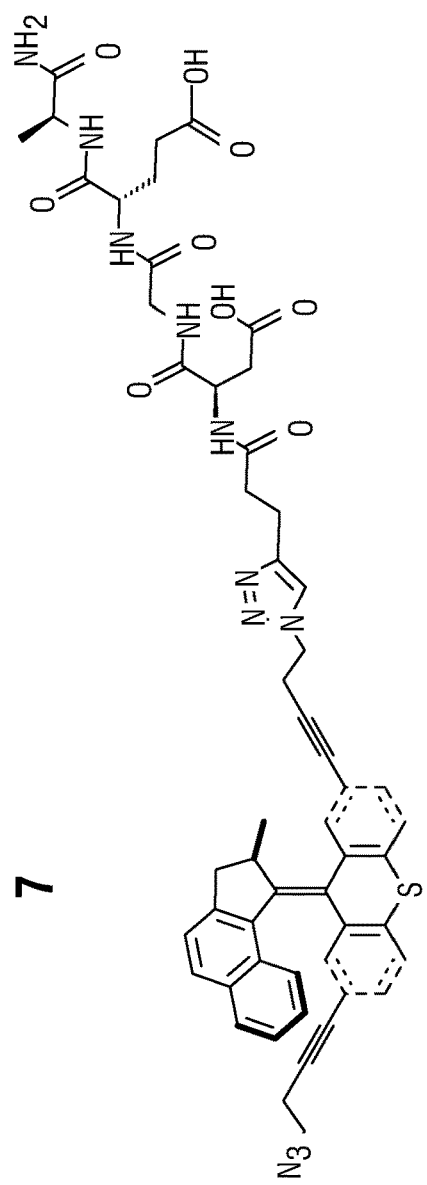

A scheme for nanomechanical action upon a lipid bilayer is shown in FIG. 2A and the general design of a molecular machine suitable for transport though a lipid bilayer is shown in FIG. 2B. As seen in FIG. 2C, these include molecular motors bearing fluorophores for tracking (1 and 2), smaller nanomachines (3 and 4), a control that bears a stator but no rotor (5), a control analogue (6) that can only undergo cis-trans isomerization (flapping) at room temperature, and targeting systems that bear peptide sequences for binding to specific cell-surface receptors (7-10).

Applicants previously demonstrated that molecular machine 1 displays enhanced diffusion in solution when the fast light-driven motor is activated by 355-365 nm UV light. Applicants envision that similar motor-bearing nanomachines could be activated while associated with lipid membranes.

Figure 3:
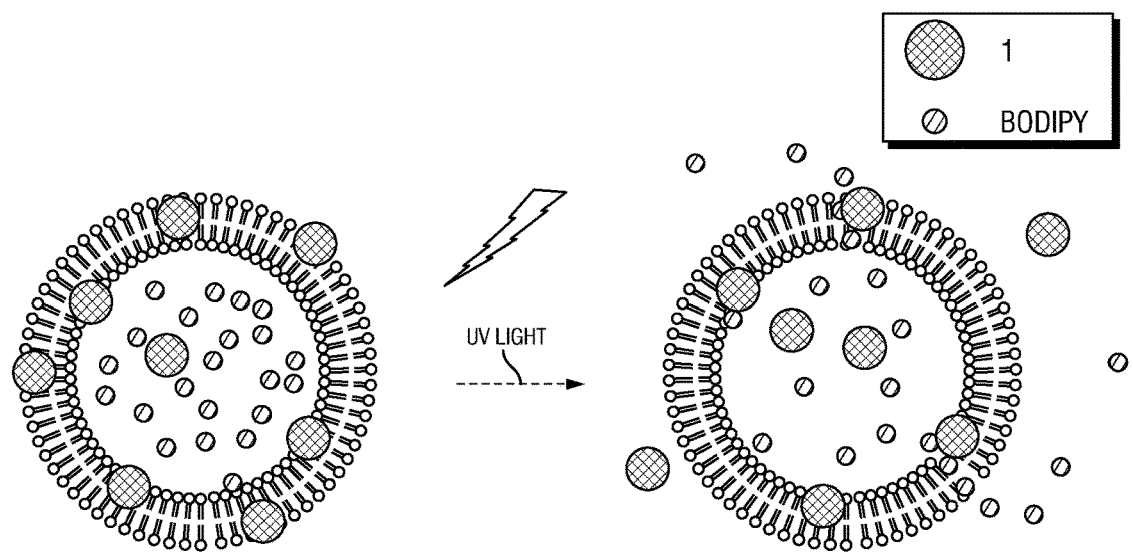

First, synthetic bilipid vesicles were opened using nanomachine 1 to release BODIPY dyes that were co-encapsulated with 1 in the vesicle (FIG. 3). The release of BODIPY dye molecules (not nanomachine-bound) encapsulated in a bilipid vesicle was studied with UV-exposure, and there was little release of the BODIPY dye from the synthetic vesicle.

Next, BODIPY and 1 were co-encapsulated in the bilipid vesicles, and a UV light-emitting diode was used as the activation source for 1 (FIG. 4). As the UV irradiation time increased, the fluorescence intensity of the vesicles declined as BODIPY and 1 diffused out of the vesicles, suggesting nanomechanical disruption of the vesicle bilipid membranes. A series of control molecules were used to exclude the possibility that the large fluorescence intensity drop in the vesicles containing the mixture of BODIPY and 1 was caused by the UV light induced photo-bleaching. The thermal effects due to the absorption of UV light by 1 was not responsible for the vesicle opening since a control molecule that has an even larger absorption coefficient at 365 nm than that of 1 did not show the loss of BODIPY fluorescence from the vesicles (FIG. 4).

Following the synthetic bilipid vesicle experiments, nanomechanical action upon live cells was studied using confocal microscopy aided by a super-resolution technique called Phase Modulation Nanoscopy. Applicants used two experimental methods. In the first method (Method A), the molecular motors were loaded into the cell media and the imaging was initiated within 5 minutes to 24 hours. In the second method, (Method B), the molecular motors were loaded into the cell media, incubated for 30 minutes to 24 hours, and then washed three times with fresh molecular motor-free media before imaging.

Figure 6A:
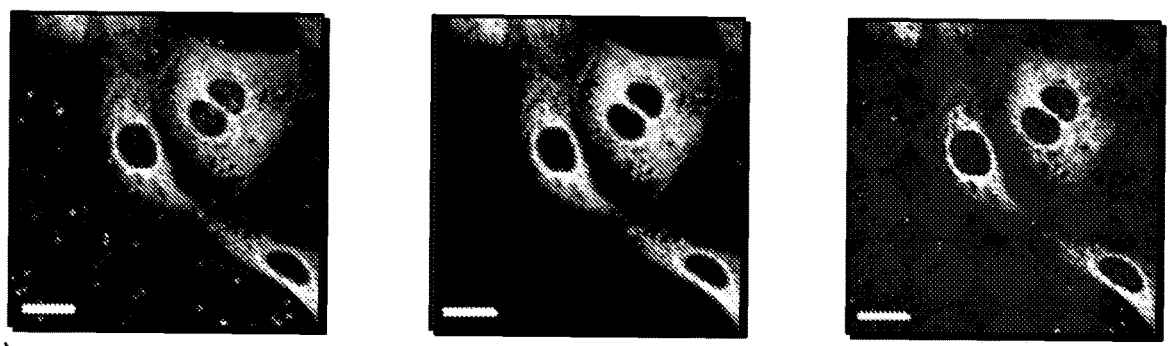
Figure 6B:
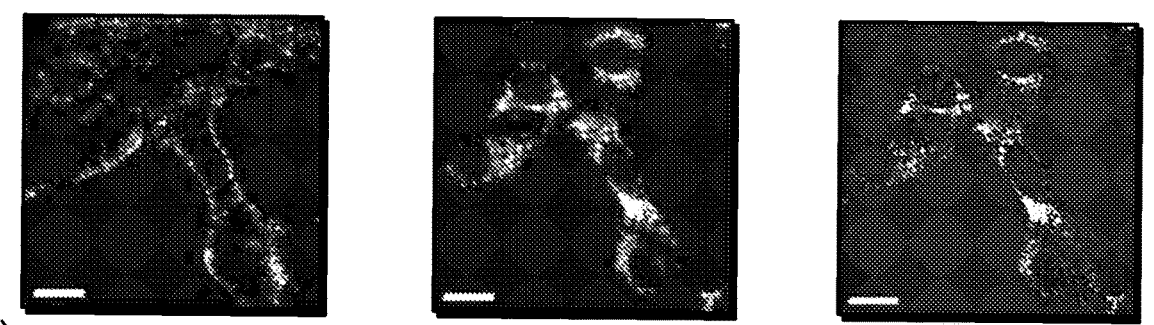

Applicants first studied the effect of the nanomachines on the cells without UV-light exposure. Using Method A, molecular machines 1 ($\lambda_{ex}$ 633 nm, $\lambda_{em}$ 650-680 nm for the pendant cy5 dyes) and 2 ($\lambda_{ex}$ 514 nm, $\lambda_{em}$ 530-580 nm for the pendant BODIPY dyes) do not induce accelerated necrosis when introduced to NIH 3T3 cells. However, due to 1 and 2 having well-pronounced visible fluorescence properties corresponding to the cy5 and BODIPY addends (FIG. 5 and Table 1, respectively), their intracellular uptake, motion or protein/organelle-assisted trafficking are clearly observed. The two luminescent compounds display very different localization patterns. Nanomachine 2 enters the cell and localizes in the mitochondria (FIG. 6A). Conversely, nanomachine 1, when introduced to cells, displays pit-like cell surface localization (FIG. 6B) and later, at 4 hour, small ~1 μm aggregates are seen inside the cytoplasm.

TABLE 1

Optical properties of molecules 1 and 2 in CHCl₃

| Compound | $\lambda_{abs(nm)}$ | $\lambda_{em\ (nm)}$ | $\Phi_f$ |
|---|---|---|---|
| 1 | 656 | 680 | 0.30[a] |
| 2 | 507 | 518 | 0.75[b] |

[a]Quantum yield was measured using zinc phthalocyanine as a reference, ($\Phi_f$ = 0.30 in benzene, $\lambda_{ex}$ = 630 nm).
[b]Quantum yield was measured using rhodamine 6G as a reference, ($\Phi_f$ = 0.94 in ethanol, $\lambda_{ex}$ = 474 nm).

These respective time-dependent localization patterns were observed to be constant within the applied 0.10-1.00 μM final nanomachine loading concentrations, suggestive of an active uptake mechanism. Applicants undertook a series of control experiments to confirm active molecular motor uptake and suspected endocytosis, using a range of nanomachine loading concentrations (0.10-1.00 μM, Method A) and incubation times of 5-60 minutes at 4° C., which is a temperature of general endocytosis inhibition.

The aforementioned studies reveal that there was no detectable localized fluorescence of 2 in the mitochondria or 1 on the cell surface. These experiments eliminate the possibility of passive concentration gradient-driven diffusion or static cell surface interactions of these nanomachines. Further strengthening this observation are the fluorescence intensity measurements where more than 99% of motors applied could be recycled from the wash solutions and re-collected during loading and imaging. Since the motors were not UV-activated, Applicants did not see accelerated cell death. Cell viability throughout these experiments remained at >90% and both fluorescent nanomachines 1 and 2 were found to be non-toxic in the applied time and concentration regimes.

Figure 6C:
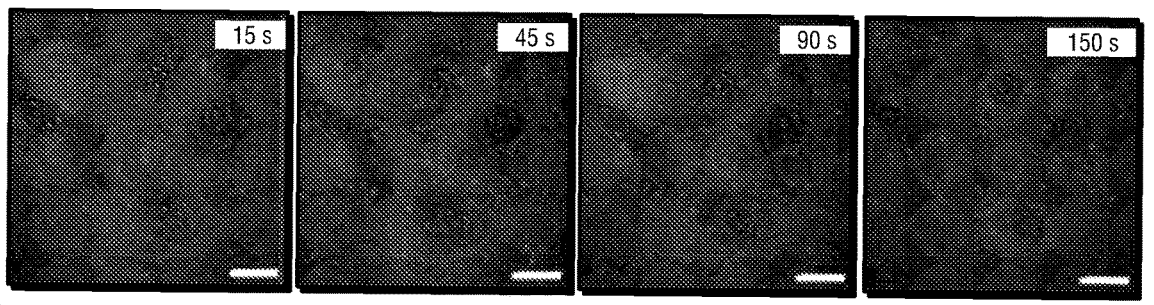
Figure 6D:
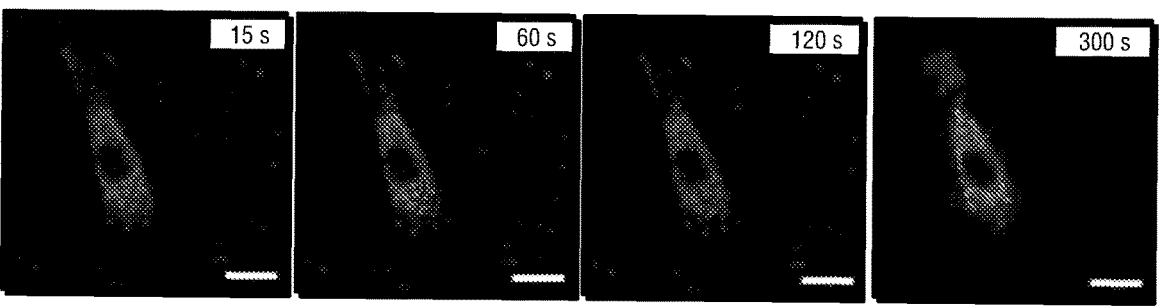

The NIH 3T3 cells in the presence of the nanomachines were then studied with concomitant UV activation. Upon UV-induced motor activation for 150 seconds (355 nm), 1, introduced by Method A, was found to cross the cell membrane, and it was internalized into cells in a time-dependent manner, displaying fast accelerated intracellular motion, compared to natural homeostatic cellular organelle movement in the absence of UV-nanomechanical activation (FIG. 6C). Combined controlled time and UV-exposure-dependent experiments indicate that the small aggregates of 1 inside the cytoplasm dissolve or burst with further increasing of fluorescence signal in the cytoplasm (FIG. 6D). Thus, nanomachine trafficking can be facilitated and precisely observed.

Figure 7A:
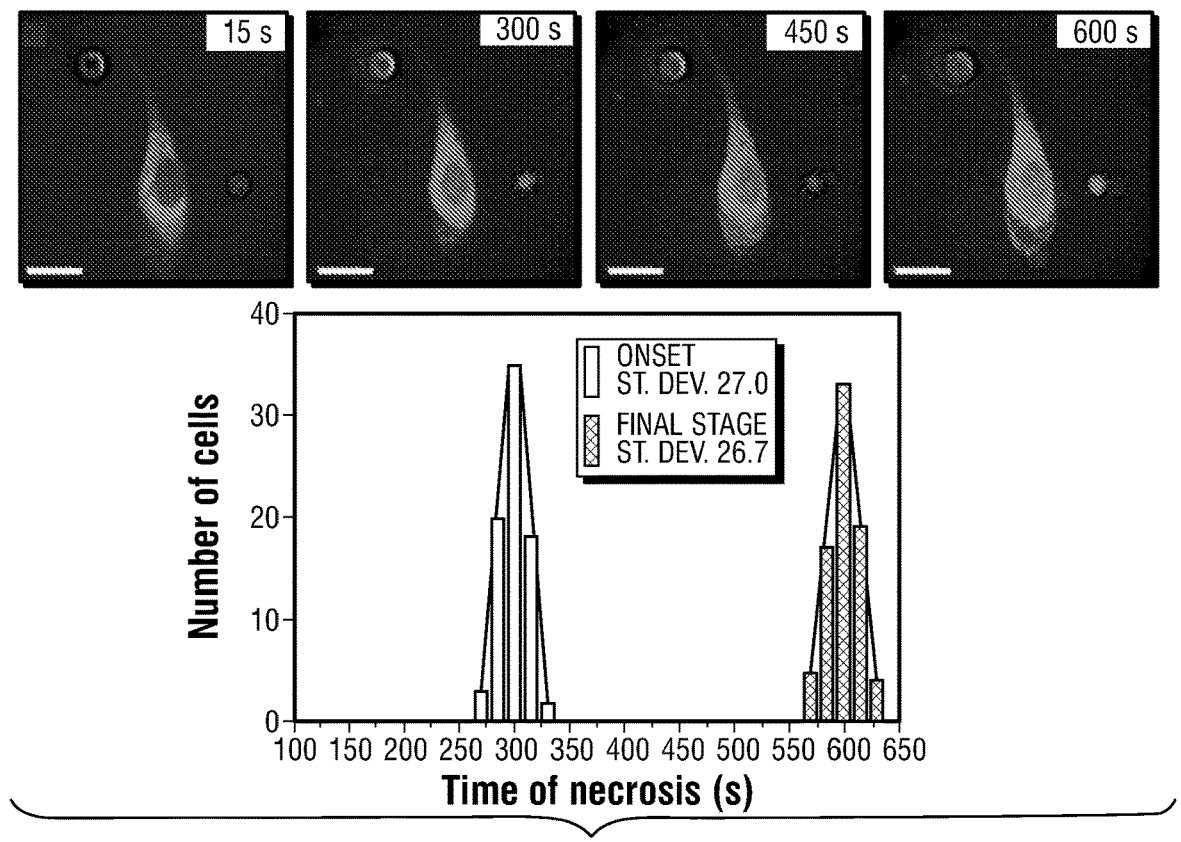

Next, Applicants used the smaller nanomachine, 3. Initial control experiments (blank) were performed without nanomachines being present. UV-induced (355 nm) PC-3 necrosis is not initiated until approximately scan 20 (corresponding to 300 second continuous scanning UV exposure, 400 nJ/voxel total dwell time), characterized by massive disruption and rupture of the mitochondrial network and subsequent well-pronounced auto-fluorescent signal detectable in the nucleoli and nucleus wall (FIG. 7A). This is observable by the nucleoli membrane permeabilization and DNA damage at the onset of necrosis. The UV-induced necrosis reaches final stages at approximately scan 40 (corresponding to 600 seconds) that is consistent with characteristic extracellular membrane rupture and homogenous cytosolic auto-fluorescence, indicating loss of cellular organelle boundaries.

Figure 7B:
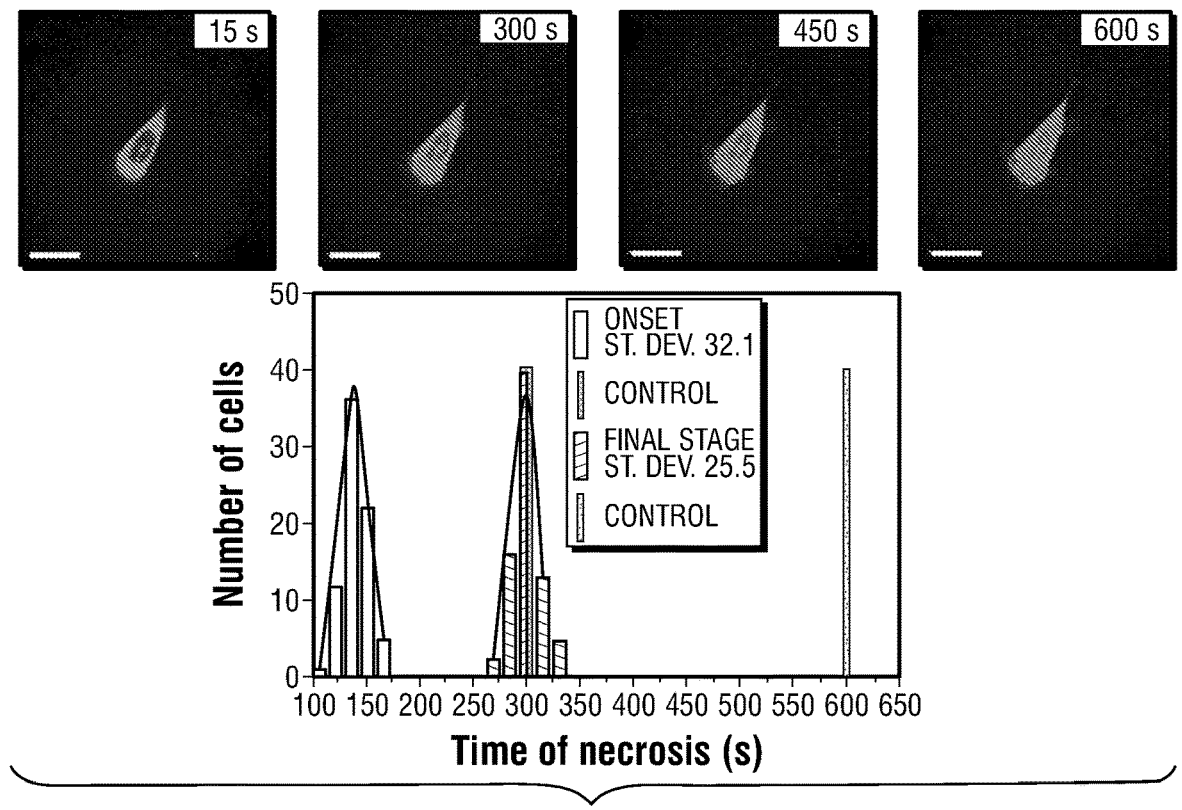

Conversely, visual signs of apoptosis involve cell shriveling and subsequent detachment from the cover-slip surface followed by fragmentation. Using 3 by Method A with both PC-3 and NIH 3T3 cell lines in the time- and UV-exposure-dependent in vitro microscopy experiments with the previously established standard experimental parameters and 355 nm laser exposure, >50% accelerated cell death (relative to UV-exposure without 3) is observed due to disruption of the cell membrane (FIGS. 7B and 8).

Well-pronounced fragmentation of the mitochondrial network is established between scan 8 and 10 (corresponding to 120 to 150 s, respectively) with extracellular membrane burst manifesting at scan 20 (300 seconds) (Table 2 and FIG. 8). This is confirmation of accelerated necrosis. Importantly, 3 was found to be non-internalizing prior to UV-activation. Onset of necrosis and internal cell organelle mitochondrial fragmentation or nucleolus damage is identical regardless of prior 2-4 hour incubation of the cells with 3 vs. adding 3 directly before UV-activation.

TABLE 2

Data sets for time of fluorescent nanomachine cell incorporation and for necrosis determinations.

| Compound | Cell Type | Method[a] | No. of FOV[b]/slide | Avg. No. of Cells/FOV | $N_{Total}$[c] | Time of Initial Necrosis[d] (s) | Time of Full Necrosis (s) | % acceleration for full necrosis[e] | Std. dev. (s)[f] |
|---|---|---|---|---|---|---|---|---|---|
| Blank | NIH 3T3 | A | 25/5 | 2.4 | 60 | 300 | 600 | 0 | 15 |
| Blank | PC-3 | A | 25/5 | 3.1 | 78 | 300 | 600 | 0 | 30 |
| Blank | CHO | A | 25/3 | 2.5 | 64 | 300 | 600 | 0 | 30 |
| 1 | NIH 3T3 | A | 27/5 | 2.6 | 70 | 300 | 600 | 0 | 15 |
| 2 | NIH 3T3 | A | 28/5 | 2.3 | 65 | 300 | 585 | 2.5 | 30 |
| 1 | NIH 3T3 | B | 25/5 | 2.6 | 65 | 300 | 600 | 0 | 30 |
| 2 | NIH 3T3 | B | 26/5 | 2.7 | 70 | 300 | 570 | 5 | 30 |
| 3 | NIH 3T3 | A | 30/6 | 2.2 | 66 | 150 | 300 | 50 | 30 |
| 3 | PC-3 | A | 28/6 | 2.7 | 76 | 135 | 300 | 50 | 30 |
| 4 | NIH 3T3 | A | 32/5 | 2.1 | 67 | 270 | 540 | 10 | 15 |
| 4 | PC-3 | A | 25/5 | 2.5 | 63 | 270 | 540 | 10 | 15 |
| 5 | NIH 3T3 | A | 22/4 | 2.7 | 60 | 300 | 600 | 0 | 15 |
| 5 | PC-3 | A | 25/4 | 2.4 | 60 | 300 | 600 | 0 | 15 |
| 6 | NIH 3T3 | A | 21/4 | 2.8 | 58 | 300 | 615 | 0 | 30 |
| 6 | PC-3 | A | 24/4 | 2.5 | 60 | 300 | 600 | 0 | 30 |
| 7 | NIH 3T3 | A | 27/4 | 2.4 | 65 | 150 | 390 | 40 | 30 |
| 7 | PC-3 | A | 24/4 | 2.8 | 67 | 165 | 360 | 35 | 30 |
| 8 | NIH 3T3 | A | 23/5 | 2.6 | 60 | 150 | 375 | 37.5 | 30 |
| 8 | PC-3 | A | 29/4 | 2.2 | 64 | 150 | 360 | 40 | 15 |
| 7 | NIH 3T3 | B | 32/5 | 2.0 | 64 | 165 | 390 | 40 | 30 |
| 7 | PC-3 | B | 25/5 | 2.6 | 65 | 180 | 390 | 35 | 30 |
| 8 | NIH 3T3 | B | 27/5 | 2.3 | 62 | 150 | 360 | 40 | 30 |
| 8 | PC-3 | B | 28/5 | 2.4 | 67 | 150 | 360 | 40 | 30 |
| 9 | NIH 3T3 | A | 24/5 | 2.7 | 65 | 300 | 570 | 5 | 30 |
| 9 | PC-3 | A | 25/5 | 3.0 | 75 | 150 | 360 | 40 | 30 |
| 9 | CHO | A | 23/5 | 3.1 | 71 | 300 | 585 | 2.5 | 30 |
| 10 | NIH 3T3 | A | 27/6 | 2.6 | 70 | 270 | 540 | 10 | 30 |
| 10 | PC-3 | A | 27/5 | 2.7 | 73 | 195 | 420 | 30 | 30 |
| 10 | CHO | A | 24/5 | 2.9 | 72 | 270 | 540 | 10 | 30 |
| 9 | NIH 3T3 | B | 25/5 | 2.8 | 70 | 300 | 600 | 0 | 15 |
| 9 | PC-3 | B | 32/6 | 2.3 | 74 | 180 | 390 | 35 | 30 |
| 9 | CHO | B | 26/4 | 2.8 | 72 | 285 | 570 | 5 | 30 |
| 10 | NIH 3T3 | B | 22/5 | 3.3 | 73 | 300 | 600 | 0 | 30 |

TABLE 2-continued

Data sets for time of fluorescent nanomachine cell incorporation and for necrosis determinations.

| Compound | Cell Type | Method[a] | No. of FOV[b]/ slide | Avg. No. of Cells/ FOV | $N_{Total}$[c] | Time of Initial Necrosis[d] (s) | Time of Full Necrosis (s) | % acceleration for full necrosis[e] | Std. dev. (s)[f] |
|---|---|---|---|---|---|---|---|---|---|
| 10 | PC-3 | B | 31/6 | 2.5 | 78 | 210 | 435 | 27.5 | 30 |
| 10 | CHO | B | 22/4 | 3.2 | 71 | 300 | 600 | 0 | 15 |
| NonMe-3 | PC-3 | A | 27/5 | 2.4 | 65 | 270 | 540 | 10 | 30 |

[a]Nanomachine loading method used before imaging. [b]FOV = field of view. [c]Each individual statistical analysis have been executed on N number of total cells per corresponding experiment (no data was ever excluded and all images were used without post-processing) according to a standard Gaussian (2-tailed) fit. [d]Reported are the averaged time of death. [e]The percentage is in acceleration. For example, 50% means cells die 50% faster when rotors are present with UV exposure verses UV upon blank cells, the latter meaning that no nanomachines are present. Zero percent means blank reference time or no observed acceleration in necrosis time. [f]Standard deviation is calculated for time of full necrosis where the minimum precision and experimental error, due to the nature of microscopic imaging sequence, is 15 s. No difference has been found between the standard deviation for initial or full time of necrosis within this experimental error. Initial necrosis or the onset of necrosis is determined when the mitochondrial network of the cell in the green channel, using mitochondrial autofluorescence, is dispersed evenly in the cytosol and the small nucleoli in the nucleus starts to become visible with higher than 10/255 contrast value. Full necrosis is determined when the cell membrane bursts showing observable lesions (cell organelle-free clear blebbing) on the cell membrane, and when PI is used the PI can be detected in nucleus at >10/255 contrast value. All statistical analyses have been undertaken using Origin2015 fitting to a Gaussian fit function $y = y0 + a/(w*sqrt(pi/(4*ln(2)))) * exp(-4*ln(2)*(x-xc)^2/w^2)$ using the Levenberg-Marquardt iteration algorithm. All standard deviations have been established from each individual fitting and presented on the corresponding relevant graph. These values are also tabulated alongside relevant descriptive statistical parameters and rounded up to the nearest 15 seconds.

Figure 7C:
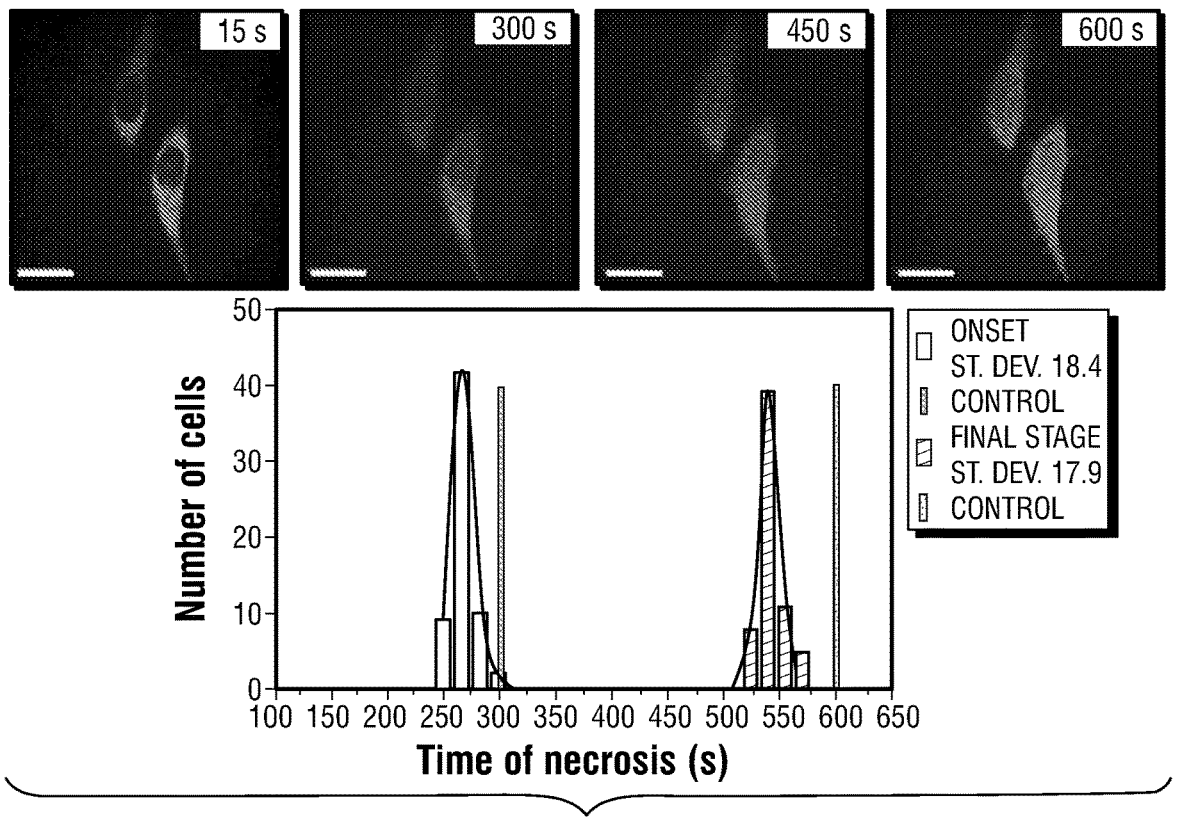

Molecular machine 4 was studied using identical pre-set study parameters and Method A on both PC-3 and NIH 3T3 cells, where UV-induced nanomechanical action caused necrosis only 10% earlier (Table 2) than the standard blank non-molecular motor containing reference cells (FIGS. 7C and 8). Nanomachine 4, bearing the larger aryl sulfonate moieties, might have been inhibited from having its rotor interact well with the cell membranes, or the addends themselves sterically encumbered their rotation near the membrane.

Figure 7D:
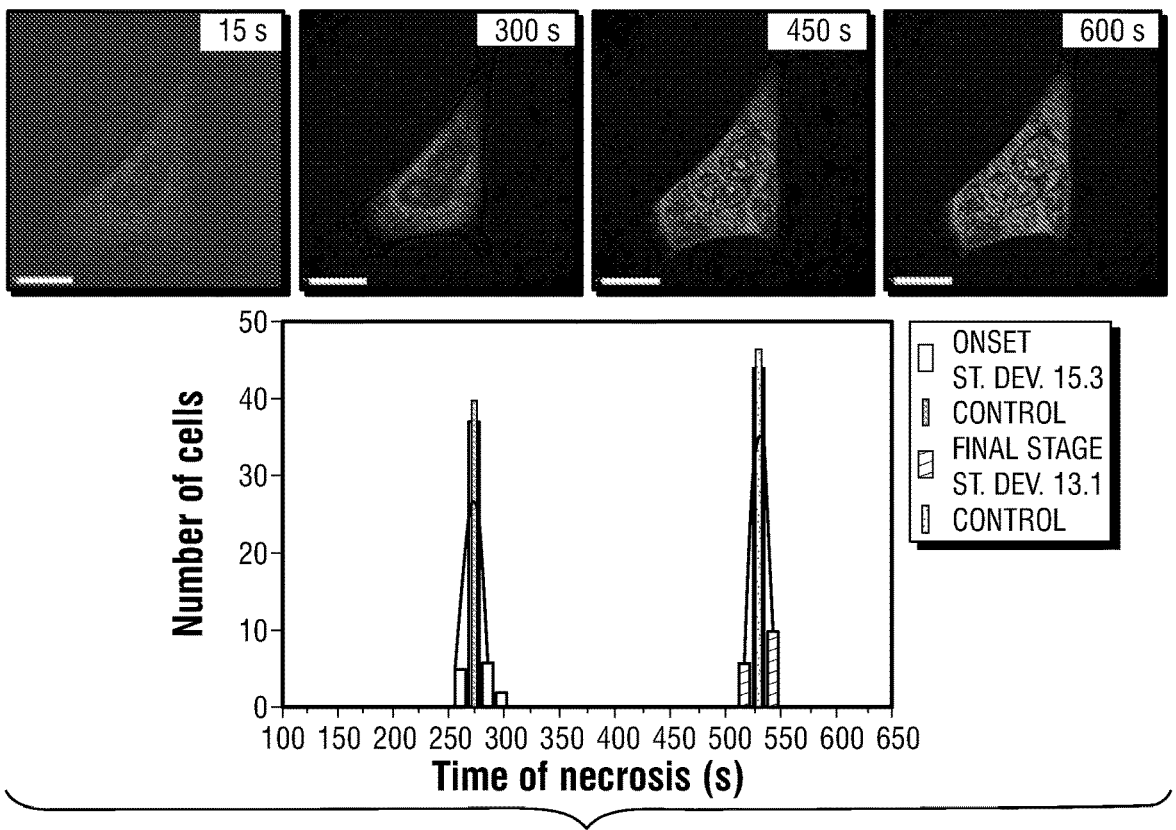
Figure 7E:
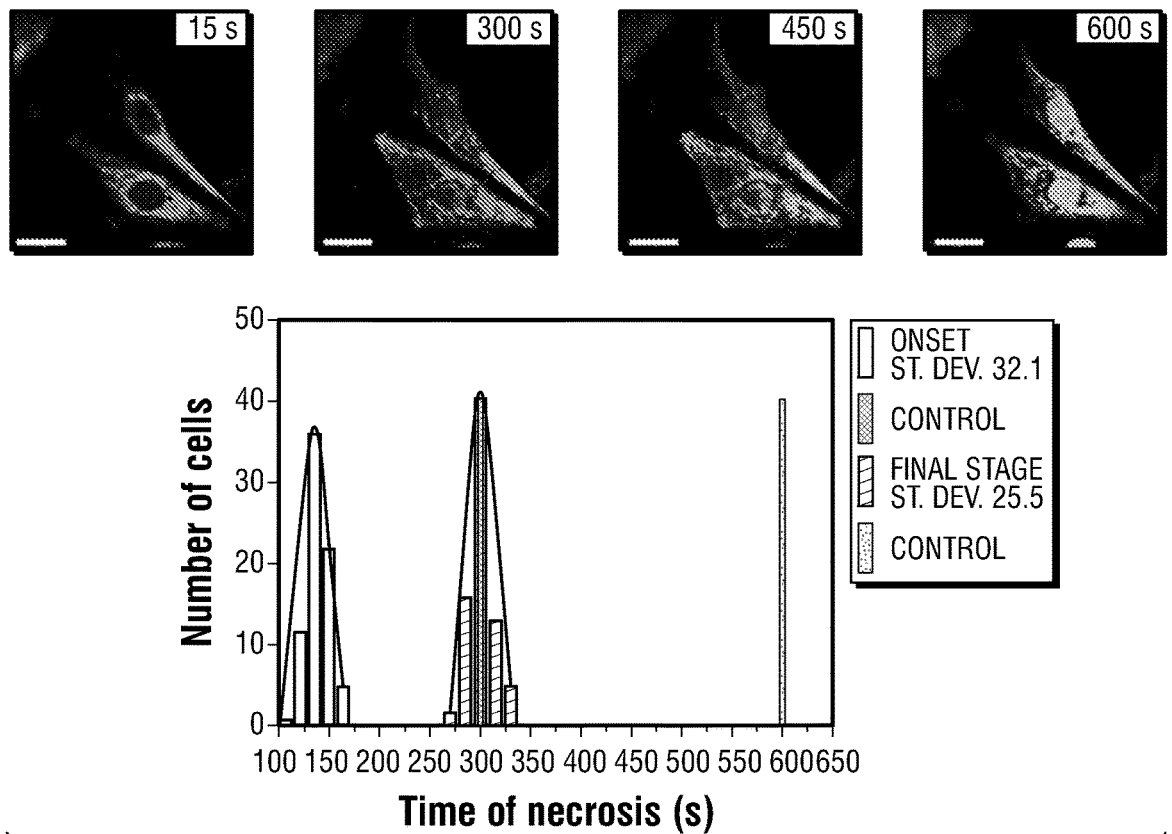
Figure 8A:
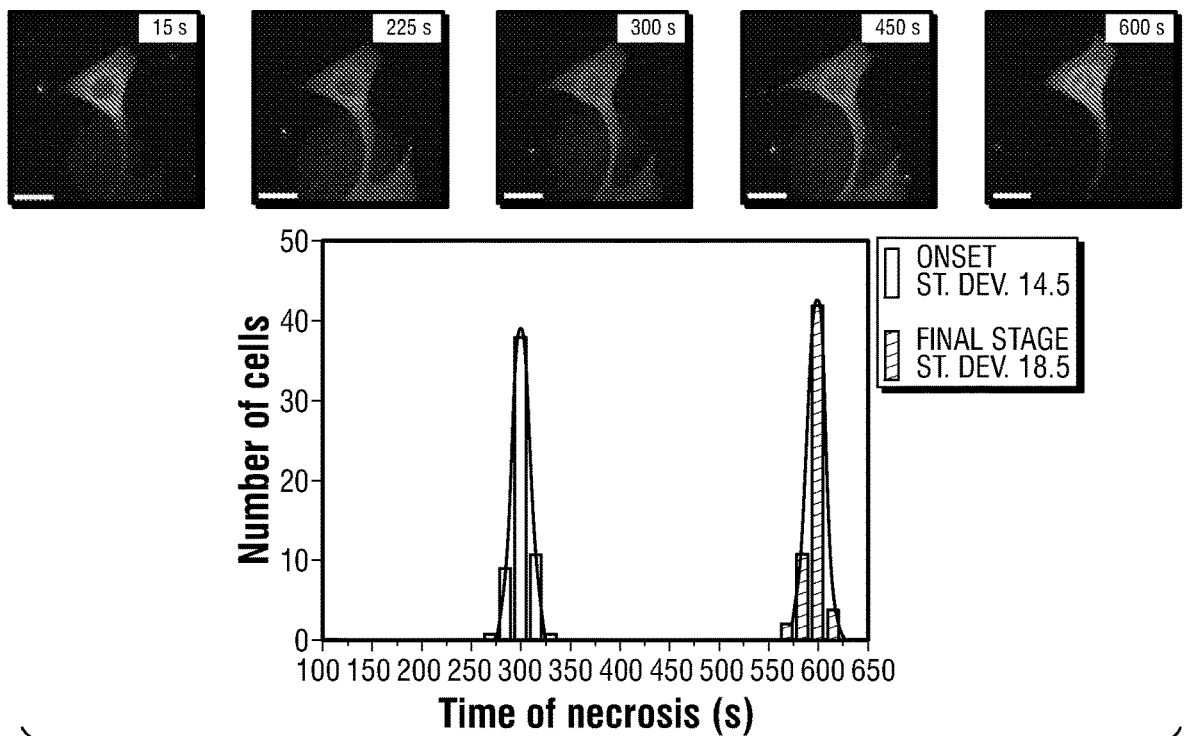
Figure 8B:
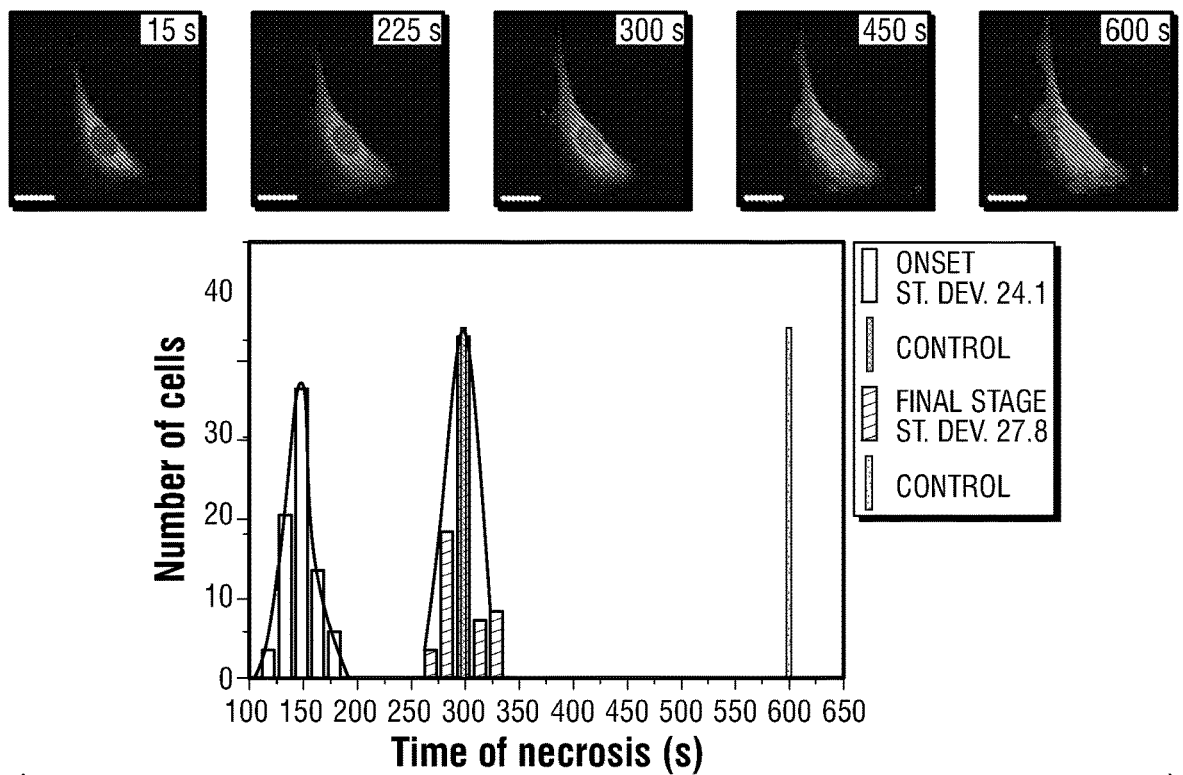
Figure 8C:
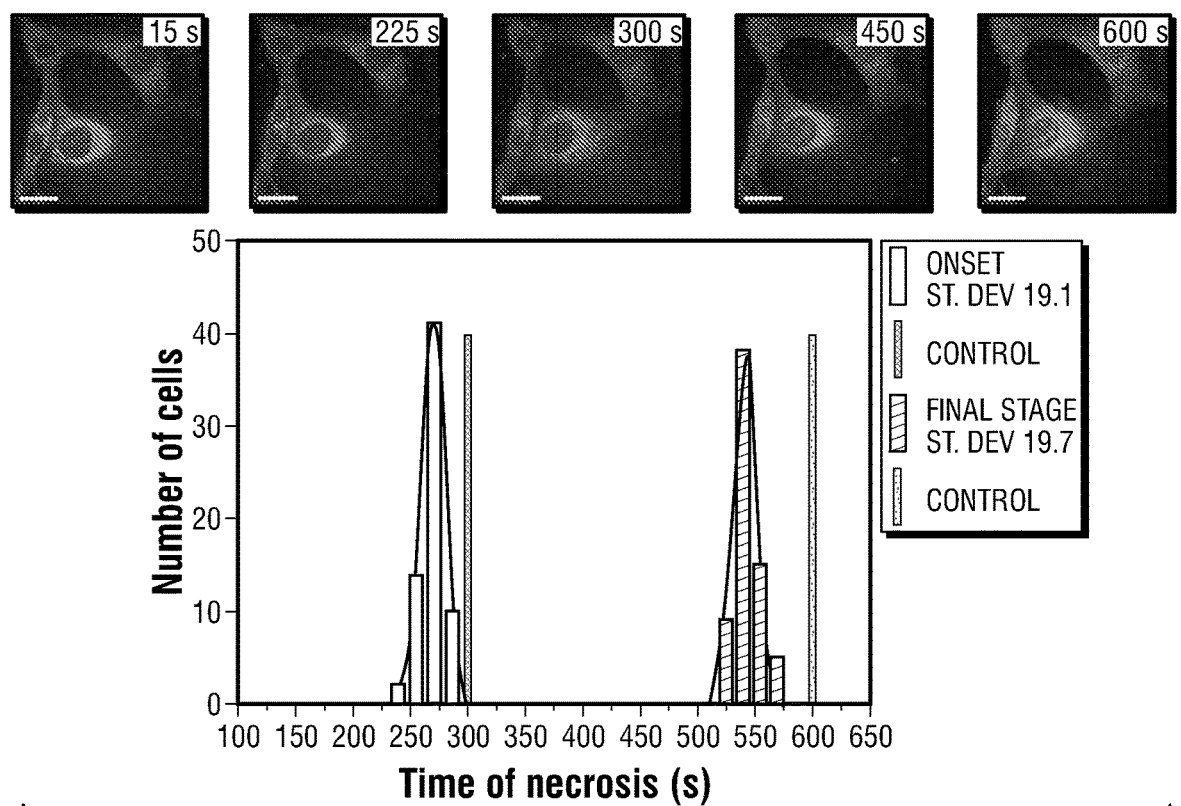
Figure 8D:
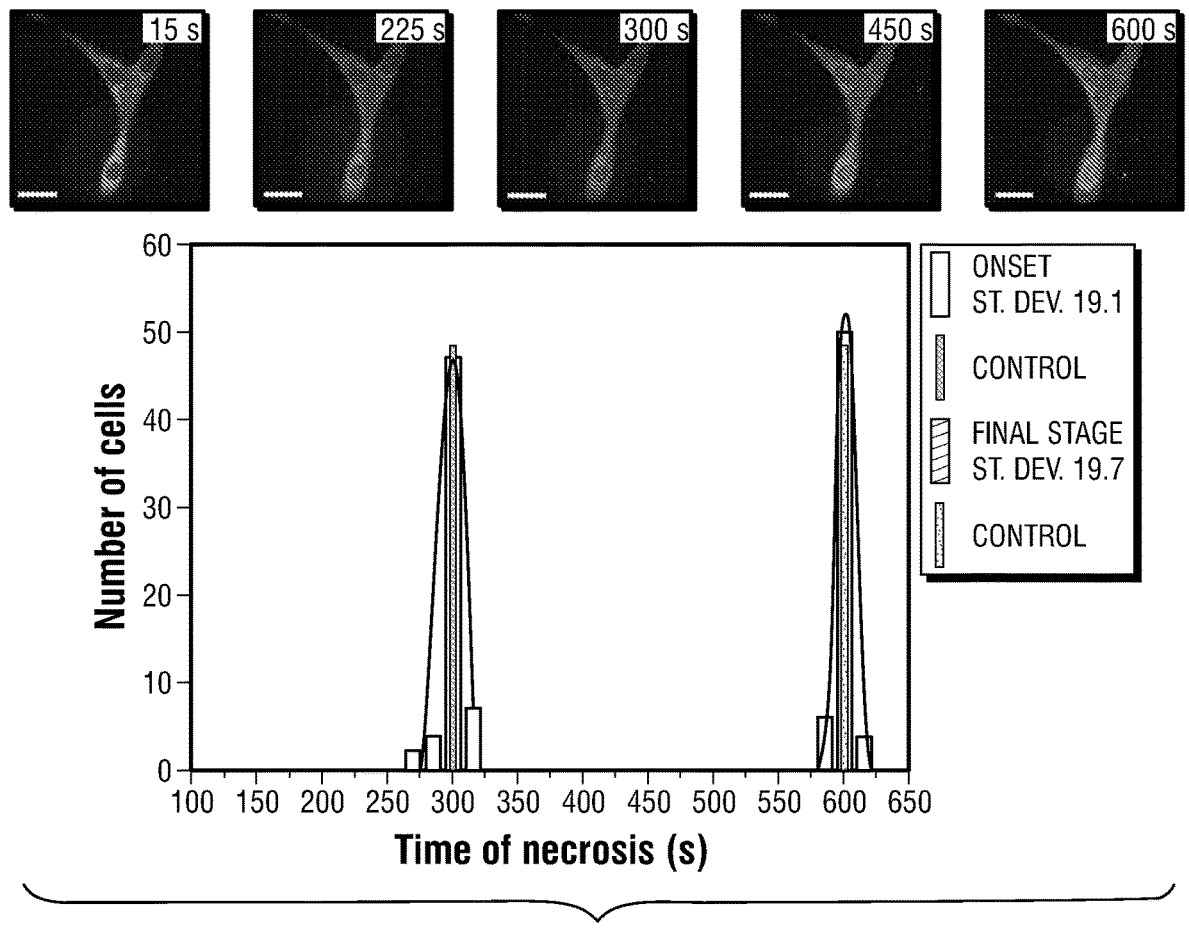

The rotor-free control molecule 5 was studied to ensure that the rotary action is preferred for the bilayer perturbations. Using Method A on both PC-3 and NIH 3T3 cells, which has the same homopropargylic alcohol stator moieties as does 3, control molecule 5 shows no effect on necrosis upon standardized UV-exposure (FIGS. 7D and 8). This further suggests that the accelerated cell death seen with 3 was not primarily due to the short exposure to UV light or subsequent thermal processes, similar to Applicants' earlier synthetic bilayer studies.

In order to further ensure that a fast rotary motion was preferred for nanomechanical opening of cells, another control (6) was used, which bears a 6-membered heterocyclic rotor that is nearly identical in molecular size and functionality to 3. However, 6 can only undergo cis-trans isomerization upon light activation at room temperature. This "flapping" action will occur without full rotation since that barrier (rotor crossing over the stator) requires 60° C. in the heterocyclic system. Even at 60° C., the rotation rate is only ~2 revolutions·h$^{-1}$ as opposed to the nearly identical molecular sized 3, which rotates at 2-3 MHz upon UV-activation at room temperature.

Compound 6 showed no enhanced necrosis in PC-3 or NIH 3T3 cells upon standardized UV-exposure (FIG. 9). Furthermore, a compound analogous to 3 but without the allylic methyl, which therefore can rotate but not unidirectionally, was only slightly faster than the motor-free system (FIG. 9). Therefore, the non-reciprocating unidirectional motor rotation is the highly preferred mode for these nanomachines that bear ultra-low Reynolds numbers, while progressing through the lipid bilayers.

Applicants further confirmed the nanomechanical opening and subsequent permeabilization of the membrane by adding a dye to the cell medium to assess its exogenous entry into the cells that might be afforded by nanomechanical action. Using PC-3 cells and 3, propidium iodide (PI, total concentration 0.10 μM) was introduced to the cell medium immediately prior to the time-dependent standardized imaging sequence. PI is a fluorescent intercalating agent that is not internalized by healthy cells, and it is non-toxic as shown by Applicants' molecular machine-free controls. Upon membrane disruption by nanomechanical action of 3 (FIG. 7E), PI enters the cell, travels to RNA- and DNA-rich areas where it intercalates and its excitation maximum subsequently displays ~30 nm bathochromic shift (from 535 to 565 nm) accompanied by a parallel hypsochromic emission maximum shift (from 617 nm to 600 nm).

Internalized RNA- and DNA-induced PI fluorescence is detected between 600 and 630 nm, allowing time-dependent light-activated molecular motor-induced cell permeabilization to be confirmed. Further, PI was used to follow membrane damage that is due to UV-activated nanomachine activity leading to necrosis. Since the entry of the PI is on a relatively short time scale compared to the time of cell division, the cell has insufficient time to adopt programmed cell death (apoptosis). This was confirmed using Annexin V, an apoptosis-specific stain where no relevant fluorescence from this dye was observed throughout the course of the experiments.

Considering the above UV-induced nanomechanical action, the peptide-bearing structures (7-10) were investigated to target specific cells for nanomachine-activated necrosis. The targeted cell line was PC-3 while NIH 3T3 and CHO cells were used as non-targeted controls. No selectivity was observed with the shorter peptide targeting moieties 7 and 8 (Table 2 and FIGS. 10-11), but the longer peptide sequences provided by 9 and 10 showed that the targeted PC-3 cells started to die of UV-activated motor-induced necrosis at 150 to 180 s, which corresponds to 40-50% faster onset than the molecular-motor-free UV-exposed cells or the untargeted molecular motor/cell combinations with NIH 3T3 and CHO cells (Table 2 and FIGS. 12-15).

Several notable features became apparent in nanomachine design. Pre-binding to or insertion into to the cell membrane is preferred. Just being present in the medium will not result in accelerated rotor-induced UV activated necrosis. With 3, all cell types showed accelerated activated necrosis presumably because the core on 3, with its smaller addends, interacted well with the membranes and it had minimal intermolecular steric interference while transporting through the membranes. The mono-addended core of 10 is better able to approach the membrane to sufficiently close proximity than the more sterically hindered 9, but still not as efficiently as the smaller 3. Finally, better transport through the membrane was realized with the less sterically encumbered 10 over 9. Doubling the large addends could sterically slow the membrane-transport.

The dynamic effects of nanomechanical action upon cellular membranes were then studied through the whole cell patch clamp electrophysiology of human embryonic kidney 293 cells (HEK293) commonly used for electrophysiological interrogation. Using Method B, the studies reveal that upon UV (355 nm) activation of molecular motor 3, inward ionic currents were produced consistent with hydrophilic pores forming in the cellular membranes. These inward currents were not observed in the absence of UV illumination or during UV illumination of non-rotor-bearing control 5 or UV illumination of untreated cells (FIG. 16A).

Inward currents produced during UV illumination of cells treated with 3 then continued even in the absence of UV illumination suggested that the cell membranes were irreversibly damaged. This was accompanied by induced morphological changes to the cells, such as membrane blebbing (FIG. 16B, white arrows), cell swelling and cytoplasmic degradation, all indicative of cell death. Although membrane blebbing occurs during apoptosis and necrosis, the large diameter of the blebs observed here (FIG. 16B; r=3.8±0.2 µm) matches necrosis as does the observed cell-swelling and the absence of apoptotic bodies. Consistent with Applicants' previously observed delayed morphological effects on the other cell lines studied above, inward currents in HEK293 cells appeared between 40 and 60 seconds after exposure to UV illumination. The slow rise in inward current during illumination suggests an accumulation of many small pores or increasing pore sizes.

Membrane rupture and pore formation under a tangential mechanical force have been studied theoretically and experimentally. Specific to the nanomechanical forces in Applicants' experiments, the actuation of the rotor will produce a tangential mechanical force perturbing the membrane structure. The UV photon energy ($\lambda$=365 nm) that actuates the motor is $E=hc/\lambda=5.4\times10^{-19}$ J.

If the entire amount of energy is used for the force generation, and the linear moving distance of the tip of the rotor is on the magnitude of s=1 nm, the generated force would be F=E/s=0.54 nN. The stress applied on the membrane would be 540 mN m$^{-1}$, far exceeding the requisite rupture stress for most bilipid membranes of 1-30 mN m$^{-1}$.

Even if Applicants consider that the nanomechanical action is pulsed and the membrane is more resistant to rupture, it is still theoretically sufficient to disrupt the membrane locally and to eventually compromise its integrity. This conclusion is also consistent with the energetics estimation. The estimated free energy for pore formation is tens of kJ mol$^{-1}$ using molecular dynamics simulations. The corresponding UV photon energy is sufficient to disrupt ~10 lipid molecules to form a transient pore. Further, the disruption effect of motor actuations might be cumulative. Considering that the rotors (~1 nm) are small relative to the thickness (7.5 to 10 nm) of the bilipid membranes, the rupture kinetics of the observed nanomechanical opening is not expected to be immediate. This is consistent with Applicants' experiments in this Example as well as the delayed membrane openings seen by others using probe-induced mechanical perturbations, accepting, however, that probe-tip perturbations are a vertical force model and hence considerably different than the tangential nanomechanical effects. Therefore, nanomechanical action can generate a concerted motion upon a 1-nm-long molecular rotor that will severely dislocate the membrane molecules, while other light absorbing molecules will merely dissipate the absorbed energy in random motions of atoms in the molecule, underscoring the efficacy of the nanomechanical effect for membrane disruption.

Example 1.1. Synthesis

The syntheses of the molecular machines were conducted as follows. Molecular machines 1, 2 and 7-10 were synthesized using copper(I)-catalyzed azide-alkyne cycloaddition between motor 11 and the corresponding alkynes 12, 13, DGEA-14 and SNTRVAP-15 (Scheme 1).

Scheme 1. Synthesis of molecular machines and structure of 16. The alkyne in R is converted to the heterocycle in the azide coupling with 11.

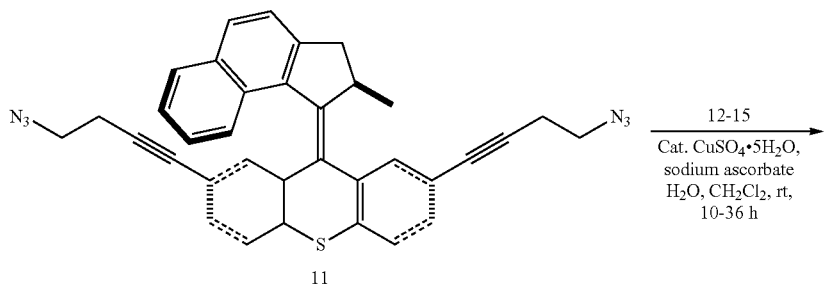

11

-continued
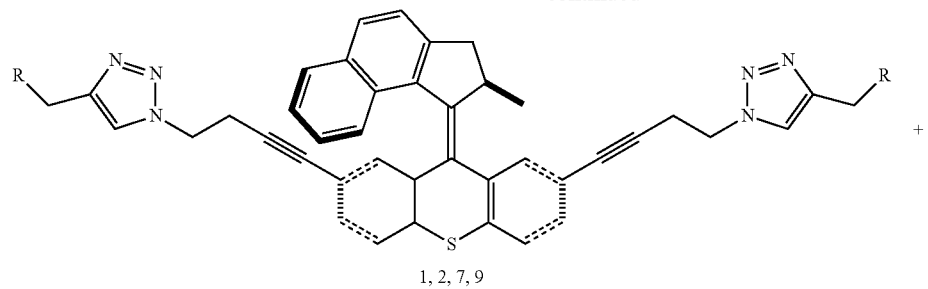
1, 2, 7, 9
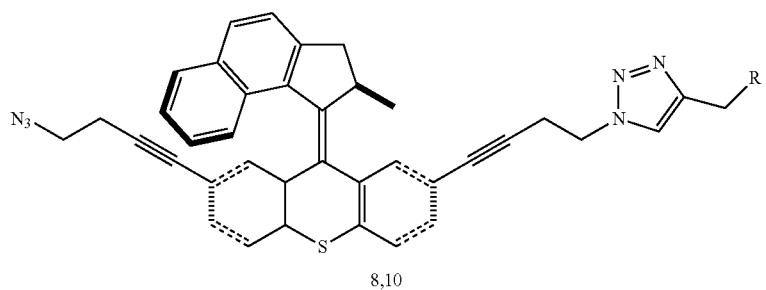
8, 10
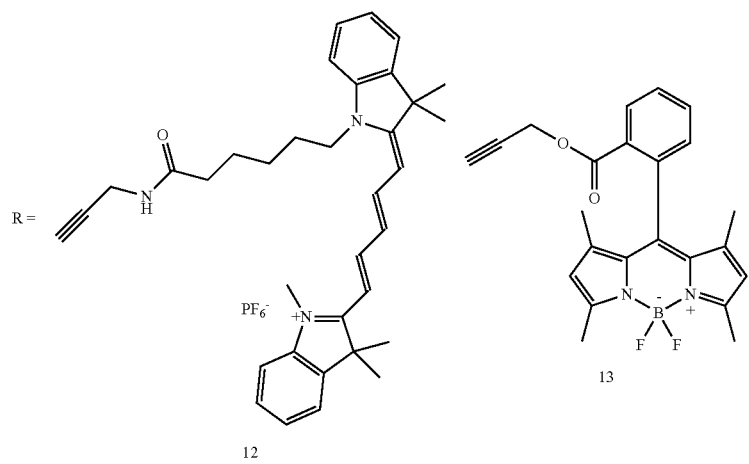
12
13
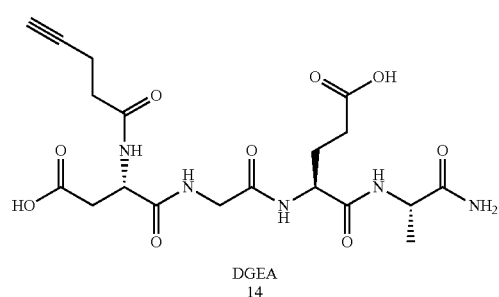
DGEA
14
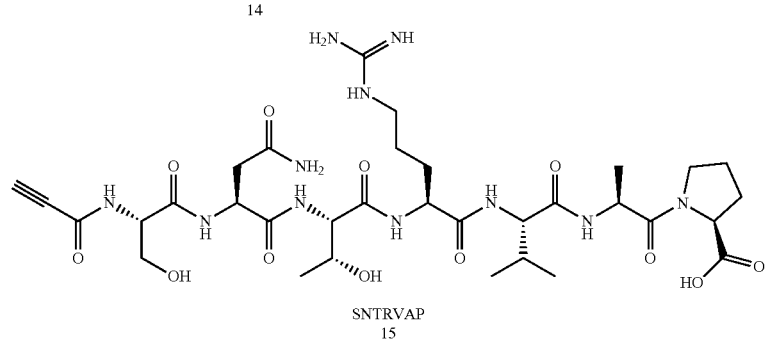
SNTRVAP
15

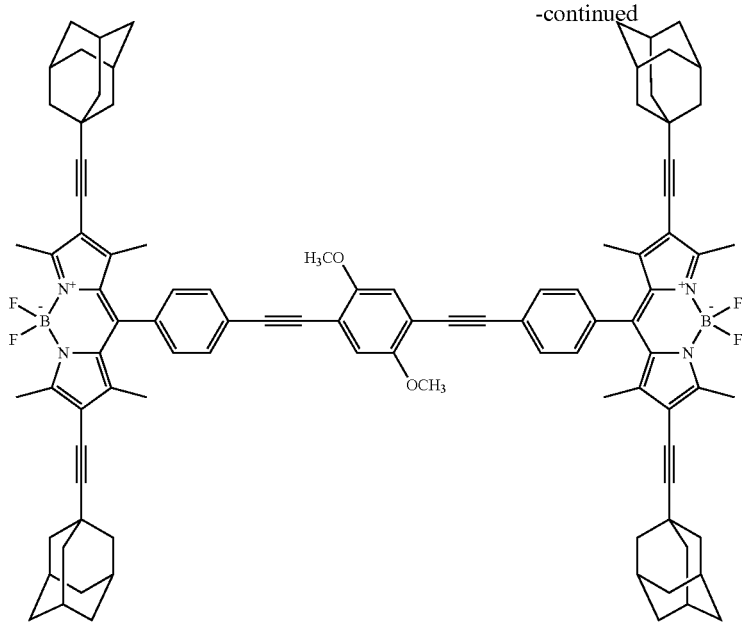

16

The synthesis of motors 3, 4 and controls 5, 6 and 16 were reported previously. All motors were synthesized as a racemic mixture of enantiomers. In addition, machines 8 and 10 were obtained as mixtures of the cis and trans diastereomers: each consisting of two enantiomers. Diastereomers of 8 were separated by HPLC but they interconvert in the presence of light. Therefore, the separation of the diastereomers of 10 was not attempted.

Example 1.2. General Methods

All glassware was oven-dried overnight prior to use. Reagent grade dichloromethane ($CH_2Cl_2$) was distilled from calcium hydride ($CaH_2$) under $N_2$ atmosphere. HPLC or spectroscopic grade water ($H_2O$), chloroform ($CHCl_3$) and acetonitrile ($CH_3CN$) were used for the HPLC purification or the measurement of the optical properties. All reactions were carried out under $N_2$ atmosphere unless otherwise noted. All other chemicals were purchased from commercial suppliers and used without further purification. The SNTR-VAP-alkyne was prepared by BioPepTek (Malvern, Pa., USA). Flash column chromatography was performed using 230-400 mesh silica gel from EM Science. Thin layer chromatography (TLC) was performed using glass plates pre-coated with silica gel 40 $F_{254}$ 0.25 mm layer thickness purchased from EM Science. $^1H$ NMR and $^{13}C$ NMR spectra were recorded at 400, 500 or 600 and 100, 125 or 150 MHz, respectively. Chemical shifts (δ) are reported in ppm from tetramethylsilane (TMS).

Example 1.3. Preparation of BODIPY-13

An oven-dried 50 mL round-bottom flask equipped with a stir bar was charged with BODIPY-acid 17 (360.1 mg, 0.973 mmol), propargyl alcohol (0.23 ml, 3.89 mmol), EDC (279.8 mg, 1.46 mmol), DMAP (11.9 mg, 0.097 mmol) and $CH_2Cl_2$ (11 mL). The mixture was stirred at ambient temperature for 17 hours and concentrated under vacuum. The residue was purified by column chromatography (silica gel, $CH_2Cl_2$) to yield 13 as a red solid (272.7 mg, 69%): $^1H$ NMR (600 MHz, $CDCl_3$) δ 8.13 (dd, $J_1$=7.9, $J_2$=1.3 Hz, 1H), 7.69 (td, $J_1$=7.5, $J_2$=1.3 Hz, 1H), 7.59 (td, $J_1$=7.7, $J_2$=1.3 Hz, 1H), 7.36 (d, J=7.6 Hz, 1H), 5.95 (s, 2H), 4.71 (d, J=2.4 Hz, 2H), 2.55 (s, 6H), 2.39 (t, J=2.5 Hz, 1H), 1.32 (s, 6H). $^{13}C$ NMR (150 MHz, $CDCl_3$) δ 164.87, 155.11, 141.98, 140.94, 136.29, 133.30, 131.19, 131.10, 129.78, 129.66, 129.35, 121.08, 75.19, 52.80, 14.60, 14.06. HRMS (ESI) m/z calculated for [M+Na]$^+$ $C_{22}H_{22}N_2O_2BF_2$ 429.1561, found 429.1556. The synthetic scheme is illustrated herein as Scheme 2.

Scheme 2. Synthesis of BODIPY-13

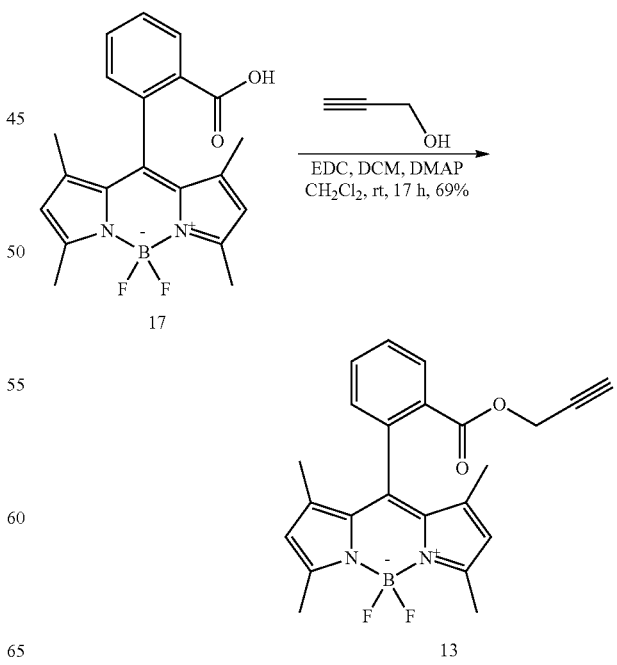

Example 1.4. Preparation of Molecular Machine 2

A 2 mL vial charged with motor diazide 11 (21.94 mg, 0.039 mmol), BODIPY dye 13 (35 mg, 0.086 mmol), CuSO$_4$.5H$_2$O(s) (0.97 mg, 0.0039 mmol) and sodium ascorbate (1.62 mg, 0.0117 mmol) was sealed with a rubber septum. A well-degassed mixture of CH$_2$Cl$_2$ (0.1 mL) and water (0.1 mL) was added to the vial, and the vial was shaken by a wrist-action shaking machine for 36 hours. The mixture was partitioned between CH$_2$Cl$_2$ (5 mL) and water (5 mL). The organic phase was dried over anhydrous MgSO$_4$, filtered, and the filtrate was concentrated under vacuum. The crude product was purified by preparative TLC (silica gel, 4% MeOH in CH$_2$Cl$_2$) to afford the desired 2 as an orange solid (45 mg, 85%): $^1$H NMR (600 MHz, CD$_3$CN) δ 8.00 (dd, J$_1$=7.9, J$_2$=1.1 Hz, 2H), 7.85-7.79 (m, 2H), 7.79-7.76 (m, 1H), 7.71 (s, 1H), 7.69-7.62 (m, 2H), 7.57-7.51 (m, 3H), 7.51-7.46 (m, 2H), 7.39-7.29 (m, 3H), 7.24-7.19 (m, 2H), 7.00 (dd, J$_1$=8.1, J$_2$=1.8 Hz, 1H), 6.84 (ddd, J$_1$=8.2, J$_2$=6.6, J$_3$=1.3 Hz, 1H), 6.77 (d, J=8.4 Hz, 1H), 6.59 (d, J=1.7 Hz, 1H), 6.02 (s, 1H), 6.01 (s, 2H), 5.99 (s, 1H), 5.27 (s, 2H), 5.14 (d, J=3.9 Hz, 2H), 4.58 (t, J=6.5 Hz, 2H), 4.36-4.30 (m, 1H), 4.30-4.24 (m, 1H), 4.20 (q, J=6.7 Hz, 1H), 3.68 (dd, J$_1$=15.33, J$_2$=6.11, 1H), 3.03 (t, J=6.5 Hz, 2H), 2.71 (t, J=6.5 Hz, 2H), 2.63 (d, J=15.5 Hz, 1H), 2.49 (s, 6H), 2.48 (s, 3H), 2.47 (s, 3H), 1.25 (s, 6H), 1.24 (s, 3H), 1.23 (s, 3H), 0.69 (d, J=6.9 Hz, 3H); $^{13}$C NMR (150 MHz, CD$_3$CN) δ 165.77, 165.76, 155.38, 155.33, 148.01, 147.62, 143.11, 142.69, 142.66, 142.60, 142.16, 140.66, 138.08, 136.08, 136.00, 135.97, 134.72, 134.08, 134.06, 133.61, 131.62, 131.57, 131.28, 131.10, 131.01, 130.30, 130.27, 130.24, 130.17, 130.15, 129.83, 129.12, 128.71, 128.36, 128.33, 127.27, 125.88, 125.57, 124.94, 124.75, 124.72, 124.67, 122.11, 121.74, 121.60, 87.21, 86.41, 82.76, 82.31, 59.12, 58.99, 49.19, 48.98, 39.88, 38.47, 21.60, 21.31, 19.09, 14.35, 13.84, 13.82. HRMS (ESI) ink calculated for [M+Na]$^+$ C$_{81}$H$_{68}$N$_{10}$O$_4$B$_2$F$_4$S 1397.5184, found 1397.5210. The formed structure is illustrated herein as Scheme 3.

Example 1.5. Preparation of Peptide-14

DGEA-alkyne peptide 14 was synthesized manually using standard solid-phase Fmoc protocols with Fmoc-amino acids and 4-pentynoic acid and was prepared as a C-terminal amide using Rink amide MBHA resin. Each acylation with Fmoc-amino acids or 4-pentynoic acid was performed using HATU (4 equiv) and N,N-diisopropylethylamine (DIPEA) (4 equiv) for 45 minutes in dimethylformamide (DMF) at room temperature, followed by Fmoc deprotection with 20% piperidine in DMF. DMF was used to wash the resin between each acylation and deprotection step. Cleavage from the resin was conducted by treatment with a mixture of 95% trifluoroacetic acid, 2.5% water, and 2.5% triisopropylsilane (TIPS) at room temperature for 2 hours. The peptide was purified by reverse-phase HPLC and characterized by ESI-MS. HPLC Purification: Reverse-phase HPLC purification of 14 was performed on a Shimadzu CBM-20A instrument with Phenomenex Jupiter 4µ Proteo 90A (250×15 mm preparative) and Phenomenex Jupiter 4µ Proteo 90A (250×4.6 mm analytical) columns. The columns were eluted with a gradient of acetonitrile in water (10-60%) (flow rates of 8 mL/min and 1 mL/min for preparative and analytical columns, respectively). Trifluoroacetic acid (0.1%) was added to all eluents. The formed structure is illustrated herein as Scheme 4.

Scheme 4. Structure Peptide 14.

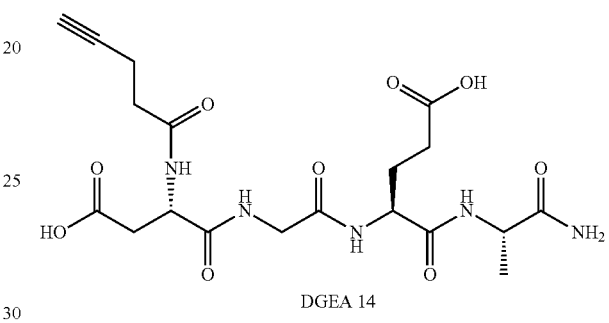

DGEA 14

Example 1.6. Preparation of Motor Peptides 7 and 8

A 1.5 mL Eppendorf tube charged with motor diazide 11 (2.0 mg, 0.0035 mmol), peptide-14 (2.46 mg, 0.0052 mmol), CuSO$_4$.5H$_2$O(s) (0.17 mg, 0.0007 mmol), sodium ascorbate (0.24 mg, 0.0017 mmol), and anhydrous DMF (60 µL) was bath sonicated for 10 hours at room temperature. After sonication, the crude product was purified by HPLC to afford 7 (2.5 mg, 47%) and 8 (2.0 mg, 53%) as white solids. HPLC Purification: Separation of 7 and 8 was performed using a reverse-phase peptide column (XBridge BEH300 prep C18, Part No. 186003628). Sample preparation involved dissolving the reaction mixture into 1 mL of a 1:1 mixture of H$_2$O and CH$_3$CN, followed by vigorous shaking and sonication. The mixture was then centrifuged at 14,000 rpm for 10 minutes to obtain a fully transparent supernatant for HPLC injection. This process was repeated on the pellet Scheme 3. Molecular Machine 2.

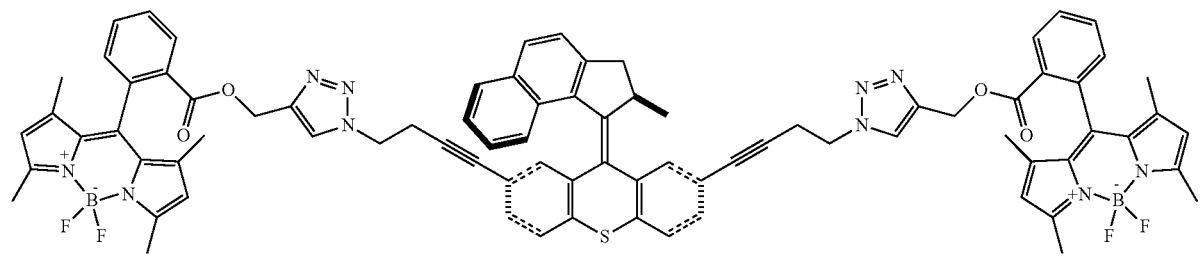

to extract as much product as possible, until the obtained supernatant resulted in no peaks in the HPLC chromatogram. A gradient elution system, containing 0.1% TFA in water and ACN, ramping from 20% to 90% of acetonitrile over 23 minutes with a flow rate of 2.5 mL/min at 40° C. was employed, which resulted in a baseline resolution of chromatogram peaks. The peaks were identified using a Micro-ToF ESI Mass Spectrometer. ESI m/z calculated for 7 $[M]^+$ $C_{73}H_{80}N_{16}O_{18}S$ 1502.6, found 1502.6. ESI m/z calculated for 7 $[M]^+$ $C_{54}H_{53}N_{11}O_9S$ 1032.4, found 1032.3. The structures of the peptides are illustrated herein as Scheme 5.

Scheme 5. Motor peptides 7 and 8.

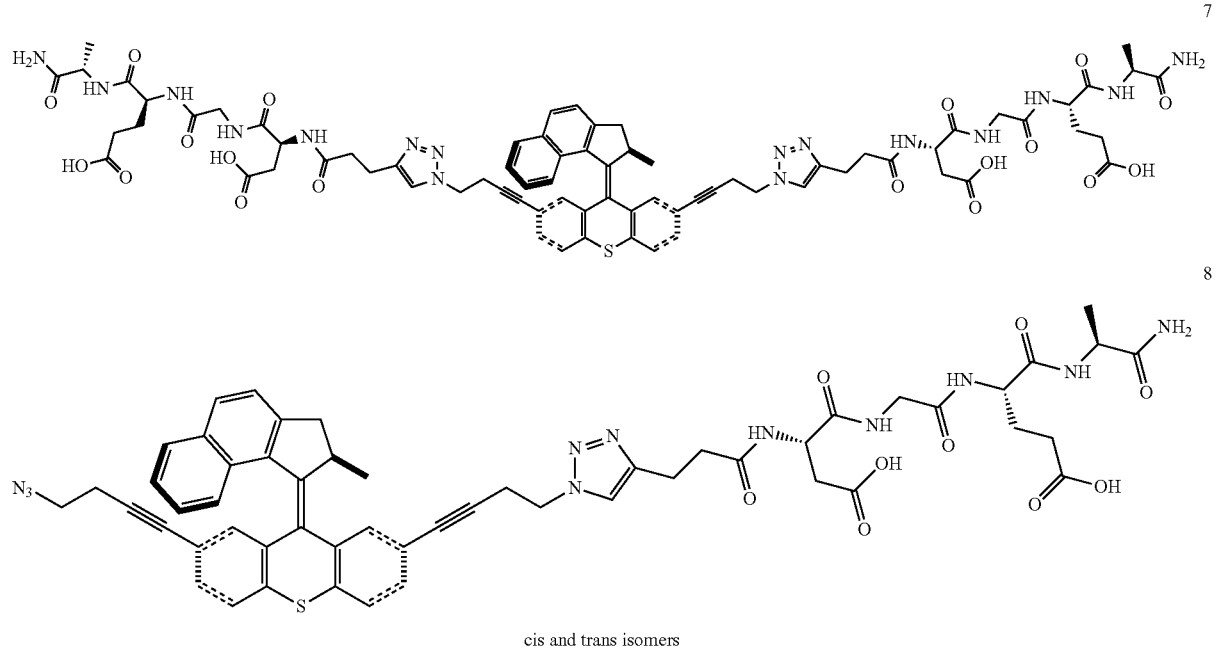

cis and trans isomers

Example 1.7. Preparation of Motor Peptides 9 and 10

A 1.5 mL Eppendorf tube charged with motor diazide 11 (1.88 mg, 0.00334 mmol), peptide-13 (4.0 mg, 0.00502 mmol), $CuSO_4 \cdot 5H_2O(s)$ (0.17 mg, 0.0007 mmol), sodium ascorbate (0.24 mg, 0.0017 mmol), and anhydrous DMF (70 μL) was sonicated for 10 hours at room temperature. After sonication, the crude product was purified by HPLC to afford 9 (2.4 mg, 43%) and 10 (2.0 mg, 57%) as white solids. HPLC Purification: Separation of 9 and 10 was performed using a reverse-phase peptide column (XBridge BEH300 prep C18, Part No. 186003628). Sample preparation involved dissolving the reaction mixture into 1 ml of 2:1 mixture of $CH_3CN$ and $(CH_3)_2SO$, followed by vigorous shaking and sonication. The mixture was then centrifuged at 14,000 rpm for 10 minutes to obtain a fully transparent supernatant for HPLC injection. This process was repeated on the pellet to extract as much product as possible, until the obtained supernatant resulted in no peaks in the HPLC chromatogram.

A gradient elution system, containing 0.1% TFA in water and ACN, ramping from 20% to 100% of acetonitrile over 24 minutes with a flow rate 1.5 mL/min at 50° C. was employed, which resulted in a baseline resolution of chromatogram peaks. The peaks were identified using a MALDI Mass Spectrometer using CHCA matrix. MALDI m/z calculated for 9 $[M+H]^+$ $C_{101}H_{133}N_{28}O_{24}S$ 2153.97, found 2154.50. MALDI m/z calculated for 9 $[M+H]^+$ $C_{68}H_{80}N_{17}O_{12}S$ 1358.5893, found 1358.990. The structures are illustrated herein as Scheme 6.

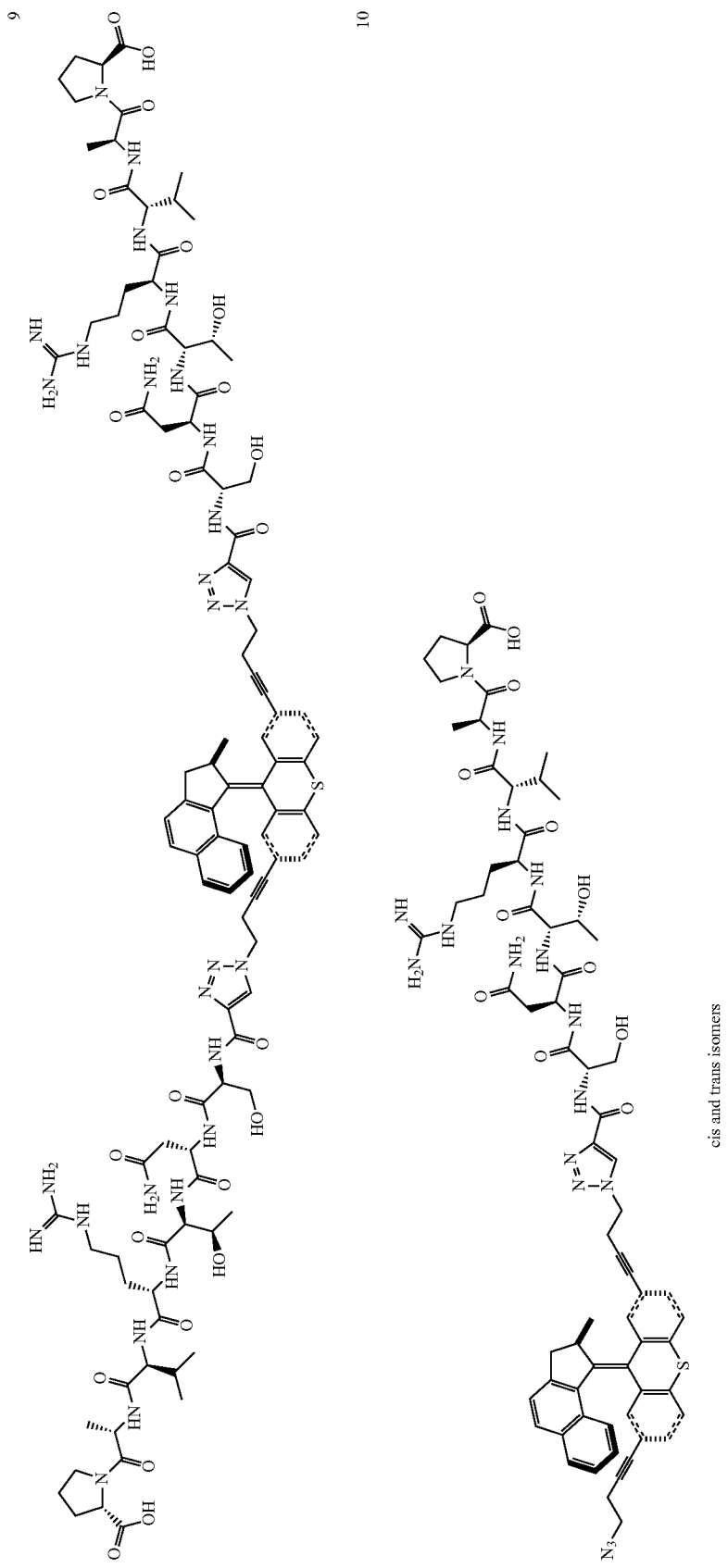
Scheme 6. Motor peptides 9 and 10.
cis and trans isomers

Example 1.8. Monitoring of Isomer Interconversion of 8

The monitoring of isomer interconversion of 8 is illustrated herein as Scheme 7.

according to their initial intensities and analyzed the percent intensity drop. The error bar stands for the standard deviation of the normalized intensities. The first data point does not have an error bar. The average fluorescence intensity drop of 20 vesicles was 70±6% (mean±standard deviation)

Scheme 7. Monitoring of isomer interconversion of 8.

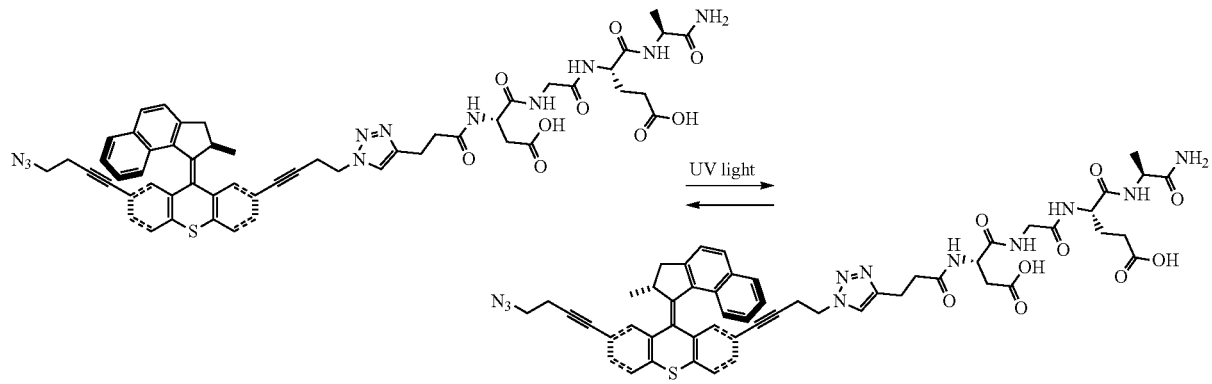

Example 1.9. Preparation and Opening of Synthetic Lipid Membranes

Premixed and dried synthetic phospholipid blend [1,2-dioleoyl-sn-glycero-3-phosphoethanolamine (DOPE): 1,2-dioleoyl-sn-glycero-3-phospho-L-serine (DOPS): 1,2-dioleoyl-sn-glycero-3-phosphocholine (DOPC) at a ratio of 5:3:2] were stored in a −20° C. freezer before use. To prepare the large unilamellar vesicles (LUVs), 5 mL 0.5× phosphate buffered saline (PBS) at pH 7.4 was added to swell the lipids solution (lipid concentration was 0.25 mg/mL). Then 7 μL of 210μ M BODIPY dye and 2 μL of 50μ M 1 (or 16 in the control experiments) were added to the solution. After incubation for 1 hour at room temperature with occasional vortexing, the lipids formed a cloudy suspension. The suspension was extruded more than 20 times with a mini-extruder (Avanti Polar Lipids) assembled with a polycarbonate membrane having a pore diameter of 600 nm. The resulting clear LUVs suspension was used immediately. The vesicles were then immobilized on a piece of cover-glass. Excessive BODIPY and 1 were washed off using fresh 0.5×PBS before the releasing experiments. The vesicles were then observed using a home-build confocal fluorescence microscope at 488 nm excitation and 535±50 nm emission.

Due to the highly non-polar nature of compound 1, it prefers to be sorbed in the bilipid membrane (FIG. 3). FIGS. 4A-D show that both BODIPY and compound 1 were localized in the vesicle. The vesicles were then immobilized on a piece of cover-glass for the UV activation and releasing experiments. The UV light was provided by a UV LED at 365 nm with an intensity of ~10 W·cm$^{-2}$ and analysis was done from 0 to 10-15 minutes. The fluorescence intensity of the BODIPY dye molecules in single vesicles was monitored using a confocal fluorescence microscope by continuously scanning a small area (20×20 μm$^2$).

As the UV illumination time increased from 0 to 15 minutes, the fluorescence intensity of the vesicles became dimmer (FIG. 4E). FIG. 4F shows the normalized fluorescence intensity drop of 20 vesicles from 6 different sets of movies. Since the absolute intensity of the vesicles varied from vesicle to vesicle, Applicants normalized all the traces in the first 15 minutes of UV exposure. This is an observation based on many motor and dye molecules on individual vesicles. Even though the "gate" opening process is fast, the loss of dye molecules and their corresponding fluorescence is gradual and continuous, spanning a period as long as ~15 minutes.

To exclude the possibility that the large fluorescence intensity drop was caused by (1) the UV light bleaching on BODIPY molecules, and (2) the thermal effect due to the absorption of UV light by 1, Applicants also performed a control experiment where 1 was replaced by 16 with the same concentration in the vesicles. 16 was used because it has a larger absorption coefficient at 365 nm than that of compound 1.

Compound 16 has two conjugated BODIPY molecules embedded in its molecular structure. However, its excitation and emission are both red-shifted by ~70 nm as compared to those of isolated BODIPY molecules. Thus, its fluorescence is negligible to that from the isolated BODIPY molecules used as the probes when excited at 488 nm and collected at 535±25 nm.

FIGS. 4G-H show that compound 16 was localized in the vesicles. The fluorescence image of compound 16 was collected in the epi-fluorescence mode using 545±30 nm excitation and 605±55 nm emission. As a contrast, the fluorescence intensity drop of the BODIPY in 16-attached vesicles monitored in the confocal fluorescence mode (488 nm excitation and 535±25 nm emission) was much slower than in the 1-attached vesicles (FIGS. 4I-J). The average fluorescence intensity drop from 20 selected vesicles (from 5 sets of movies) was 9%±20% (mean±standard deviation) for the first 15 minutes UV light exposure. Thus, compound 1 disturbs the lipid membrane upon UV-activation through a nanomechanical effect, which allows smaller BODIPY dye molecules to pass through the membrane.

Example 1.10. Live Cell Cultures Studies

A detailed investigation of the cellular behavior of each complex was conducted using PC-3, NIH 3T3, and CHO cell lines using fluorescence and laser scanning confocal microscopy. These cell lines were sourced from ATCC (NIH 3T3 CRL-1658, PC-3 CRL-1435 and CHO(-K1) CCL-61) and have been established and maintained in a category 2 cell culture facility according to established standardized protocol for 12 months. The cells have been periodically monitored for *mycoplasma* contamination.

PC-3 has only been identified to cross contaminate other prostate adenocarcinoma cell lines but the source original PC-3 cell line has not been identified to be cross contaminated with any other cell line.

Cells were maintained in exponential growth as monolayers in F-12/DMEM (Dulbecco's Modified Eagle Medium) 1:1 that was supplemented with 10% fetal bovine serum (FBS). Cells were grown in 75 $cm^2$ plastic culture flasks, with no prior surface treatment. Cultures were incubated at 37° C., 10% average humidity and 5% (v/v) $CO_2$. Cells were harvested by treatment with 0.25% (v/v) trypsin solution for 5 minutes at 37° C. Cell suspensions were pelleted by centrifugation at 1000 rpm for 3 minutes, and were re-suspended in fresh medium by repeated aspiration with a sterile plastic pipette.

Microscopy cells were seeded in untreated iBibi 100 µL live cell channels and allowed to grow to 40% to 60% confluence, at 37° C. in 5% $CO_2$. At this stage, the medium was replaced and cells were treated with the studied nanomachines and co-stains as appropriate, with 0.1% DMSO (as detailed above) present in the final imaging medium. For live cell imaging, DMEM/F12 media (10% FBS) lacking phenol red was used from this point onwards. Following incubation, where Method B was used, the channels were washed with live cell imaging media and imaged using a purpose build incubator housing the microscope maintaining 37° C., 5% $CO_2$ and 10% humidity.

All live cell imaging experiments used either NIH 3T3 mouse skin fibroblast cells, PC-3 cells, a grade 3 human prostate adenocarcinoma, or Chinese hamster ovary cells (CHO). These are all well-studied cell lines with discrete morphological compositions. Each molecular machine was used as a stock solution at 0.10 to 1.00 µM with total dimethyl sulfoxide (DMSO) concentrations not exceeding 0.1% in the final cell media in order to avoid unwanted cell membrane permeabilization, the DMSO being required for solubility of the organic nanomachines. All loading experiments are carried out in a light-suppressed manner and the possibility of induced or accelerated uptake due to interaction between the molecular motors and the applied co-stain has been eliminated using a series of individual and reversed loading experiments.

Example 1.11. Toxicity Measurements

Cell toxicity was determined using a ChemoMetec A/S NucleoCounter 3000-Flexicyte instrument with Vial-cassette cell viability cartridge using the cell stain Acridine Orange for cell detection, and the nucleic acid stain DAPI for detecting non-viable cells and Annexin V for the detection of apoptosis.

In cellular uptake studies, cells were seeded in 6-well plates and allowed to grow to 80% to 100% confluence at 37° C. in 5% $CO_2$. Culture medium was then replaced with culture medium containing 0.1% DMSO with individual nanomachines 1-10 for 24 hours at 0.10, 0.50 and 1.00 mM.

All cell colonies bearing nanomachines displayed 92±5% viability. The control blank cells were established at 95±3% viability. In addition to 0.1% DMSO being used for molecular machine introduction, all washing solutions also contained 0.1% DMSO. At this concentration, DMSO does not affect the cells. This was determined by control experiments using all imaged cell lines cultured in DMSO-free and 0.1% DMSO-containing cell media while establishing the initial control UV-induced cell death parameters. To confirm the non-activated low toxicity of these molecular machines, all live cell imaging samples with all three studied cell lines were re-incubated, using Method A, in the dark and re-imaged using only transmission microscopy using a tungsten bulb with a LP 420 nm cut off filter. These experiments confirmed that all previously non-UV-exposed cells, regardless of the cell line studied, still proliferated in the presence of the molecular motor stock solutions for up to 72 hours using visible light at a pre-set time point to assess cell morphological changes along with viability and vitality.

Example 1.12. Live Cell Microscopy Parameters

All experimental imaging parameters (i.e., laser beam size, confocal pinhole size, laser intensity, line scanning speed, scanning area (field of view, FOV), and line averaging sequences) were kept constant throughout the experiments. The accuracy and errors associated with the establishment of accelerated necrosis are determined based on one dual channel imaging sequence, which takes 15 seconds in total. This imaging sequence has been carefully established using untreated live cells.

The optimized imaging parameters allow appropriately high scanning speed to follow natural homeostatic events and identify any induced morphological or fluorescent signal localization change. Meanwhile, they also allow sufficiently long integration time for each pixel so an adequate amount of photon signals can be collected. In order to satisfy the Nyquist sampling criteria, the pixel size is set as ⅕ of the laser spot size. The images were acquired using a bidirectional 2-line averaging sequence, which gives minimal dead time (<1 ms) between line scanning. The image size was adjusted to 100×100 µm in order to study 1 to 3 cells simultaneously. Each individual experiment was repeated 3 times on triplicate slides. On each slide, at least 5 well-separated areas were imaged (Table 2).

Example 1.13. Imaging of Live Cells

Steady state fluorescence images were recorded using a PhMoNa enhanced Leica SP5 II LSCM equipped with a HCX PL APO 63×/1.40 NA LambdaBlue Oil immersion objective. As an initial control experiment to establish the UV-induced cell toxicity threshold, while mitigating voxel exposure and ensuring sufficient laser dwell time, an imaging sequence has been established to monitor cell morphological and physiological changes as a function of time. All experiments used cell-line-determined culture medium containing 0.1% DMSO.

The applied 100 Hz detection sequence was based on a bidirectional dual-channel continuous scanning method where a minimalistic non-damaging visible laser light (458 nm, 0.2 mW) is used in conjunction with the above detailed UV exposure. This is set as a 2 line/scan accumulation parallel acquisition sequence that is recorded as a function of time. Studied channels correspond to transmission images and UV-induced mitochondrial auto-fluorescence detected at 460 to 550 nm. Applicants further confirmed that the effectiveness of monitoring the UV-activated nanomechanical action on live cells using a conventional CW mercury-arc excitation source equipped with an epi-fluorescence setup consisting of a Zeiss Axiovert 200M inverted microscope, as discussed in FIG. 18.

Example 1.14. PhMoNa Equipment

The modular PhMoNa technique is based on a laser scanning confocal microscope (LSCM) harnessing spatially modulated illumination intensities, using an in situ generated raster-scanned standing wave excitation beam optical grid pattern. Such an approach allows experimental resolution in both lateral and axial domains to be improved by at least a factor of 2 (x,y=62 nm, z=188 nm @ 355 nm Ex 63×1.40 NA, 100 Hz/line, 200 nJ/voxel dwell time) and is free from time-consuming post-image processing deconvolution algorithms.

Live cell experiments have been performed on the above detailed custom built PhMoNa system based on this Leica SP5 II platform operating with a fiber-coupled 355 nm Coherent laser (Nd:YAG $3^{rd}$ Harmonic, 80 mW) for UV activation of the motor. Steady state fluorescence images were recorded using the PhMoNa enhanced Leica SP5 II LSCM confocal microscope equipped with a HCX PL APO 63×/1.40 NA LambdaBlue Oil immersion objective.

Data were collected using 2× digital magnification at 100 Hz/line scan speed (4-line average, bidirectional scanning) at 355 nm ($3^{rd}$ harmonic NdYAG laser, set at 20 mW, 400 nJ/voxel total dwell time). In order to achieve excitation with maximal probe emission, the microscope was equipped with a triple channel imaging detector, comprising a conventional PMT systems and two HyD hybrid avalanche photodiode detectors. The latter parts of the detection system, when operated in the BrightRed mode, is capable of improving imaging sensitivity by 25%, reducing signal to noise by a factor of 5. Frame size was determined at 1024×1024 pixel, with ×2 digital magnification to ensure illumination flatness of field and 0.6 airy disc unit determining the applied pinhole diameter rendering on voxel to be corresponding to 62×62 $nm^2$ (frame size 125×125 $\mu m^2$) with a section thickness set at 188 nm (at 355 nm excitation). A HeNe or Ar ion laser was used to aid transmission image capture and when commercially available organelle-specific stains (e.g. MitotrackerRed™ or PI) were used to corroborate cellular compartmentalization or follow the onset of necrosis All imaging parameters were kept constant across experiments. This includes voxel size, laser power, line speed and averaging sequences, unless otherwise noted. The accuracy and errors associated with the establishment of accelerated necrosis is one frame dual channel imaging sequence that totals 15 seconds.

The threshold algorithm to control brightness automated by the Leica SP5 II software is calculated by the image specific signal-to-noise ratio or it is accessible post image-processing.

Example 1.15. Additional Discussion

Although PI's molar extinction coefficient is relatively low compared to other organic cell dyes, upon intercalation, its red fluorescence emission intensity increases by more than 10 times, thereby becoming a suitable counter-stain to assess and establish the onset of UV-induced necrosis. In light of its favorable spectroscopic properties, no major alteration of the experimental parameters are needed other than exchange of the 488 nm laser line, used to generate transmission images, to 543 nm (0.2 mW, also confirmed to be non-disruptive to cells).

When PC-3 cells are loaded at 0.5 or 1.0 µM with 9 or 10, washed three times (Method B) or unwashed (Method A) after 24 hours of incubation, the cells visually appear without major signs of toxicity. However, the cells which had been incubated with 9 or 10 over 24 hours were not dividing as prolifically. The cultures appear to be populated ~25% less in the presence of 9 and 20% of the cells in 10 compared to control untreated cells (FIG. 12).

Upon subsequent transmission microscopy verification, this was found to be in agreement with the amount of mobilized cells present with the experiments in the cell culture media. In order to further investigate this point, these cells were collected via gentle centrifugation and re-suspended in fresh PBS and analyzed by Image Cytometry. Using Annexin V, these cells were all confirmed to show signs of apoptosis at 93±5%. This is in contrast to the remaining coverslip surface-bound cells that appear healthy.

After harvesting the cells via trypsination (0.25% v/v), subsequent tests showed no sign of cell apoptosis (<5%). These latter types of non-apoptotic cells show identical percentage of necrosis acceleration upon subsequent UV-activation of the cell-surface bound nanomachines compared to their shorter incubation time analogues. Thus, it appears that, upon 24 hour incubation, a noticeable amount of cells have nanomachines 9 and 10 either bound to vital cell membrane channels or transport proteins or they are internalized, subsequently shutting down some natural homeostatic mechanisms that leads to programmed cell death (FIGS. 12A-E). Furthermore, this is not the case with shorter incubation times regardless of whether Method A or B is used.

In a separate experiment, PC-3 cells are also incubated for 30 minutes to 4 hours with 9 or 10, and then washed three times and further incubated for 24 hours in rotor free media to see if they retain their surface-bound molecular rotors. The cells are then UV-activated to see if necrosis would be induced at the previously established accelerated time points.

However, UV-activated nanomechanical accelerated necrosis did not occur to the same extent as seen before. Some cells lose their bound motor activity or the motors themselves were lost. The cells die only 25% faster rather than the expected 40 to 50% accelerated necrosis since there is no constant 0.5 or 1.0 µM nanomachine exposure of the cells in the culture media (i.e. constant flux). In these experiments, cell proliferation is comparable (within 5%) to the control molecular motor-free cells.

In summary, the surface bound rotors upon 24 hour incubation only induce a noticeable amount of apoptotic cell toxicity via suspected internalization or membrane adhesion if there is a constant flux of nanomachines in the medium. Nanomachines 9 and 10 appear to detach from the cell-surface with their lack of concentration gradient from the media. Hence, there is no triggered apoptosis. There is no difference between 9 and 10 in these experiments (FIGS. 12-13).

The control molecular motor-free NIH 3T3 cells and the cells loaded with either 9 or 10 (0.5 to 1.0 µM) are identical without any change in behavior or onset of UV-induced nanomechanical necrosis. This is the same as in overnight media incubation. The cells show signs of proliferation of 10 to 25%. NIH 3T3 cells incubated for 9 for 24 hours seem to be the same as the cells exposed for 1-2 hours with no change in rates upon UV-accelerated nanomechanical necrosis compared to motor-free blanks (FIG. 13).

Thus, 9 does not diffuse into NIH 3T3 cells and thereby have nanomechanical-induced necrosis or apoptosis. Cell proliferation is slower than blank motor-free cells but that could be the result of 9 binding to essential proteins or supplements in the media, slowing natural cell homeostasis.

NIH 3T3 cells incubated with 10 for 24 hours are similar to those incubated with 9 except that in the case of 10, the NIH 3T3 cells did not proliferate as much and upon UV irradiation. Rather, the cells die 15 to 20% faster with necrosis than untreated motor-free blanks (FIG. 14). Hence, mono-peptide-bearing nanomachine 10 can be internalized or membrane bound upon 24 hours of incubation, but in smaller quantities that do not trigger any noticeable toxic effect that could lead to programmed apoptotic cell death, while 10 only accelerates necrosis with less than half the efficiency compared to identical experiments using the targeted PC-3 cells.

In order to further confirm the selectivity of peptide-bearing rotor compounds 9 and 10 to PC-3 cells, the CHO cell line was studied in an identical manner through experiments described above using NIH 3T3 control cells. In the case of this second non-targeted cell line, identical results were found as had been seen in the NIH 3T3 cells, confirming that nanomachines 9 and 10 selectively target the PC-3 cell line over CHO cells (FIG. 15).

An evaluation of the forces produced by the UV-activated molecular machines upon the bilipid membranes is considered here. Membrane rupture and pore formation under a tangential mechanical force have been studied theoretically and experimentally. Generally, when the stress of the membrane exceeds their critical value, membrane rupture occurs. The critical rupture tension of biological membranes varies from 1 to 30 mN m$^{-1}$, depending on the specific chemical composition of the membrane. It has also been shown that the rupture stress is dependent on the stress loading rates. For example, it has been shown that in impulse stretching experiments over tens of μs, red blood cell membranes can sustain the stress by ten times over stresses induced by quasi-static stretching conditions. Further, pore formation is a highly dynamic process whereupon the pores either close or continue to grow until rupture of the membrane. Under tension, pore formation becomes faster, though the pore formation is a transient event, which is challenging to capture.

Based upon the studies performed, the following features appear preferred for molecular machine opening of cellular membranes. A rapidly spinning rotor is preferred because no membrane perturbation was observed without rotation. All of the nanomachines studied here have rotors that can rotate in a 2 to 3 MHz regime, and there was sufficient rotary actuation for disruption.

Moreover, smaller and addend-unencumbered molecular machines are preferred over the more encumbered systems. The molecular machines preferably embed in the membranes to show opening because their mere presence in the medium may not be sufficient in all circumstances.

When targeting, it is preferred to have a targeting addend that does not impede rotor operation. If using two relatively large addends, they might retard the rotor from interacting with the lipid bilayer, thereby slowing the nanomechanical perturbation of the membrane. Since these are molecular-sized, pore formation on the membranes is not immediate. The process can take about 1 minute to become detectable through leakage currents and twice that long based upon morphological changes. Sufficient rupture stress will have to be displayed by the rotors in order to be effective in bilayer disruption. Finally, shorter UV-actuation times of <30 scan permit analytes in the medium to enter the cells before the cells can reach the stage of programmed cell death.

Although all of the nanomachines studied here have rotors that can rotate in the 2 to 3 MHz regime, Applicants did not always excite the motors to their full speeds. In the confocal imaging experiments, the UV illuminations were ~10 MW cm$^2$, exceeding the motor saturation illumination level, which is ~10 kW cm$^2$, assuming that the motor absorption cross section is 10$^{-16}$ cm$^2$. In the synthetic vesicle releasing experiments and patch clamp studies, Applicants were using only ~10 W cm$^{-2}$ UV illumination power. On the other hand, the UV illumination was continuous in the synthetic vesicle and patch clamp studies while the confocal illumination was intermittent.

Therefore, the total dosage of UV illumination was on a similar level across the different experiments in this study. Accordingly, it is likely that the total dosage of UV illumination is an important parameter since Applicants observed the membrane rupture on similar time scales across the three experiments: synthetic vesicles, confocal imaging on three different live cells types, and whole patch clamp on a fourth live cell type.

In summary, nanomechanical action can disrupt external or internal cellular membranes and it can be used to introduce analytes into cells or expedite cell death. By synthetic design, the nanomachines can be tracked within a cell or used to target specific cells through unique cell-surface recognition elements. The efficacy of this method for in vitro studies was demonstrated. Extensions to in vivo applications can be envisioned, especially at locations where short UV-exposure is acceptable (e.g., dentistry, localized epidermis and colorectal treatments). The use of molecular motors that are activatable by two-photon-, near-infrared- or radio-frequency-inputs, would make broader in vivo treatments viable.

Example 2. Use of Two-Photon Near-Infra Red Radiation to Induce Molecular Mechanical Opening of Cells In this Example, Applicants demonstrate that a two-photon illumination in the near-infra red (IR) region can activate molecular motors 3, 8 and 9 (structures shown in FIGS. 2C 2D-1 and 2D-2), thereby resulting in Propidium Iodide (PI) dyes entering NIH 3T3 or PC 3 cells. Two-photon microscopy studies of NIH 3T3 cells were executed on a Nikon E600 upright confocal microscope coupled to a tuneable (710-950 nm Coherent MaiTai) multiphoton source operating at (20%) 240 mW power using a 166 lps scan speed and 128×128 pixel frame resolution for MP-illumination. Images (512×512 pixel, 166 lps) were recorded using a 543 nm (1 mW HeNe) laser combined with a 560 nm long-pass filter to record PI (200 nM) fluorescence and follow the onset of induced necrosis.

The results are shown in FIGS. 19A-D. In particular, FIG. 19A shows images of cells in live cell media (10% FBS) with no molecular motors present. FIG. 19B shows images of identical cells but with a 1 μM control molecular motor 5 (structure shown in FIG. 2C and described in Example 1 as lacking a rotor but still absorbing UV-light) using Method A (10 minute pre-incubation prior to imaging, as described in Example 1). FIG. 19C shows images of identical cells but with 1 μM of molecular motor 3 present using Method A (10 minute pre-incubation prior to imaging, as described in Example 1). FIG. 19D shows images of PC-3 cells with 1.0 μM of molecular motor 8 present using Method B (1 hour pre-incubation followed by washing and subsequent imaging, as described in Example 1).

Two photon live cell microscopy studies were also executed on a Nikon E600 upright confocal microscope coupled to a tuneable (710-950 nm Coherent MaiTai) multiphoton source operating at (19.8%) 240 mW power at 720 nm using 166 lines/sec scan speed and 128×128 pixel frame resolution for MP-illumination. An oil immersion Nikon IR objective (×60/1.4 NA) was used. Images (512×512 pixel, 166 l/s) were recorded using a 543 nm (1 mW HeNe) laser combined with a 570 nm long-pass filter to record PI dyes (200 nM). Fluorescence was measured as 2 frame averaged images in order to follow the onset of induced necrosis. Necrosis times have been assigned to detectable PI signals in the nucleolus.

The results are shown in FIG. 20, where the scale bars correspond to 20 µm. Time points correspond to duration of continuous multi-photon exposure in 1 minute segments only paused for PI imaging. FIG. 20A shows images of control NIH 3T3 cells in live cell media (10% FBS) with no molecular motors present. FIG. 20B shows images of identical NIH 3T3 cells with 1 µM of molecular motor 5 present using Method A. FIG. 20C shows images of identical NIH 3T3 cells with 1 µM of molecular motor 3 present using Method A. FIG. 20D shows images of NIH 3T3 cells with 1 µM of molecular motor 8 present using Method B (1 hour pre-incubation prior washing and subsequent imaging). FIG. 20E shows images of identical control PC3 cells with no molecular motors present. FIG. 20F shows images of identical PC3 cells with 1 µM of molecular motor 3 present using Method A. FIG. 20G shows images of identical PC3 cells with 1 µM of molecular motor 5 present using Method A. FIG. 20H shows images of identical PC3 cells with 1 µM of molecular motor 3 present using Method B. FIG. 20I shows images of identical PC3 cells with 1 µM of molecular motor 8 present using Method A. FIG. 20J shows images of identical PC3 cells with 1 µM of molecular motor 9 present using Method A. FIG. 20K shows images of identical PC3 cells with 1 µM of molecular motor 8 present using Method B. FIG. 20L shows images of identical PC3 cells with 1 µM of molecular motor 9 present using Method B.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of opening a lipid bilayer, wherein the method comprises:
    associating the lipid bilayer with a molecule,
        wherein the molecule comprises the following structure:

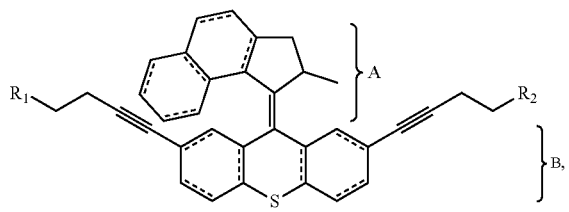

wherein region A is a moving component capable of moving in response to an external stimulus,
        wherein region B is a base component capable of embedding with the lipid bilayer, and
    wherein $R_1$ and $R_2$ are each independently selected from the group consisting of hydrogen, alkanes, alkenes, alkynes, carboxyl groups, ketone groups, alkoxy groups, methoxy groups, ethers, nitro groups, nitriles, sulfates, sulfonates, halogens, amine groups, amide groups, alcohols, aromatic groups, aryl groups, phenyl groups, annulated rings, carbohydrates, polysaccharides, peptides, targeting agents, tracing agents, fluorophores, solubilizing agents, active agents, and combinations thereof; and
    exposing the molecule to an external stimulus,
        wherein the exposing causes the moving component of the molecule to move, and
        wherein the movement facilitates the opening of the lipid bilayer.

2. The method of claim 1, wherein the molecule comprises a targeting agent for directing the molecule to a desired lipid bilayer.

3. The method of claim 2, wherein the targeting agent is selected from the group consisting of amino acids, peptides, proteins, aptamers, antibodies, small molecules, carbohydrates, polysaccharides, and combinations thereof.

4. The method of claim 1, wherein the molecule comprises a tracing agent for tracking the molecule.

5. The method of claim 4, wherein the tracing agent is selected from the group consisting of fluorophores, chromophores, dyes, radio-labeled molecules, radioactive nuclei, high contrast agents, gadolinium, gallium, thallium, fluorinated compounds, and combinations thereof.

6. The method of claim 1, wherein the molecule comprises a solubilizing agent for maintaining the water solubility of the molecule.

7. The method of claim 6, wherein the solubilizing agent is selected from the group consisting of peptides, glycols, alcohols, carboxylates, polysaccharides, salts, acids, polyethers, polyethylene glycols (PEGs), carbohydrates, and combinations thereof.

8. The method of claim 1, wherein the molecule comprises an active agent.

9. The method of claim 8, wherein the active agent is releasably associated with the molecule.

10. The method of claim 8, wherein the active agent is selected from the group consisting of drugs, peptides, polypeptides, nucleotides, DNA, RNA, siRNA, enzymes, and combinations thereof.

11. The method of claim 1, wherein the lipid bilayer is a component of cell membranes in vivo.

12. The method of claim 1, wherein the lipid bilayer is a component of cell membranes in vitro.

13. The method of claim 1, wherein the exposing comprises exposure of the lipid bilayer to an energy source.

14. The method of claim 13, wherein the energy source is selected from the group consisting of ultraviolet light, visible light, near-infra red light, a radio frequency energy source, a magnetic field, a two-photon energy source, an electric field, an electromagnetic field, and combinations thereof.

15. The method of claim 13, wherein the energy source comprises ultraviolet light.

16. The method of claim 1, wherein the movement is selected from the group consisting of rotation, flapping, jumping, and combinations thereof.

17. The method of claim 1, wherein the movement comprises rotation.

18. The method of claim 1, wherein the movement comprises flapping.

19. The method of claim 1, wherein the moving of the moving component facilitates the opening of the lipid bilayer by facilitating the formation of pores in the lipid bilayer.

20. The method of claim 1, wherein the opening of the lipid bilayer allows for the passage of materials through the lipid bilayer.

21. The method of claim 20, wherein the materials are selected from the group consisting of analytes, active agents, drugs, nucleotides, DNA, RNA, siRNA, polypeptides, enzymes, polysaccharides, imaging agents, and combinations thereof.

22. The method of claim 20, wherein the opening of the lipid bilayer allows for the passage of materials through the lipid bilayer and into cells.

23. The method of claim 20, wherein the passage of materials occurs in vitro.

24. The method of claim 20, wherein the passage of materials occurs in vivo.

25. The method of claim 1, wherein the exposing occurs after associating the molecule with the lipid bilayer.

26. The method of claim 1, wherein the exposing occurs before or during associating the molecule with the lipid bilayer.

27. The method of claim 1, wherein the associating occurs in vitro.

28. The method of claim 1, wherein the associating occurs in vivo in a subject.

29. The method of claim 28, wherein the associating comprises administering the molecule to the subject.

30. The method of claim 29, wherein the molecule is co-administered with an energy source capable of providing the external stimulus.

31. The method of claim 30, wherein the energy source comprises a light source.

32. The method of claim 30, wherein the molecule is co-administered with an active agent.

33. The method of claim 29, wherein the administered molecule is used to treat a disease in the subject.

34. The method of claim 33, wherein the disease is a skin-related cancer selected from the group consisting of skin cancer, colorectal cancer, oral cancer, vaginal cancer, and combinations thereof.

* * * * *